United States Patent
Basu et al.

(10) Patent No.: US 10,662,436 B2
(45) Date of Patent: May 26, 2020

(54) GENETIC MARKERS ASSOCIATED WITH DROUGHT TOLERANCE IN MAIZE

(71) Applicant: Syngenta Participations AG, Basel (CH)

(72) Inventors: Shib Sankar Basu, Research Triangle Park, NC (US); Michael Mahlon Magwire, Research Triangle Park, NC (US)

(73) Assignee: Syngenta Participation AG, Basel (CH)

( * ) Notice: Subject to any disclaimer, the term of this patent is extended or adjusted under 35 U.S.C. 154(b) by 0 days.

(21) Appl. No.: 16/037,393

(22) Filed: Jul. 17, 2018

(65) Prior Publication Data

US 2018/0312863 A1  Nov. 1, 2018

Related U.S. Application Data

(63) Continuation of application No. 14/967,593, filed on Dec. 14, 2015, now Pat. No. 10,047,373.

(60) Provisional application No. 62/093,055, filed on Dec. 17, 2014.

(51) Int. Cl.
| | |
|---|---|
| *A01H 5/10* | (2018.01) |
| *C12N 15/82* | (2006.01) |
| *C12Q 1/6895* | (2018.01) |
| *A01H 1/04* | (2006.01) |

(52) U.S. Cl.
CPC ........... *C12N 15/8273* (2013.01); *A01H 1/04* (2013.01); *A01H 5/10* (2013.01); *C12Q 1/6895* (2013.01); *C12Q 2600/13* (2013.01); *C12Q 2600/156* (2013.01); *Y02A 40/132* (2018.01)

(58) Field of Classification Search
None
See application file for complete search history.

(56) References Cited

U.S. PATENT DOCUMENTS

| | | |
|---|---|---|
| 2011/0191892 A1 | 8/2011 | Kishore et al. |
| 2016/0355835 A1 | 12/2016 | Frommer |

OTHER PUBLICATIONS

*Zea mays* cultivar B73 chromosome 10 clone CH201-96115, GenBank sequence with accession No. AC207557, published Sep. 23, 2013, selected pages.*
*Zea mays* cultivar B73 chromosome 5 clone CH201-257F15, GenBank accession No. AC208973, published Sep. 23, 2013.

* cited by examiner

*Primary Examiner* — Bratislav Stankovic
(74) *Attorney, Agent, or Firm* — Amy Krom

(57) ABSTRACT

The present invention relates to methods and compositions for identifying, selecting and/or producing a maize plant or maize plant part having increased yield under non-drought conditions, increased yield stability under drought conditions, and/or increased drought tolerance. A maize plant or maize plant part, including any progeny and/or seeds derived from a maize plant or germplasm identified, selected and/or produced by any of the methods of the present invention is also provided.

3 Claims, 1 Drawing Sheet

Specification includes a Sequence Listing.

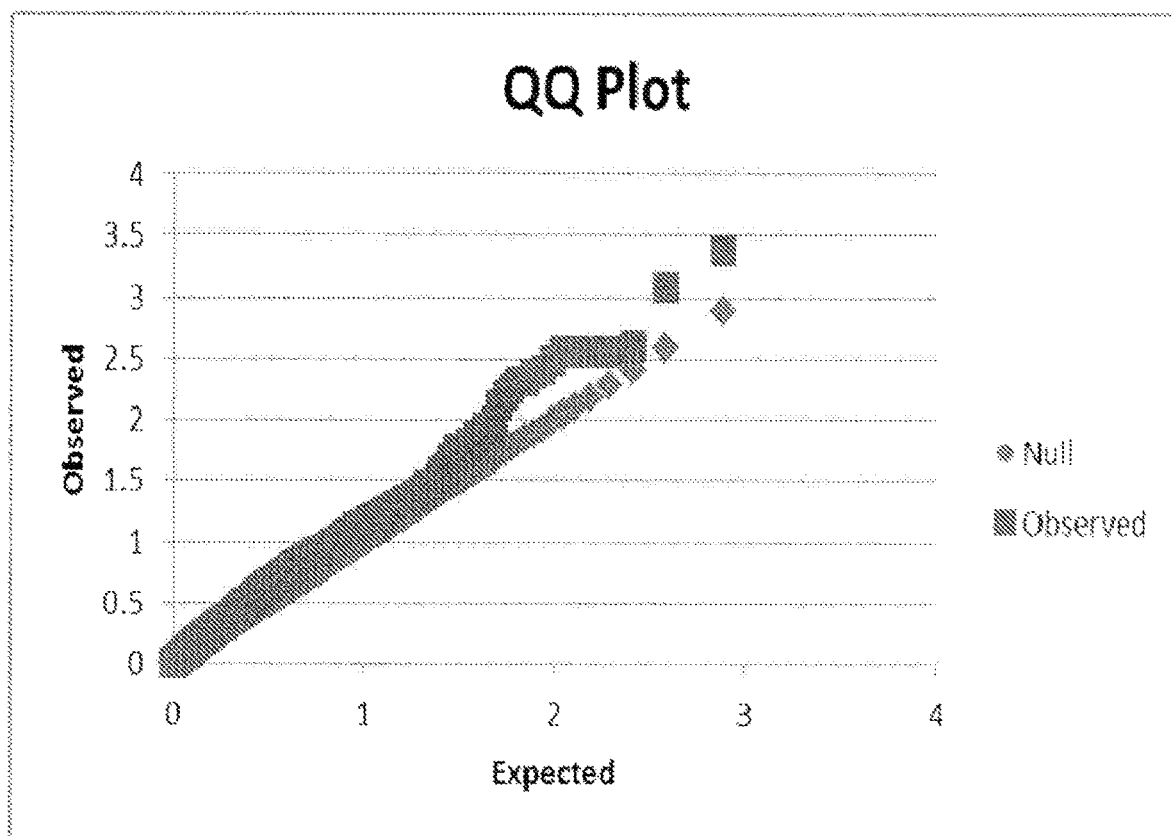

GENETIC MARKERS ASSOCIATED WITH DROUGHT TOLERANCE IN MAIZE

CROSS REFERENCES TO RELATED APPLICATIONS

The presently disclosed subject matter is a continuation of U.S. patent application Ser. No. 14/967,593 filed Dec. 14, 2015 which claims the benefit of U.S. Provisional Patent Application Ser. No. 62/093,055, filed Dec. 17, 2014, the disclosure of which is incorporated herein by reference in its entirety.

FIELD OF THE INVENTION

The present invention relates to compositions and methods for identifying, selecting and/or producing maize plants having increased yield under non-drought conditions, increased yield stability under drought conditions, and/or increased drought tolerance.

STATEMENT REGARDING ELECTRONIC SUBMISSION OF A SEQUENCE LISTING

A Sequence Listing in ASCII text format, submitted under 37 C.F.R. § 1.821, entitled "80664-US-REG-ORG-NAT-1_Sequence_Listing_ST25", 38 kilobytes in size, generated Dec. 9, 2015 and filed via EFS-Web is provided in lieu of a paper copy. The Sequence Listing is hereby incorporated by reference into the specification for its disclosures.

BACKGROUND

A goal of plant breeding is to combine various desirable traits in a single plant. For field crops such as corn, these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Once discovered, these desirable loci can be selected for as part of a breeding program in order to generate plants that carry desirable traits. An exemplary method for generating such plants includes the transfer by introgression of nucleic acid sequences from plants that have desirable genetic information into plants that do not by crossing the plants using traditional breeding techniques.

Desirable loci can be introgressed into commercially available plant varieties using marker-assisted selection (MAS) or marker-assisted breeding (MAB). MAS and MAB involves the use of one or more of the molecular markers for the identification and selection of those progeny plants that contain one or more loci that encode the desired traits. Such identification and selection can be based on selection of informative markers that are associated with desired traits. MAB can also be used to develop near-isogenic lines (NIL) harboring loci of interest, allowing a more detailed study of the effect each locus can have on a desired trait, and is also an effective method for development of backcross inbred line (BIL) populations.

Drought is one of the major limitations to maize production worldwide. Identifying genes that enhance the drought tolerance of maize may lead to more efficient crop production by allowing for the identification, selection and production of maize plants with improved water optimization traits and enhanced drought tolerance.

SUMMARY OF THE INVENTION

Compositions and methods for identifying, selecting and/or producing maize plants having increased yield under non-drought conditions, increased yield stability under drought conditions, and/or increased drought tolerance are provided. As described herein, a marker associated with increased yield under non-drought conditions, increased yield stability under drought conditions, and/or increased drought tolerance may comprise, consist essentially of or consist of a single allele or a combination of alleles at one or more genetic loci.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant, wherein said at least one marker locus is located within a chromosomal interval comprising (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283 (S_7767535); (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467 (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482 (S_25177407); (bbb) a chromosome interval on chromosome 5 defined by and including base pair (bp) position 164855482 to base pair (bp) position 164858109; or (ccc) any combination of (a) to (bbb) above, thereby identifying, selecting and/or producing a maize plant having increased yield under non-drought conditions, increased yield stability under drought conditions.

In some embodiments, a method of identifying, selecting and/or producing a maize plant having increased yield under non-drought conditions, increased yield stability under drought conditions, and/or increased drought tolerance is provided, comprising: detecting, in a maize plant or maize plant part, the presence of an allele of at least one marker locus associated with increased yield under non-drought conditions, increased yield stability under drought conditions, and/or increased drought tolerance in a maize plant, wherein said allele of at least one marker locus comprises: (a) a G allele at base pair (bp) position 14762443; (b) a C allele at base pair (bp) position 14765098; (c) an A allele at base pair (bp) position 14765012; (d) an A allele at base pair (bp) position 14764839; (e) a G allele at base pair (bp) position 14764763; (f) a C allele at base pair (bp) position 14764762; (g) a G allele at base pair (bp) position 14764658; (h) a G allele at base pair (bp) position 14764415; (i) a G allele at base pair (bp) position 171748815; (j) a C allele at base pair (bp) position 171752467; (k) a G allele at base pair (bp) position 171752311; (l) a C allele at base pair (bp) position 171749536; (m) an A allele at base pair (bp) position 171749318; (n) an A allele at base pair (bp) position 171749283; (o) a C allele at base pair (bp) position 171749273; (p) an A allele at base pair (bp) position 194932443; (q) a T allele at base pair (bp) position 194935353; (r) a C allele at base pair (bp) position 33363546; (s) an A allele at base pair (bp) position 33368983; (t) a T allele at base pair (bp) position 33363625; (u) a C allele at base pair (bp) position 164854921; (v) a G allele at base pair (bp) position 164858109; (x) an A allele at base pair (bp) position 164855482; or (y) any combination of (a) to (x) above, thereby identifying, selecting and/or producing a maize plant having increased yield under non-drought conditions, increased yield stability under drought conditions.

Accordingly, in some embodiments, a method of identifying, selecting and/or producing a maize plant having increased yield under non-drought conditions, increased yield stability under drought conditions, and/or increased drought tolerance is provided, comprising: detecting, in a maize plant or maize plant part, an allele of at least one marker locus that is associated with increased yield under non-drought conditions, increased yield stability under drought conditions, and/or increased drought tolerance in a maize plant, wherein said at least one marker comprises: "C" at a nucleotide position that corresponds to position 401 of SEQ ID NO: 6 (PZE1014822710), "A" at a nucleotide position that corresponds to position 401 of SEQ ID NO: 7 (PZE1014822787), "G" at a nucleotide position that corresponds to position 401 of SEQ ID NO: 8 (PZE1014822363), "A" at a nucleotide position that corresponds to position 401 of SEQ ID NO: 9 (PZE1014822960), "G" at a nucleotide position that corresponds to position 251 of SEQ ID NO: 10 (S_3355011), "G" at a nucleotide position that corresponds to position 401 of SEQ ID NO: 11 (PZE1014822606), "G" at a nucleotide position that corresponds to position 401 of SEQ ID NO: 12 (PZE03170079889), "C" allele at a nucleotide position that corresponds to position 401 of SEQ ID NO: 13 (PZE03170077114), "C" at a nucleotide position that corresponds to position 251 of SEQ ID NO: 14 (S_7767530), "A" at a nucleotide position that corresponds to position 251 of SEQ ID NO: 15 (S_7767535), "A" at a nucleotide position that corresponds to position 251 of SEQ ID NO: 16 (S_7767546), "A" at a nucleotide position that corresponds to position 401 of SEQ ID NO: 17 (PZE01194799632), "T" at a nucleotide position that corresponds to position 401 of SEQ ID NO: 18 (PZE0833363225), and "A" at a nucleotide position that corresponds to position 251 of SEQ ID NO: 19 (S_25177407).

In some embodiments, a method of selecting a maize plant or germplasm having increased yield under non-drought conditions, increased yield stability under drought conditions, and/or increased drought tolerance is provided, comprising crossing a first maize plant or germplasm with a second maize plant or germplasm, wherein said first maize plant or germplasm comprises within its genome a genetic marker associated with increased yield under non-drought conditions, increased yield stability under drought conditions, and/or increased drought tolerance in a maize plant, wherein said genetic marker comprises any of (a) to (y), above.

In some embodiments, a plant can be regenerated from a plant part in which said genetic marker(s) is/are detected.

Also provided herein are maize plants and maize plant parts produced, selected and/or identified by the methods of the invention, as well as crops comprising said maize plants, harvested products produced from said plants and crops, and post-harvest products produced from the harvested products.

These and other aspects of the invention are set forth in more detail in the description of the invention below.

BRIEF DESCRIPTION OF THE DRAWINGS

FIG. 1 provides the QQ plot generated to look at the observed distribution of −log 10(P-values) of the data a shown in Tables 2.1-2.4.

BRIEF DESCRIPTION OF THE SEQUENCE LISTING

SEQ ID NO.: 1 ZmSWEET13a [GRMZM2G173669]
  GRMZM2G173669 coord=10:14762443..14765098:1
SEQ ID NO.: 2 ZmSWEET1a [GRMZM2G039365]
  GRMZM2G039365 coord=3:171748815..171752467:−1
SEQ ID NO.: 3 ZmSWEET11/MtN3 [GRMZM2G368827]
  GRMZM2G368827 coord=1:194932443..194935353:−1
SEQ ID NO.: 4 ZmSWEET16b [GRMZM2G111926]
  GRMZM2G111926 coord=8:33363546..33368983:−1
SEQ ID NO.: 5 ZmSWEET15b [GRMZM5G872392]
  GRMZM5G872392 coord=5:164854921..164858109:−1
SEQ ID NO.: 6 PZE1014822710
  C/T SNP AT NUCLEOTIDE 401 identifies a favorable/unfavorable allele
SEQ ID NO.: 7 PZE1014822787
  A/G SNP AT NUCLEOTIDE 401 identifies a favorable/unfavorable allele
SEQ ID NO.: 8 PZE1014822363
  G/T SNP AT NUCLEOTIDE 401 identifies a favorable/unfavorable allele
SEQ ID NO.: 9 PZE1014822960
  A/G SNP AT NUCLEOTIDE 401 identifies a favorable/unfavorable allele
SEQ ID NO.: 10 S_3355011
  G/C SNP AT NUCLEOTIDE 251 identifies a favorable/unfavorable allele
SEQ ID NO.: 11 PZE1014822606
  G/T SNP AT NUCLEOTIDE 401 identifies a favorable/unfavorable allele
SEQ ID NO.: 12 PZE03170079889
  G/A SNP AT NUCLEOTIDE 401 identifies a favorable/unfavorable allele
SEQ ID NO.: 13 PZE03170077114
  C/T SNP AT NUCLEOTIDE 401 identifies a favorable/unfavorable allele
SEQ ID NO.: 14 S_7767530
  C/T SNP AT NUCLEOTIDE 251 identifies a favorable/unfavorable allele
SEQ ID NO.: 15 S_7767535
  A/C SNP AT NUCLEOTIDE 251 identifies a favorable/unfavorable allele
SEQ ID NO.: 16 S_7767546
  A/C SNP AT NUCLEOTIDE 251 identifies a favorable/unfavorable allele
SEQ ID NO.: 17 PZE01194799632
  A/T SNP AT NUCLEOTIDE 401 identifies a favorable/unfavorable allele
SEQ ID NO.: 18 PZE0833363225
  T/C SNP AT NUCLEOTIDE 401 identifies a favorable/unfavorable allele
SEQ ID NO.: 19 S_25177407
  A/C SNP AT NUCLEOTIDE 251 identifies a favorable/unfavorable allele

DETAILED DESCRIPTION

The present invention provides compositions and methods for identifying, selecting and/or producing maize plants having increased yield under non-drought conditions, increased yield stability under drought conditions, and/or increased drought tolerance, as well as maize plants, parts thereof, including but not limited to seeds, and maize germplasm, that are identified, selected and/or produced by methods of this invention. The present invention further provides an assay for the detection of increased yield under non-drought conditions, increased yield stability under drought conditions, and/or increased drought tolerance in a maize plant, plant part and/or maize germplasm. In addition, the present invention provides maize plants, plant parts, and/or germplasm having within their genome one or more SNP or QTL markers associated with increased yield under non-drought conditions, increased yield stability under drought conditions, and/or increased drought tolerance.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-drought conditions, increased yield stability under drought conditions, and/or increased drought tolerance in a maize plant relative to a control maize plant not having the target allele or alleles. Thus, for example, a maize plant comprising one or more of the markers associated with increased yield under non-drought conditions, increased yield stability under drought conditions, and/or increased drought tolerance in a maize plant as described herein (e.g., desired alleles) can have increased yield under non-drought conditions, increased yield stability under drought conditions, and/or increased drought tolerance as compared to a maize plant that does not comprise said one or more markers associated with increased yield under non-drought conditions, increased yield stability under drought conditions, and/or increased drought tolerance (e.g., desired alleles).

A marker is "associated with" a trait when said trait is linked to the marker and when the presence of the marker is an indicator of whether and/or to what extent the desired trait or trait form will occur in a plant/germplasm comprising the marker. Similarly, a marker is "associated with" an allele or chromosome interval when it is linked to said allele or said chromosome interval and when the presence of the marker is an indicator of whether the allele or chromosome interval is present in a plant/germplasm comprising the marker. For example, "a marker associated with a drought tolerance allele" refers to a marker whose presence or absence can be used to predict whether a plant will display drought tolerance.

As used herein, the terms "backcross" and "backcrossing" refer to the process whereby a progeny plant is crossed back to one of its parents one or more times (e.g., 1, 2, 3, 4, 5, 6, 7, 8, 9, 10, or more.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In some embodiments, the number of backcrosses can be about 1 to about 10 (e.g., 1, 2, 3, 4, 5, 6, 7, 8, 9, 10). In some embodiments, the number of backcrosses is about 7.

As used herein, a "control" maize plant means a maize plant which does not comprise said marker or markers of the invention, wherein said control maize plant is grown under the same environmental conditions as the identified, selected, produced, introgressed maize plant. In some embodiments, the control maize plant can have a substantially similar genetic background (e.g., 70%, 75%, 80%, 85%, 90%, 91%, 92%, 93%, 94%, 95%, 96%, 97%, 98%, 99%, or more) to the identified, selected, produced, introgressed plant. In some embodiments, the control plant is of the same elite line as that of the identified, selected, produced, introgressed plant but does not comprise said marker or markers of the invention.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of the gametes fusing via pollination to produce progeny.

As used herein, the terms "cultivar" and "variety" refer to a group of similar plants that by structural or genetic features and/or performance can be distinguished from other cultivars or varieties within the same species.

As used herein, the terms "drought tolerance" and "drought tolerant" refer to a plant's ability to endure and/or thrive under drought stress conditions. When used in reference to a plant part, the terms refer to the ability of a plant that arises from that plant part to endure and/or thrive under drought conditions. In general, a plant or plant part is designated as "drought tolerant" if it displays "increased drought tolerance." This can be measured in terms of a single plant or in terms of the results from a group of the drought tolerant plants of this invention. Thus, for example, when measuring yield, the measurements are made on a group of the plants of the invention, which is then compared to the yield of a group of appropriate control plants.

In some embodiments, as used herein, the term "increased drought tolerance" or "enhanced drought tolerance" refers to an improvement in one or more water optimization traits as compared to one or more controls (e.g., one or both parents, or a plant lacking a marker associated with drought tolerance when grown under the same environmental conditions). Exemplary water optimization traits include, but are not limited to, water loss, accumulation of reactive oxygen species, accumulation of dehydrins, root architecture, accumulation of late embryogenesis abundant proteins, grain yield at standard moisture percentage (YGSMN), grain moisture at harvest (GMSTP), grain weight per plot (GWTPN), percent yield recovery (PYREC), yield reduction (YRED), and percent barren (PB). Thus, a plant that exhibits decreased water loss, decreased accumulation of reactive oxygen species, increased accumulation of dehydrins, improved root architecture, increased accumulation of late embryogenesis abundant proteins, increased grain yield at standard moisture percentage (YGSMN), increased grain moisture at harvest (GMSTP), increased grain weight per plot (GWTPN), increased percent yield recovery (PYREC), decreased yield reduction (YRED), and/or decreased percent barren (PB) as compared to a control plant when each is grown under the same drought stress conditions displays enhanced or increased drought tolerance and may be designated as "drought tolerant."

As used herein, "increased yield" means increased grain yield at standard moisture percentage (YGSMN) in a plant or plants of this invention as compared to a control.

As used herein, "yield stability" refers to a difference in the relative rank of a plant line under well-watered versus drought conditions. "Increased yield stability" means that there is less change in rank for the plant line in the two conditions as compared to a control.

As used herein, "drought conditions" refers to water deprived conditions that result in a loss in yield of 30% or more versus well-watered conditions.

As used herein, "non-drought conditions" means that the plants are well watered.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make up for all the genes in its genome. Genotypes can be indirectly characterized, e.g., using markers and/or directly characterized by, e.g., nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.). In some embodiments, germplasm includes but is not limited to tissue culture.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to a cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

The terms "increase," "increasing," "increased," "enhance," "enhanced," "enhancing," and "enhancement" (and grammatical variations thereof), as used herein, describe an elevation, for example, in yield, yield stability or the tolerance of a plant to drought by the introduction of a genetic marker(s) of the invention into the plant, thereby producing a plant having, for example, increased yield, yield stability, and/or drought tolerance (e.g., an elevation of at least about 20%, 25%, 30%, 35%, 40%, 45%, 50%, 75%, 100%, 125%, 150%, 175%, 200%, 350%, 300%, 350%, 400%, 450%, 500% or more). This increase can be observed by comparing the yield, yield stability, and/or drought tolerance of the plant comprising the genetic marker(s) of the invention to the yield, yield stability, and/or drought tolerance of a plant lacking said genetic marker(s) of the invention (i.e., a control).

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, 5, 6, 7, 8, 9, 10 or more times) to a line having a desired genetic background, selecting for the desired allele, with the result being that the desired allele becomes fixed in the desired genetic background. For example, a marker associated with increased yield under non-drought conditions, increased yield stability under drought conditions, and/or increased drought tolerance may be introgressed from a donor into a recurrent parent that is drought sensitive or does not comprise said marker(s) associated with increased yield under non-drought conditions, increased yield stability under drought conditions, and/or increased drought tolerance. The resulting offspring could then be backcrossed one or more times and selected until the progeny comprises the genetic marker(s) associated with increased yield under non-drought conditions, increased yield stability under drought conditions, and/or increased drought tolerance in the recurrent parent background.

As used herein, the term "linkage" refers to the degree with which one marker locus is associated with another marker locus or some other locus. The linkage relationship between a genetic marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

A centimorgan ("cM") or a genetic map unit (m.u.) is a unit of measure of recombination frequency and is defined as the distance between genes for which one product of meiosis in 100 is recombinant One cM is equal to a 1% chance that a marker at one genetic locus will be separated from a marker at a second locus due to crossing over in a single generation. Thus, a recombinant frequency (RF) of 1% is equivalent to 1 map unit (m.u.).

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., increased yield under non-drought conditions, increased yield stability under drought conditions, and/or increased drought tolerance. The degree of linkage of a genetic marker to a phenotypic trait is measured, e.g., as a statistical probability of co-segregation of that marker with the phenotype.

Linkage disequilibrium is most commonly assessed using the measure $r^2$, which is calculated using the formula described by Hill and Robertson, *Theor. Appl. Genet.* 38:226

(1968). When r²=1, complete linkage disequilibrium exists between the two marker loci, meaning that the markers have not been separated by recombination and have the same allele frequency. Values for r² above ⅓ indicate sufficiently strong linkage disequilibrium to be useful for mapping. Ardlie et al., *Nature Reviews Genetics* 3:299 (2002). Hence, alleles are in linkage disequilibrium when r² values between pairwise marker loci are greater than or equal to about 0.3, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, an allele, a gene, a haplotype, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP)) (Vos et al., *Nucleic Acids Res.* 23:4407 (1995)), a single nucleotide polymorphism (SNP) (Brookes, *Gene* 234: 177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs). A large number of maize genetic markers are known in the art, and are published or available from various sources, such as the MaizeGDB internet resource (maizegdb.org). In some embodiments, a genetic marker of this invention is a SNP allele, a SNP allele located in a chromosome interval and/or a haplotype (combination of SNP alleles), each of which is associated with increased yield under non-drought conditions, increased yield stability under drought conditions, and/or increased drought tolerance.

Markers corresponding to genetic polymorphisms between members of a population can be detected by methods well-established in the art. These include, but are not limited to, nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of randomly amplified polymorphic DNA (RAPD), detection of single nucleotide polymorphisms (SNPs), and/or detection of amplified fragment length polymorphisms (AFLPs). Thus, in some embodiments of this invention, such well known methods can be used to detect the SNP alleles as defined herein (See, e.g., Table 1).

Accordingly, in some embodiments of this invention, a marker is detected by amplifying a maize nucleic acid with two oligonucleotide primers by, for example, an amplification reaction such as the polymerase chain reaction (PCR).

A "marker allele," also described as an "allele of a marker locus," can refer to one of a plurality of polymorphic nucleotides found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the term "percent barren" (PB) refers to the percentage of plants in a given area (e.g., plot) with no grain. It is typically expressed in terms of the percentage of plants per plot and can be calculated as:

$$\frac{\text{number of plants in the plot with no grain}}{\text{total number of plants in the plot}} \times 100$$

As used herein, the term "percent yield recovery" (PYREC) refers to the effect an allele and/or combination of alleles has on the yield of a plant grown under stress conditions (e.g., drought conditions) as compared to that of a plant that is genetically identical except insofar as it lacks the allele and/or combination of alleles. PYREC is calculated as:

{1−[yield under full irrigation (w/allele(s) of interest)−yield under drought conditions (w/allele(s) of interest)]/[yield under full irrigation (w/out allele(s) of interest)−yield under drought conditions (w/out allele(s) of interest)]}×100

By way of example and not limitation, if a control plant yields 200 bushels under full irrigation conditions, but yields only 100 bushels under drought stress conditions, then its percentage yield loss would be calculated at 50%. If an otherwise genetically identical hybrid that contains the allele(s) of interest yields 125 bushels under drought stress conditions and 200 bushels under full irrigation conditions, then the percentage yield loss would be calculated as 37.5% and the PYREC would be calculated as 25% [(1.00−(200−125)/(200−100))×100].

As used herein, the term "water optimization trait" refers to any trait that can be shown to influence the yield of a plant under different sets of growth conditions related to water availability.

As used herein, the term "yield reduction" (YD) refers to the degree to which yield is reduced in plants grown under stress conditions. YD is calculated as:

$$\frac{\text{yield under non-stress conditions} - \text{yield under stress conditions}}{\text{yield under non-stress conditions}} \times 100$$

As used herein, the term "probe" refers to a single-stranded oligonucleotide sequence that will form a hydrogen-bonded duplex with a complementary sequence in a target nucleic acid sequence analyte or its cDNA derivative. Thus, a "marker probe" and "probe" refers to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. Based on the guidance provided herein, the nucleotide sequences of the genes (e.g., SEQ ID NO:1 (Gene Model ID No: GRMZM2G173669); SEQ ID NO:2 (Gene Model ID No: GRMZM2G039365); SEQ ID NO:3 (Gene Model ID No: GRMZM2G368827); SEQ ID NO:4 Gene Model ID No: GRMZM2G111926); SEQ ID NO:5 (Gene Model ID No: GRMZM2G872392) and the location of the SNPs therein, probes can be readily developed for detecting the markers of this invention.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

Based on the guidance provided herein, the nucleotide sequences of the genes (e.g., SEQ ID NO:1 (Gene Model ID No: GRMZM2G173669); SEQ ID NO:2 (Gene Model ID No: GRMZM2G039365); SEQ ID NO:3 (Gene Model ID No: GRMZM2G368827); SEQ ID NO:4 Gene Model ID No: GRMZM2G111926); SEQ ID NO:5 (Gene Model ID No: GRMZM2G872392) and the location of the SNPs therein, probes can be readily developed for detecting the markers of this invention. Particular nucleotides that are present at particular locations in the markers and nucleic acids disclosed herein can be determined using standard molecular biology techniques including, but not limited to amplification of genomic DNA from plants and subsequent sequencing. Additionally, oligonucleotide primers can be designed that would be expected to specifically hybridize to particular sequences that include the polymorphisms disclosed herein. For example, oligonucleotides can be designed to distinguish between the "C" allele and the "T" allele at a nucleotide position that corresponds to position 401 of SEQ ID NO: 6 (PZE1014822710). For example, oligonucleotides can be designed to distinguish between the "A" allele and the "G" allele at a nucleotide position that corresponds to position 401 of SEQ ID NO: 7 (PZE1014822787). For example, oligonucleotides can be designed to distinguish between the "G" allele and the "T" allele at a nucleotide position that corresponds to position 401 of SEQ ID NO: 8 (PZE1014822363). For example, oligonucleotides can be designed to distinguish between the "A" allele and the "G" allele at a nucleotide position that corresponds to position 401 of SEQ ID NO: 9 (PZE1014822960). For example, oligonucleotides can be designed to distinguish between the "G" allele and the "C" allele at a nucleotide position that corresponds to position 251 of SEQ ID NO: 10 (S_3355011). For example, oligonucleotides can be designed to distinguish between the "G" allele and the "T" allele at a nucleotide position that corresponds to position 401 of SEQ ID NO: 11 (PZE1014822606). For example, oligonucleotides can be designed to distinguish between the "G" allele and the "A" allele at a nucleotide position that corresponds to position 401 of SEQ ID NO: 12 (PZE03170079889). For example, oligonucleotides can be designed to distinguish between the "C" allele and the "T" allele at a nucleotide position that corresponds to position 401 of SEQ ID NO: 13 (PZE03170077114). For example, oligonucleotides can be designed to distinguish between the "C" allele and the "T" allele at a nucleotide position that corresponds to position 251 of SEQ ID NO: 14 (S_7767530). For example, oligonucleotides can be designed to distinguish between the "A" allele and the "C" allele at a nucleotide position that corresponds to position 251 of SEQ ID NO: 15 (S_7767535). For example, oligonucleotides can be designed to distinguish between the "A" allele and the "C" allele at a nucleotide position that corresponds to position 251 of SEQ ID NO: 16 (S_7767546). For example, oligonucleotides can be designed to distinguish between the "A" allele and the "T" allele at a nucleotide position that corresponds to position 401 of SEQ ID NO: 17 (PZE01194799632). For example, oligonucleotides can be designed to distinguish between the "T" allele and the "C" allele at a nucleotide position that corresponds to position 401 of SEQ ID NO: 18 (PZE0833363225). For example, oligonucleotides can be designed to distinguish between the "A" allele and the "C" allele at a nucleotide position that corresponds to position 251 of SEQ ID NO: 19 (S_25177407).

The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual*, Third Edition, Cold Spring Harbor Laboratory Press, Cold Spring Harbor, N.Y., United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" with regard to the comparison of two (or more) nucleotide sequences means that the two nucleotide sequences have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity. In some embodiments, two nucleotide sequences can have at least about 75%, 80%, 85%, 90%, 95%, or 100% sequence identity, and any range or value therein. In representative embodiments, two nucleotide sequences can have at least about 95%, 96%, 97%, 98%, 99% or 100% sequence identity, and any range or value therein.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST®X version 2.0 for translated nucleotide sequences and BLAST®N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST®) programs, which are publicly available from National Center Biotechnology Information (NCBI) at the National Library of Medicine, National Institute of Health, Bethesda, Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence, BLAST®X can be used to determine sequence identity; and for polynucleotide sequence, BLAST®N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, a plant part or a plant organ (e.g., leaves, stems, roots, etc.), a plant tissue, a plant tissue culture, a seed, a plant cell and/or a plant germplasm. A plant cell is a cell of a plant, taken from a plant, or derived through culture from a cell taken from a plant.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. As used herein, "plant part" can also include germplasm. Thus, a plant part includes maize tissue culture from which soybmaizeean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "maize" or "corn" refers to *Zea mays* plant(s).

As used herein, the term "reference sequence" refers to a defined nucleotide sequence used as a basis for nucleotide sequence comparison (e.g., Chromosome 10, Chromosome 3, Chromosome 1, Chromosome 5, and/or Chromosome 8 of *Zea mays* cultivar B73).

Genetic loci correlating with particular phenotypes, such as drought tolerance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with increased yield under non-drought conditions, increased yield stability under drought conditions, and/or increased drought tolerance in maize. Detection of these markers and/or other linked markers can be used to identify, select and/or produce maize plants having increased yield under non-drought conditions, increased yield stability under drought conditions, and/or increased drought tolerance and/or to eliminate maize plants from breeding programs or from planting that do not have increased yield under non-drought conditions, increased yield stability under drought conditions, and/or increased drought tolerance.

Molecular or genetic markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) Genomics 20:176-183.

Table 1 provides the names of markers (SNPs) of this invention that are associated with increased yield under non-drought conditions, increased yield stability under drought conditions, and/or increased drought tolerance in maize, the physical genetic locations of each marker on the respective maize chromosome or linkage group, and the target allele that is associated with increased yield under non-drought conditions, increased yield stability under drought conditions, and/or increased drought tolerance.

Markers of the present invention are described herein with respect to the positions of marker loci in the genome of the maize B73 variety (version 2) at the Maize Genetics and Genomics Database internet resource (gbrowse.maizegdb.org/gb2/gbrowse/maize_v2/).

See Table 1, below.

TABLE 1

The respective maize chromosome or linkage group of physical and genetic positions of the markers of the invention including allele associated with increased yield under non-drought conditions, increased yield stability under drought conditions, and/or increased drought tolerance (fav. allele).

| Gene Model ID | Gene name | Chrom. | Gene begin | Gene end | (SNP) name | Physical position in Maize B73 | Fav. Allele/ Unfav. Allele |
|---|---|---|---|---|---|---|---|
| GRMZM2G173669 | SWEET-13a | chr10 | 14762443 | 14765098 | PZE1014822710 | 14764762 | C/T |
| GRMZM2G173669 | SWEET-13a | chr10 | 14762443 | 14765098 | PZE1014822787 | 14764839 | A/G |
| GRMZM2G173669 | SWEET-13a | chr10 | 14762443 | 14765098 | PZE1014822363 | 14764415 | G/T |
| GRMZM2G173669 | SWEET-13a | chr10 | 14762443 | 14765098 | PZE1014822960 | 14765012 | A/G |
| GRMZM2G173669 | SWEET-13a | chr10 | 14762443 | 14765098 | S_3355011 | 14764763 | G/C |
| GRMZM2G173669 | SWEET-13a | chr10 | 14762443 | 14765098 | PZE1014822606 | 14764658 | G/T |
| GRMZM2G039365 | SWEET-1a | chr3 | 171748815 | 171752467 | PZE03170079889 | 171752311 | G/A |
| GRMZM2G039365 | SWEET-1a | chr3 | 171748815 | 171752467 | PZE03170077114 | 171749536 | C/T |
| GRMZM2G039365 | SWEET-1a | chr3 | 171748815 | 171752467 | S_7767530 | 171749273 | C/T |
| GRMZM2G039365 | SWEET-1a | chr3 | 171748815 | 171752467 | S_7767535 | 171749283 | A/C |
| GRMZM2G039365 | SWEET-1a | chr3 | 171748815 | 171752467 | S_7767546 | 171749318 | A/C |
| GRMZM2G368827 | SWEET-11/MtN3 | chr1 | 194932443 | 194935353 | PZE01194799632 | 194932443 | A/T |
| GRMZM2G111926 | SWEET-16b | chr8 | 33363546 | 33368983 | PZE0833363225 | 33363625 | T/C |
| GRMZM5G872392 | SWEET-15b | chr5 | 164854921 | 164858109 | S_25177407 | 164855482 | A/C |

Thus, in some embodiments of this invention, the marker alleles associated with increased yield under non-drought conditions, increased yield stability under drought conditions, and/or increased drought tolerance in maize are as set forth in Table 1.

In some embodiments of this invention, the marker allele(s) associated with increased yield under non-drought conditions, increased yield stability under drought conditions, and/or increased drought tolerance as set forth in Table 1 can be located in a chromosomal interval including, but not limited to (a) a chromosome interval on chromosome 10 defined by and including base pair (bp) position 14762443 to base pair (bp) position 14765098 (Gene Model ID No: GRMZM2G173669); (b) a chromosome interval on chromosome 10 defined by and including base pair (bp) position 14762443 to base pair (bp) position 14765012 (PZE10148229607.S_3355639); (c) a chromosome interval on chromosome 10 defined by and including base pair (bp) position 14762443 to base pair (bp) position 14764839 (PZE1014822787.S_3355210); (d) a chromosome interval on chromosome 10 defined by and including base pair (bp) position 14762443 to base pair (bp) position 14764763 (S_3355011); (e) a chromosome interval on chromosome 10 defined by and including base pair (bp) position 14762443 to base pair (bp) position 14764762 (PZE1014822710.S_3355009); (f) a chromosome interval on chromosome 10 defined by and including base pair (bp) position 14762443 to base pair (bp) position 14764658 (PZE101482206.S_3354710); (g) a chromosome interval on chromosome 10 defined by and including base pair (bp) position 14762443 to base pair (bp) position 14764415 (PZE1014822363.S_3353987); (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467 (Gene Model ID No: GRMZM2G039365); (cc) a chromosome interval on chromosome 3 defined by and including base pair (bp) position 171748815 to base pair (bp) position 171752311 (PZE03170079889.S_7768072); (dd) a chromosome interval on chromosome 3 defined by and including base pair (bp) position 171748815 to base pair (bp) position 171749536 (PZE03170077114.S_7767618); (ee) a chromosome interval on chromosome 3 defined by and including base pair (bp) position 171748815 to base pair (bp) position 171749318 (S_7767546); (ff) a chromosome interval on chromosome 3 defined by and including base pair (bp) position 171748815 to base pair (bp) position 171749283 (S_7767535); (gg) a chromosome interval on chromosome 3 defined by and including base pair (bp) position 171748815 to base pair (bp) position 171749273 (S_7767530); (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 (PZE01194799632) to base pair (bp) position 194935353 (Gene Model ID No: GRMZM2G368827); (ww) a chromosome interval on chromosome 8 defined by and including base pair (bp) position 33363546 to base pair (bp) position 33368983 (Gene Model ID No: GRMZM2G111926); (xx) a chromosome interval on chromosome 8 defined by and including base pair (bp) position 33363546 to base pair (bp) position 33363625 (PZE0833363225.S_16494088); (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109 (Gene Model ID No: GRMZM2G872392); (aaa) a chromosome interval on chromosome 5 defined by and including base pair (bp) position 164854921 to base pair (bp) position 164855482 (S_25177407); (bbb) a chromosome interval on chromosome 5 defined by and including base pair (bp) position 164855482 to base pair (bp) position 164858109; and (ccc) any combination of (a) to (bbb) above.

In some embodiments, bp position 14762443 comprises a G allele; bp position 14765098 comprises a C allele; bp position 14765012 comprises an A allele; bp position 14764839 comprises an A allele; bp position 14764763 comprises a G allele; bp position 14764762 comprises a C allele; bp position 14764658 comprises a G allele; bp position 14764415 comprises a G allele; bp position 171748815 comprises a G allele; bp position 171752467 comprises a C allele; bp position 171752311 comprises a G allele; bp position 171749536 comprises a C allele; bp position 171749318 comprises an A allele; bp position 171749283 comprises an A allele; bp position 171749273 comprises a C allele; bp position 194932443 comprises an A allele; bp position 194935353 comprises a T allele; bp position 33363546 comprises a C allele; bp position 33368983 comprises an A allele; bp position 33363625 comprises a T allele; bp position 164854921 comprises a C allele; bp position 164858109 comprises a G allele; and bp position 164855482 comprises an A allele.

Thus, in some embodiments, the marker allele(s) associated with increased yield under non-drought conditions, increased yield stability under drought conditions, and/or increased drought tolerance as set forth in Table 1 can be located in a chromosomal interval defined by and including (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; and (ccc) any combination of (a) to (bbb) above. In some embodiments, the allele at each base pair position can be homozygous.

Thus, for example, in some embodiments, the marker allele(s) associated with increased yield under non-drought conditions, increased yield stability under drought conditions, and/or increased drought tolerance as set forth in Table 1 can be located in a chromosomal interval defined by and including (a) a GG allele at base pair (bp) position 14764415 and an AA allele at base pair (bp) position 14765012; (b) a GG allele at base pair (bp) position 14764415 and an AA allele at base pair (bp) position 14764839; (c) a GG allele at base pair (bp) position 14764415 and a GG allele at base pair (bp) position 14764763; (d) a GG allele at base pair (bp) position 14764415 and a CC allele at base pair (bp) position 14764762; (e) a GG allele at base pair (bp) position 14764415 and a GG allele at base pair (bp) position 14764658; (f) a GG allele at base pair (bp) position 14764658 and an AA allele at base pair (bp) position 14765012; (g) a GG allele at base pair (bp) position 14764658 and an AA allele at base pair (bp) position 14764839; (h) a GG allele at base pair (bp) position 14764658 and a GG allele at base pair (bp) position 14764763; (i) a GG allele at base pair (bp) position 14764658 and a CC allele at base pair (bp) position 14764762; (j) a CC allele at base pair (bp) position 14764762 and an AA allele at base pair (bp) position 14765012; (k) a CC allele at base pair (bp) position 14764762 and an AA allele at base pair (bp) position 14764839; (l) a CC allele at base pair (bp) position 14764762 and a GG allele at base pair (bp) position 14764763; (m) a GG allele at base pair (bp) position 14764763 and an AA allele at base pair (bp) position 14765012; (n) a GG allele at base pair (bp) position 14764763 and an AA allele at base pair (bp) position 14764839; (o) an AA allele at base pair (bp) position 14764839 and an AA allele at base pair (bp) position 14765012; (p) a CC allele at base pair (bp) position 171749273 and a GG allele at base pair (bp) position 171752311; (q) a CC allele at base pair (bp) position 171749273 and a CC allele at base pair (bp) position 171749536; (r) a CC allele at base pair (bp) position 171749273 and an AA allele at base pair (bp) position 171749318; (s) a CC allele at base pair (bp) position 171749273 and an AA allele at base pair (bp) position 171749283; (t) an AA allele at base pair (bp) position 171749283 a GG allele at base pair (bp) position 171752311; (u) an AA allele at base pair (bp) position 171749283 and a CC allele at base pair (bp) position 171749536; (v) an AA allele at base pair (bp) position 171749283 and an AA allele at base pair (bp) position 171749318; (w) an AA allele at base pair (bp) position 171749318 and a GG allele at base pair (bp) position 171752311; (x) an AA allele at base pair (bp) position 171749318 and a CC allele at base pair (bp) position 171749536; and/or (y) a CC allele at base pair (bp) position 171749536 and a GG allele at base pair position 171752311.

As would be understood by one of skill in the art, additional chromosomal intervals can be defined by the SNP markers provided herein in Table 1.

In some embodiments, a genetic marker of this invention as set forth in Table 1 is associated with increased yield under non-drought conditions, increased yield stability under drought conditions, and/or increased drought tolerance in maize, wherein the genetic marker includes but is not limited to: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; and/or any combination thereof. In some embodiments, the allele at each described base pair position can be independently homozygous or heterozygous. In some embodiments, the allele at each described base pair position can be homozygous.

In some embodiments, a combination of genetic markers of this invention as set forth in Table 1 is associated with increased yield under non-drought conditions, increased yield stability under drought conditions, and/or increased drought tolerance in maize, wherein the combination of genetic markers includes but is not limited to: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467 (Gene Model ID No: GRMZM2G039365); (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353 (Gene Model ID No: GRMZM2G368827); (ww) a C allele at base pair (bp) position 33363546 and an A allele at base pair (bp) position 33368983 (Gene Model ID No: GRMZM2G111926); (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109 (Gene Model ID No: GRMZM2G872392); (aaa) a C allele at base pair (bp) position 164854921 and an A allele at base pair (bp) position 164855482; (bbb) an A allele at base pair (bp) position 164855482 and a G allele at base pair (bp) position 164858109; and (ccc) any combination of (a) to (bbb) above. In some embodiments, the allele at each described base pair position can be independently homozygous or heterozygous. In some embodiments, the allele at each described base pair position can be homozygous.

In some embodiments, the combination of markers associated with increased yield under non-drought conditions, increased yield stability under drought conditions, and/or increased drought tolerance in maize, can be any combination of markers identified on chromosome 3, markers identified on chromosome 10, markers identified on chromosome 1, markers identified on chromosome 8, or markers identified on chromosome 5. Thus, in some embodiments, a combination of markers associated with increased yield under non-drought conditions, increased yield stability under drought conditions, and/or increased drought tolerance in maize can include, but are not limited to, all or any combination of a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; and/or a G allele at base pair (bp) position 14764415 each of which are located on maize chromosome 10. In some embodiments, the combination of markers associated with increased yield under non-drought conditions, increased yield stability under drought conditions, and/or increased drought tolerance in maize can include, but are not limited to, all or any combination of a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; and/or a C allele at base pair (bp) position 171749273 each of which are located on maize chromosome 3. In some embodiments, the combination of markers associated with increased yield under non-drought conditions, increased yield stability under drought conditions, and/or increased drought tolerance in maize can include, but are not limited to, an A allele at base pair (bp) position 194932443 and/or a T allele at base pair (bp) position 194935353, which are located on maize chromosome 1. In some embodiments, the combination of markers associated with increased yield under non-drought conditions, increased yield stability under drought conditions, and/or increased drought tolerance in maize can include, but are not limited to, all or any combination of a C allele at base pair (bp) position 33363546; an A allele at base pair (bp) position 33368983; and/or a T allele at base pair (bp) position 33363625 each of which are located on maize chromosome 8. In some embodiments, the combination of markers associated with increased yield under non-drought conditions, increased yield stability under drought conditions, and/or increased drought tolerance in maize can include, but are not limited to, all or any combination of a C allele at base pair (bp) position 164854921; a G allele at base pair (bp) position 164858109; and/or an A allele at base pair (bp) position 164855482 each of which are located on maize chromosome 5. In some embodiments, the allele at each described base pair position can be independently homozygous or heterozygous. In some embodiments, the allele at each described base pair position can be homozygous.

Accordingly, this invention further provides methods of identifying, selecting, and/or producing a maize plant or part thereof having increased yield under non-drought conditions, increased yield stability under drought conditions, and/or increased drought tolerance, said method comprising: detecting, in said maize plant or maize plant part, the presence of at least one genetic marker associated with increased yield under non-drought conditions, increased yield stability under drought conditions, and/or increased drought tolerance in a maize plant, as described herein. In further embodiments, said at least one marker can comprise, consist essentially of or consist of any marker linked to the aforementioned genetic markers. That is, any genetic marker that is in linkage disequilibrium with any of the aforementioned markers (SNPs, chromosome intervals and/or combinations of markers (haplotypes)) may also be used to identify, select and/or produce a maize plant having increased yield under non-drought conditions, increased yield stability under drought conditions, and/or increased drought tolerance. Linked markers may be determined, for example, by using resources available on the MaizeGDB website (maizegdb.org), Maize Sequence (ensembl.gramene.org), Phytozome v9.1: Zea mays (phytozome.net/maize.php).

The present invention further provides that the detecting of a genetic marker can comprise the use of a nucleic acid probe having a nucleotide base sequence that is substantially complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% complementary) to a nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a marker is designed to determine whether a particular allele of a SNP is present or absent in a particular plant.

Additionally, the methods of this invention include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length based on a similar reaction with the same primers with the DNA from the plant in which the marker was first detected or the nucleic acid sequence that corresponds (e.g., a homology of at least about 80%, 81%, 82%, 83%, 84%, 85%, 86%, 87%, 88%, 89%, 90%, 91%, 92%, 93%, 94%, 95%, 96%, 97%, 98%, 99% or more) to the expected sequence based on the sequence of the marker associated with that SNP in the plant in which the marker was first detected.

The detecting of an amplified DNA fragment having the predicted length or the predicted nucleic acid sequence can be performed by any of a number or techniques, including, but not limited to, standard gel-electrophoresis techniques or by using automated DNA sequencers. Such methods of detecting an amplified DNA fragment are not described here in detail as they are well known to those of ordinary skill in the art.

As shown in Table 1, the SNP markers of this invention are associated with increased yield under non-drought conditions, increased yield stability under drought conditions, and/or increased drought tolerance. In some embodiments, as described herein, one marker or a combination of markers can be used to detect the presence of a maize plant having increased yield under non-drought conditions, increased yield stability under drought conditions, and/or increased drought tolerance. In some embodiments, a marker can be located within a chromosomal interval (QTL) or be present in the genome of the plant as a haplotype as defined herein.

Thus, methods for identifying and/or selecting a maize plant or germplasm having increased yield under non-drought conditions, increased yield stability under drought conditions, and/or increased drought tolerance comprise detecting the presence of a genetic marker (e.g., SNP, SNP located in chromosomal interval (QTL) and/or combination of SNPs) associated with increased yield under non-drought conditions, increased yield stability under drought conditions, and/or increased drought tolerance in a maize plant or part thereof. The genetic marker can be detected in any sample taken from, for example, a maize plant or from a maize germplasm, including, but not limited to, the whole plant or germplasm or any part thereof (e.g., a seed, a leaf, a tissue culture, a cell, etc.).

Accordingly, in some aspects of the present invention, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; and (ccc) any combination of (a) to (bbb) above, thereby identifying and/or selecting a maize plant or maize plant part having increased yield under non-drought conditions, increased yield stability under drought conditions, and/or increased drought tolerance as compared to a control maize plant.

In some embodiments, an allele is detected at the base pair positions of the chromosome intervals described herein, wherein said allele comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 10 defined by and including a G or GG allele at base pair (bp) position 14762443 and a C or CC allele at base pair (bp) position 14765098; a G or GG allele at base pair (bp) position 14762443 and an A or AA allele at base pair (bp) position 14765012; a G or GG allele at base pair (bp) position 14762443 and an A or AA allele at base pair (bp) position 14764839; a G or GG allele at base pair (bp) position 14762443 and a G or GG allele at base pair (bp) position 14764763; a G or GG allele at base pair (bp) position 14762443 and a C or CC allele at base pair (bp) position 14764762; a G or GG allele at base pair (bp) position 14762443 and a G or GG allele at base pair (bp) position 14764658; a G or GG allele at base pair (bp) position 14762443 and a G or GG allele at base pair (bp) position 14764415; a G or GG allele at base pair (bp) position 14764415 and a C or CC allele at base pair (bp) position 14765098; a G or GG allele at base pair (bp) position 14764415 and an A or AA allele at base pair (bp) position 14765012; a G or GG allele at base pair (bp) position 14764415 and an A allele at base pair (bp) position 14764839; a G or GG allele at base pair (bp) position 14764415 and a G allele at base pair (bp) position 14764763; a G or GG allele at base pair (bp) position 14764415 and a C or CC allele at base pair (bp) position 14764762; a G or GG allele at base pair (bp) position 14764415 and a G or GG allele at base pair (bp) position 14764658; a G or GG allele at base pair (bp) position 14764658 and a C allele at base pair (bp) position 14765098; a G or GG allele at base pair (bp) position 14764658 and an A or AA allele at base pair (bp) position 14765012; a G or GG allele at base pair (bp) position 14764658 and an A or AA allele at base pair (bp) position 14764839; a G or GG allele at base pair (bp) position 14764658 and a G or GG allele at base pair (bp) position 14764763; a G or GG allele at base pair (bp) position 14764658 and a C or CC allele at base pair (bp) position 14764762; a C or CC allele at base pair (bp) position 14764762 and a C or CC allele at base pair (bp) position 14765098; a C or CC allele at base pair (bp) position 14764762 and an A or AA allele at base pair (bp) position 14765012; a C or CC allele at base pair (bp) position 14764762 and an A or AA allele at base pair (bp) position 14764839; a C or CC allele at base pair (bp) position 14764762 and a G or GG allele at base pair (bp) position 14764763; a G or GG allele at base pair (bp) position 14764763 and a C or CC allele at base pair (bp) position 14765098; G or GG allele at base pair (bp) position 14764763 and an A or AA allele at base pair (bp) position 14765012; a G or GG allele at base pair (bp) position 14764763 and an A or AA allele at base pair (bp) position 14764839; an A or AA allele at base pair (bp) position 14764839 and a C or CC allele at base pair (bp) position 14765098; an A or AA allele at base pair (bp) position 14764839 and an A or AA allele at base pair (bp) position 14765012 or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 3 defined by and including a G or GG allele at base pair (bp) position 171748815 and a C or CC allele at base pair (bp) position 171752467; a G or GG allele at base pair (bp) position 171748815 and a G or GG allele at base pair (bp) position 171752311; a G or GG allele at base pair (bp) position 171748815 and a C or CC allele at base pair (bp) position 171749536; a G or GG allele at base pair (bp) position 171748815 and an A or AA allele at base pair (bp) position 171749318; a G or GG allele at base pair (bp) position 171748815 and an A or AA allele at base pair (bp) position 171749283; a G or GG allele at base pair (bp) position 171748815 and a C or CC allele at base pair (bp) position 171749273; a C or CC allele at base pair (bp) position 171749273 and a C or CC allele at base pair (bp) position 171752467; a C or CC allele at base pair (bp) position 171749273 and a G or GG allele at base pair (bp) position 171752311; a C or CC allele at base pair (bp) position 171749273 and a C or CC allele at base pair (bp) position 171749536; a C or CC allele at base pair (bp) position 171749273 and an A or AA allele at base pair (bp) position 171749318; a C or CC allele at base pair (bp) position 171749273 and an A or AA allele at base pair (bp) position 171749283; an A or AA allele at base pair (bp) position 171749283 and a C or CC allele at base pair (bp) position 171752467; an A or AA allele at base pair (bp) position 171749283 a G or GG allele at base pair (bp) position 171752311; an A or AA allele at base pair (bp) position 171749283 and a C or CC allele at base pair (bp) position 171749536; an A or AA allele at base pair (bp) position 171749283 and an A or AA allele at base pair (bp) position 171749318; an A or AA allele at base pair (bp) position 171749318 and a C or CC allele at base pair (bp) position 171752467; an A or AA allele at base pair (bp) position 171749318 and a G or GG allele at base pair (bp) position 171752311; an A or AA allele at base pair (bp) position 171749318 and a C or CC allele at base pair (bp) position 171749536; a C or CC allele at base pair (bp) position 171749536 and a C or CC allele at base pair (bp) position 171752467; a C or CC allele at base pair (bp) position 171749536 and a G or GG allele at base pair (bp) position 171752311; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 1 defined by and including an A or an AA allele at base pair (bp) position 194932443 and a T or TT allele at base pair (bp) position 194935353, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 8 defined by and including a C or CC allele at base pair (bp) position 33363546 and an A or AA allele at base pair (bp) position 33368983; a C or CC llele at base pair (bp) position 33363546 and a T or TT allele at base pair (bp) position 33363625; a T or TT allele at base pair (bp) position 33363625 and an A or AA allele at base pair (bp) position 33368983; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in said maize plant or maize plant part, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 5 defined by and including a C or CC allele at base pair (bp) position 164854921 and a G or GG allele at base pair (bp) position 164858109; a C or CC allele at base pair (bp) position 164854921 and an A or AA allele at base pair (bp) position 164855482; an A or AA allele at base pair (bp) position 164855482 and a G or GG allele at base pair (bp) position 164858109; or any combination thereof, thereby identifying and/or selecting a maize plant or maize plant part having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, detecting can comprise detecting any combination of markers associated with increased yield under non-drought conditions, increased yield stability under drought conditions, and/or increased drought tolerance in maize as defined herein. Thus, the combination of markers can be any combination of those identified on chromosome 3, those identified on chromosome 10, those identified on chromosome 1, those identified on chromosome 8, or those identified on chromosome 5. Thus, in some embodiments, a method of identifying and/or selecting a maize plant or maize plant part having increased yield under non-drought conditions, increased yield stability under drought conditions, and/or increased drought tolerance is provided, comprising: detecting, in a maize plant or maize plant part, the presence of a combination of markers associated with increased yield under non-drought conditions, increased yield stability under drought conditions, and/or increased drought tolerance in a maize plant, wherein said combination of markers comprises, consists essentially of, or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above, thereby identifying and/or selecting a maize plant or maize plant part having increased yield under non-drought conditions, increased yield stability under drought conditions, and/or increased drought tolerance. In some embodiments, the alleles at the base pair positions defined herein can be independently heterozygous or homozygous.

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of an allele of at least one marker locus associated with increased yield position 33363625; a C or CC at base pair (bp) position 164854921; a G or CC at base pair (bp) position 164858109; an AA at base pair (bp) position 164855482, or any combination thereof.

TABLE 3

| a. Significant Insertion/Deletion Markers from FBAM Study | | | | |
|---|---|---|---|---|
| INDEL | Analysis_ID | Trait | Marker | GeneModelID |
| 1 | Sweet_SS_K_1PC | YGSMN_2008_irrigated | chr3_171748915_A_AGA | GRMZM2G039365 |
| 2 | Sweet_NSS_K_6PC | YGSMN_2009_irrigated | chr10_14764880_GCATG_G | GRMZM2G173669 |

| b. Significant Insertion/Deletion Markers from FBAM Study | | | | | | | | |
|---|---|---|---|---|---|---|---|---|
| INDEL | Chrom. | Site | NegLogP | Num_Ind | Allele_1 | Allele1_effect | Allele_2 | Allele2_effect |
| 1 | chr3 | 171748915 | 3.6662304 | 142 | D | 2.1373275 | I | −2.1373275 |
| 2 | chr10 | 14764880 | 3.5313721 | 229 | D | −2.11413 | I | 2.11413 | under non-drought conditions, increased yield stability under drought conditions and/or increased drought tolerance in a maize plant, wherein said allele of at least one marker locus comprises, consists essentially of, or consists of: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; or any combination thereof, thereby identifying and/or selecting a maize plant or maize plant part having increased yield under non-drought conditions, increased yield stability under drought conditions, and/or increased drought tolerance. In some embodiments, the marker alleles can be independently heterozygous or homozygous.

In representative embodiments, the detecting, in said maize plant or maize plant part, comprises, consists essentially of, or consists of detecting the presence of: a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp)

In some embodiments, a method of identifying and/or selecting a maize plant or maize plant part having increased yield under non-drought conditions, increased yield stability under drought conditions, and/or increased drought tolerance is provided, the method comprising: detecting, in a maize plant or maize plant part, the presence of an allele of at least one marker locus associated with increased yield under non-drought conditions, increased yield stability under drought conditions and/or increased drought tolerance in a maize plant, wherein said allele of at least one marker locus is selected from the group comprised of INDEL 1 and INDEL2 found in Table 3.

Thus, as described herein, methods for identifying and/or selecting a maize plant or maize plant part having increased yield under non-drought conditions, increased yield stability under drought conditions, and/or increased drought tolerance can comprise detecting the presence of a marker or a combination of markers associated with increased yield under non-drought conditions, increased yield stability under drought conditions, and/or increased drought tolerance in a maize plant as defined herein. Any combination of genetic markers of this invention can be used to identify and/or select a maize plant or germplasm having increased yield under non-drought conditions, increased yield stability under drought conditions, and/or increased drought tolerance.

The subject matter disclosed herein also relates to methods for producing maize plants comprising detecting the presence of a marker allele or a locus associated with increased yield under non-drought conditions, increased yield stability under drought conditions, and/or increased drought tolerance in a donor maize plant according to the methods described herein and transferring a nucleic acid sequence comprising at least one allele thus detected from the donor plant to a maize plant not having increased yield under non-drought conditions, increased yield stability under drought conditions, and/or increased drought tolerance. The transfer of the nucleic acid sequence can be performed by any known or later developed methods for transferring genetic material between plants.

Thus, the present invention encompasses methods of plant breeding and methods of selecting/identifying plants, in particular maize plants, particularly cultivated maize plants as breeder plants for use in breeding programs or cultivated maize plants having desired genotypic or potential phenotypic properties, in particular related to producing valuable maize plants, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example, a plant obtained by inbreeding.

The presently disclosed subject matter thus also provides methods for selecting a plant of the species *Zea mays* exhibiting increased yield under non-drought conditions, increased yield stability under drought conditions, and/or increased drought tolerance, the methods comprising detecting in the plant the presence of one or more genetic markers associated with increased yield under non-drought conditions, increased yield stability under drought conditions, and/or increased drought tolerance as defined herein. In an exemplary embodiment, a method for selecting such a plant comprises providing a sample of genomic DNA from a maize plant or maize plant part; and detecting in the sample of genomic DNA at least one genetic marker associated with increased yield under non-drought conditions, increased yield stability under drought conditions, and/or increased drought tolerance as described herein. In some embodiments, the detecting can comprise detecting one or more SNPs, a combination of SNPs (haplotype), and/or SNPs located in chromosomal intervals that are associated with increased yield under non-drought conditions, increased yield stability under drought conditions, and/or increased drought tolerance in a maize plant.

The providing of a sample of genomic DNA from a maize plant can be performed by standard DNA isolation methods well known in the art.

As is well known in the art, the detecting of a genetic marker can in some embodiments comprise the use of one or more sets of primer pairs that can be used to produce one or more amplification products that are suitable for identifying, for example, a SNP. Primer pairs can be readily prepared using the nucleotide sequences of SEQ ID NO:1, SEQ ID NO:2, SEQ ID NO:3, SEQ ID NO:4, and/or SEQ ID NO:5, and the positions and alleles of the markers as provided herein.

In some embodiments of this invention, a method is provided, said method comprising transfer by introgression of the nucleic acid sequence conferring increased yield under non-drought conditions, increased yield stability under drought conditions, and/or increased drought tolerance from a donor maize plant into a recipient maize plant by crossing the plants. This transfer can be accomplished by using traditional breeding techniques. Loci associated with increased yield under non-drought conditions, increased yield stability under drought conditions, and/or increased drought tolerance in maize plants are introgressed in some embodiments into commercial corn varieties using marker-assisted selection (MAS) or marker-assisted breeding (MAB). MAS and MAB involves the use of one or more of the molecular markers, identified as having a significant likelihood of co-segregation with a desired trait, and used for the identification and selection of those offspring plants that contain one or more of the genes that encode the desired trait. As disclosed herein, such identification and selection is based on selection of one or more SNP alleles of this invention or markers associated therewith. MAB can also be used to develop near-isogenic lines (NIL) harboring one or more alleles of interest associated with increased yield under non-drought conditions, increased yield stability under drought conditions, and/or increased drought tolerance in a maize plant, allowing a more detailed study of an effect of such allele(s), and is also an effective method for development of backcross inbred line (BIL) populations. Maize plants developed according to these embodiments can in some embodiments derive a majority of their traits from the recipient plant and derive increased yield under non-drought conditions, increased yield stability under drought conditions, and/or increased drought tolerance from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with increased yield under non-drought conditions, increased yield stability under drought conditions, and/or increased drought tolerance into a recipient maize plant not having increased yield under non-drought conditions, increased yield stability under drought conditions, and/or increased drought tolerance. For example, inbred maize lines having increased yield under non-drought conditions, increased yield stability under drought conditions, and/or increased drought tolerance can be developed using the techniques of recurrent selection and backcrossing, selfing, and/or dihaploids, or any other technique used to make parental lines. In a method of recurrent selection and backcrossing, increased yield under non-drought conditions, increased yield stability under drought conditions, and/or increased drought tolerance can be introgressed into a target recipient plant (the recurrent parent) by crossing the recurrent parent with a first donor plant, which differs from the recurrent parent and is referred to herein as the "non-recurrent parent." The recurrent parent can be a plant that does not exhibit or exhibits a low level of increased yield under non-drought conditions, increased yield stability under drought conditions, and/or increased drought toleranc, but which, in some embodiments, comprises commercially desirable characteristics, such as, but not limited to disease and/or insect resistance, valuable nutritional characteristics, valuable additional abiotic stress tolerance (including, but not limited to, additional drought tolerance, salt tolerance), and the like. In some embodiments, the non-recurrent parent exhibits increased yield under non-drought conditions, increased yield stability under drought conditions, and/or increased drought tolerance and comprises a nucleic acid sequence that is associated with increased yield under non-drought conditions, increased yield stability under drought conditions, and/or increased drought tolerance. The non-recurrent parent can be any maize variety or inbred line that is cross-fertile with the recurrent parent. In some embodiments, a recurrent parent plant can be the control plant against which increased yield under non-drought conditions, increased yield stability under drought conditions, and/or increased drought tolerance can be measured.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as are known in the art. Alternatively, instead of using bioassays, MAB can be performed using one or more of the hereinbefore described molecular markers, hybridization probes, or polynucleotides to identify those progeny that comprise a nucleic acid sequence associated with increased yield under non-drought conditions, increased yield stability under drought conditions, and/or increased drought tolerance. Also, MAB can be used to confirm the results obtained from the quantitative bioassays. In some embodiments, the markers defined herein are suitable to select proper offspring plants by genotypic screening.

Following screening, the F1 hybrid plants that exhibit a phenotype of increased yield under non-drought conditions, increased yield stability under drought conditions, and/or increased drought tolerance or, in some embodiments, the genotype, and thus comprise the requisite nucleic acid sequence associated with increased yield under non-drought conditions, increased yield stability under drought conditions, and/or increased drought tolerance, can then be selected and backcrossed to the recurrent parent for one or more generations in order to allow for the maize plant to become increasingly inbred. This process can be performed for one, two, three, four, five, six, seven, eight, or more generations.

Thus, a marker that demonstrates linkage with a locus affecting a desired phenotypic trait provides a useful tool for selection of the trait in a plant population. This is particularly true where the phenotype may be difficult to assay or occurs at a late stage in plant development. Since DNA marker assays are less laborious and take up less physical space than field phenotyping, much larger populations can be assayed, increasing the chances of finding a recombinant plant with the target segment moved from the donor line to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

The availability of integrated linkage maps of the maize genome containing increasing densities of public maize markers has facilitated maize genetic mapping and MAS. See, e.g. MaizeGDB (maizegdb.org/map.php).

Of all the molecular marker types, SNPs are the most abundant and have the potential to provide the highest genetic map resolution (Bhattramakki et al., *Plant Molec. Biol.* 48:539 (2002)). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

Accordingly, the markers of the present invention can be used in marker-assisted selection methods to identify and/or select and/or produce progeny having a genetic marker associated with increased yield under non-drought conditions, increased yield stability under drought conditions, and/or increased drought tolerance in maize. Thus, in some embodiments, the present invention relates to methods for producing maize plants comprising an allele associated with increased yield under non-drought conditions, increased yield stability under drought conditions, and/or increased drought tolerance, comprising detecting the presence of at least one allele associated with increased yield under non-drought conditions, increased yield stability under drought conditions, and/or increased drought tolerance in a donor maize plant as described herein, crossing the donor maize plant with a second maize plant or germplasm, and detecting in the progeny plant(s) the presence of said at least one allele associated with increased yield under non-drought conditions, increased yield stability under drought conditions, and/or increased drought tolerance, thereby transferring the at least one allele associated with increased yield under non-drought conditions, increased yield stability under drought conditions, and/or increased drought tolerance thus detected from the donor maize plant to the second maize plant and producing a maize plant (e.g., progeny plant) having increased yield under non-drought conditions, increased yield stability under drought conditions, and/or increased drought tolerance. In some embodiments, the second maize plant does not comprise increased yield under non-drought conditions, increased yield stability under drought conditions, and/or increased drought tolerance. The transfer of the allele associated with increased yield under non-drought conditions, increased yield stability under drought conditions, and/or increased drought tolerance can be performed by any of the methods described herein.

Thus, in some embodiments, a method of producing a maize plant having increased yield under non-drought conditions, increased yield stability under drought conditions, and/or increased drought tolerance is provided, the method comprising: detecting, in a maize plant, at least one a marker locus that is associated with increased yield under non-drought conditions, increased yield stability under drought conditions, and/or increased drought tolerance, wherein said at least one marker locus is located within a chromosomal interval comprising, consisting essentially of, or consisting of: (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283;

(mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above, thereby producing a plant having increased yield under non-drought conditions, increased yield stability under drought conditions, and/or increased drought tolerance as compared to a control maize plant.

In some embodiments, an allele is detected at the base pair positions of the chromosome intervals described herein, wherein said allele comprises, consists essentially of, or consists of: a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 10 defined by and including a G or GG allele at base pair (bp) position 14762443 and a C or CC allele at base pair (bp) position 14765098; a G or GG allele at base pair (bp) position 14762443 and an A or AA allele at base pair (bp) position 14765012; a G or GG allele at base pair (bp) position 14762443 and an A or AA allele at base pair (bp) position 14764839; a G or GG allele at base pair (bp) position 14762443 and a G or GG allele at base pair (bp) position 14764763; a G or GG allele at base pair (bp) position 14762443 and a C or CC allele at base pair (bp) position 14764762; a G or GG allele at base pair (bp) position 14762443 and a G or GG allele at base pair (bp) position 14764658; a G or GG allele at base pair (bp) position 14762443 and a G or GG allele at base pair (bp) position 14764415; a G or GG allele at base pair (bp) position 14764415 and a C or CC allele at base pair (bp) position 14765098; a G or GG allele at base pair (bp) position 14764415 and an A or AA allele at base pair (bp) position 14765012; a G or GG allele at base pair (bp) position 14764415 and an A allele at base pair (bp) position 14764839; a G or GG allele at base pair (bp) position 14764415 and a G allele at base pair (bp) position 14764763; a G or GG allele at base pair (bp) position 14764415 and a C or CC allele at base pair (bp) position 14764762; a G or GG allele at base pair (bp) position 14764415 and a G or GG allele at base pair (bp) position 14764658; a G or GG allele at base pair (bp) position 14764658 and a C allele at base pair (bp) position 14765098; a G or GG allele at base pair (bp) position 14764658 and an A or AA allele at base pair (bp) position 14765012; a G or GG allele at base pair (bp) position 14764658 and an A or AA allele at base pair (bp) position 14764839; a G or GG allele at base pair (bp) position 14764658 and a G or GG allele at base pair (bp) position 14764763; a G or GG allele at base pair (bp) position 14764658 and a C or CC allele at base pair (bp) position 14764762; a C or CC allele at base pair (bp) position 14764762 and a C or CC allele at base pair (bp) position 14765098; a C or CC allele at base pair (bp) position 14764762 and an A or AA allele at base pair (bp) position 14765012; a C or CC allele at base pair (bp) position 14764762 and an A or AA allele at base pair (bp) position 14764839; a C or CC allele at base pair (bp) position 14764762 and a G or GG allele at base pair (bp) position 14764763; a G or GG allele at base pair (bp) position 14764763 and a C or CC allele at base pair (bp) position 14765098; G or GG allele at base pair (bp) position 14764763 and an A or AA allele at base pair (bp) position 14765012; a G or GG allele at base pair (bp) position 14764763 and an A or AA allele at base pair (bp) position 14764839; an A or AA allele at base pair (bp) position 14764839 and a C or CC allele at base pair (bp) position 14765098; an A or AA allele at base pair (bp) position 14764839 and an A or AA allele at base pair (bp) position 14765012, or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 3 defined by and including a G or GG allele at base pair (bp) position 171748815 and a C or CC allele at base pair (bp) position 171752467; a G or GG allele at base pair (bp) position 171748815 and a G or GG allele at base pair (bp) position 171752311; a G or GG allele at base pair (bp) position 171748815 and a C or CC allele at base pair (bp) position 171749536; a G or GG allele at base pair (bp) position 171748815 and an A or AA allele at base pair (bp) position 171749318; a G or GG allele at base pair (bp) position 171748815 and an A or AA allele at base pair (bp) position 171749283; a G or GG allele at base pair (bp) position 171748815 and a C or CC allele at base pair (bp) position 171749273; a C or CC allele at base pair (bp) position 171749273 and a C or CC allele at base pair (bp) position 171752467; a C or CC allele at base pair (bp) position 171749273 and a G or GG allele at base pair (bp) position 171752311; a C or CC allele at base pair (bp) position 171749273 and a C or CC allele at base pair (bp) position 171749536; a C or CC allele at base pair (bp) position 171749273 and an A or AA allele at base pair (bp) position 171749318; a C or CC allele at base pair (bp) position 171749273 and an A or AA allele at base pair (bp) position 171749283; an A or AA allele at base pair (bp) position 171749283 and a C or CC allele at base pair (bp) position 171752467; an A or AA allele at base pair (bp) position 171749283 a G or GG allele at base pair (bp) position 171752311; an A or AA allele at base pair (bp) position 171749283 and a C or CC allele at base pair (bp) position 171749536; an A or AA allele at base pair (bp) position 171749283 and an A or AA allele at base pair (bp) position 171749318; an A or AA allele at base pair (bp) position 171749318 and a C or CC allele at base pair (bp) position 171752467; an A or AA allele at base pair (bp) position 171749318 and a G or GG allele at base pair (bp) position 171752311; an A or AA allele at base pair (bp) position 171749318 and a C or CC allele at base pair (bp) position 171749536; a C or CC allele at base pair (bp) position 171749536 and a C or CC allele at base pair (bp) position 171752467; a C or CC allele at base pair (bp) position 171749536 and a G or GG allele at base pair (bp) position 171752311; or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 1 defined by and including an A or an AA allele at base pair (bp) position 194932443 and a T or TT allele at base pair (bp) position 194935353, thereby identifying and/or selecting a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 8 defined by and including a C or CC allele at base pair (bp) position 33363546 and an A or AA allele at base pair (bp) position 33368983; a C or CC llele at base pair (bp) position 33363546 and a T or TT allele at base pair (bp) position 33363625; a T or TT allele at base pair (bp) position 33363625 and an A or AA allele at base pair (bp) position 33368983; or any combination thereof, thereby producing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of a marker associated with increased yield under non-drought conditions, increased yield stability under drought conditions, and/or increased drought tolerance in a maize plant, wherein said marker is located within a chromosomal interval comprising, consisting essentially of, or consisting of: a chromosomal interval on chromosome 5 defined by and including a C or CC allele at base pair (bp) position 164854921 and a G or GG allele at base pair (bp) position 164858109; a C or CC allele at base pair (bp) position 164854921 and an A or AA allele at base pair (bp) position 164855482; an A or AA allele at base pair (bp) position 164855482 and a G or GG allele at base pair (bp) position 164858109; or any combination thereof, thereby providing a maize plant having increased yield under non-drought conditions, increased yield stability under drought conditions, and/or increased drought tolerance as compared to a control maize plant. In some embodiments, the alleles defining the chromosome intervals can be independently heterozygous or homozygous.

In some embodiments, detecting can comprise detecting one or more markers associated with increased yield under non-drought conditions, increased yield stability under drought conditions, and/or increased drought tolerance in maize as defined herein, in any combination. Thus, a combination of markers for detection can be any combination of markers identified on chromosome 3, markers identified on chromosome 10, markers identified on chromosome 1, markers identified on chromosome 8, and/or markers identified on chromosome 5. Thus, in some embodiments, a method of providing a maize plant having increased yield under non-drought conditions, increased yield stability under drought conditions, and/or increased drought tolerance is provided, comprising: detecting, in a maize plant, the presence of a combination of markers associated with increased yield under non-drought conditions, increased yield stability under drought conditions, and/or increased drought tolerance in a maize plant, wherein said combination of markers comprises, consists essentially of, or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625; (yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above, thereby producing a maize plant having increased yield under non-drought conditions, increased yield stability under drought conditions, and/or increased drought tolerance. In some embodiments, the alleles at the base pair positions defined herein can be independently heterozygous or homozygous.

In some embodiments, a method of producing a maize plant having increased yield under non-drought conditions, increased yield stability under drought conditions, and/or increased drought tolerance is provided, the method comprising: detecting, in a maize plant, the presence of an allele of at least one marker locus associated with increased yield under non-drought conditions, increased yield stability under drought conditions and/or increased drought tolerance in a maize plant, wherein said allele of at least one marker locus comprises, consists essentially of, or consists of: a G allele at base pair (bp) position 14762443; a C allele at base pair (bp) position 14765098; an A allele at base pair (bp) position 14765012; an A allele at base pair (bp) position 14764839; a G allele at base pair (bp) position 14764763; a C allele at base pair (bp) position 14764762; a G allele at base pair (bp) position 14764658; a G allele at base pair (bp) position 14764415; a G allele at base pair (bp) position 171748815; a C allele at base pair (bp) position 171752467; a G allele at base pair (bp) position 171752311; a C allele at base pair (bp) position 171749536; an A allele at base pair (bp) position 171749318; an A allele at base pair (bp) position 171749283; a C allele at base pair (bp) position 171749273; an A allele at base pair (bp) position 194932443; a T allele at base pair (bp) position 194935353; a C allele at base pair (bp) position 33363546; an A allele at base pair (bp) position 33368983; a T allele at base pair (bp) position 33363625; a C allele at base pair (bp) position 164854921; a G allele at base pair (bp) position 164858109; an A allele at base pair (bp) position 164855482; or any combination thereof, thereby producing a maize plant having increased yield under non-drought conditions, increased yield stability under drought conditions, and/or increased drought tolerance. In some embodiments, the alleles of the markers can be independently heterozygous or homozygous.

In representative embodiments, the detecting, in said maize plant, comprises, consists essentially of, or consists of detecting the presence of: a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482, or any combination thereof.

In some embodiments, in the methods of producing a maize plant having increased yield under non-drought conditions, increased yield stability under drought conditions, and/or increased drought tolerance, the detecting can comprise detecting markers in a maize plant part, plant cell or plant germplasm, wherein said maize plant part, plant cell or plant germplasm in which said marker(s) is/are detected can be regenerated into a maize plant, thereby producing a maize plant having increased yield under non-drought conditions, increased yield stability under drought conditions, and/or increased drought tolerance as compared to a control maize plant.

In some embodiments, a method of selecting a maize plant or germplasm having increased yield under non-drought conditions, increased yield stability under drought conditions, and/or increased drought tolerance is provided, comprising: crossing a first maize plant or germplasm with a second maize plant or germplasm, wherein said first maize plant or germplasm comprises within its genome at least one marker associated with increased yield under non-drought conditions, increased yield stability under drought conditions, and/or increased drought tolerance in a maize plant, wherein said marker is located within a chromosomal interval comprising, consisting essentially of, or consisting of:

(a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp) position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp)

position 164855482 to base pair (bp) position 164858109; or (ccc) any combination of (a) to (bbb) above, and selecting a progeny maize plant or germplasm that comprises said at least one marker within its genome, thereby selecting a maize plant or germplasm having increased yield under non-drought conditions, increased yield stability under drought conditions, and/or increased drought tolerance.

In some embodiments, the allele at the base pair positions of said chromosome intervals comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; and/or an A or AA at base pair (bp) position 164855482. In some embodiments, the alleles defining the chromosome intervals can be independently heterozygous or homozygous.

In some embodiments, a method of selecting a maize plant or germplasm having increased yield under non-drought conditions, increased yield stability under drought conditions, and/or increased drought tolerance is provided, comprising crossing a first maize plant or germplasm with a second maize plant or germplasm, wherein said first maize plant or germplasm comprises within its genome a combination of genetic markers associated with increased yield under non-drought conditions, increased yield stability under drought conditions, and/or increased drought tolerance in a maize plant, wherein said combination of genetic markers comprises, consists essentially of or consists of: (a) a G allele at base pair (bp) position 14762443 and a C allele at base pair (bp) position 14765098; (b) a G allele at base pair (bp) position 14762443 and an A allele at base pair (bp) position 14765012; (c) a G allele at base pair (bp) position 14762443 and an A allele at base pair (bp) position 14764839; (d) a G allele at base pair (bp) position 14762443 and a G allele at base pair (bp) position 14764763; (e) a G allele at base pair (bp) position 14762443 and a C allele at base pair (bp) position 14764762; (f) a G allele at base pair (bp) position 14762443 and a G allele at base pair (bp) position 14764658; (g) a G allele at base pair (bp) position 14762443 and a G allele at base pair (bp) position 14764415; (h) a G allele at base pair (bp) position 14764415 and a C allele at base pair (bp) position 14765098; (i) a G allele at base pair (bp) position 14764415 and an A allele at base pair (bp) position 14765012; (j) a G allele at base pair (bp) position 14764415 and an A allele at base pair (bp) position 14764839; (k) a G allele at base pair (bp) position 14764415 and a G allele at base pair (bp) position 14764763; (l) a G allele at base pair (bp) position 14764415 and a C allele at base pair (bp) position 14764762; (m) a G allele at base pair (bp) position 14764415 and a G allele at base pair (bp) position 14764658; (n) a G allele at base pair (bp) position 14764658 and a C allele at base pair (bp) position 14765098; (o) a G allele at base pair (bp) position 14764658 and an A allele at base pair (bp) position 14765012; (p) a G allele at base pair (bp) position 14764658 and an A allele at base pair (bp) position 14764839; (q) a G allele at base pair (bp) position 14764658 and a G allele at base pair (bp) position 14764763; (r) a G allele at base pair (bp) position 14764658 and a C allele at base pair (bp) position 14764762; (s) a C allele at base pair (bp) position 14764762 and a C allele at base pair (bp) position 14765098; (t) a C allele at base pair (bp) position 14764762 and an A allele at base pair (bp) position 14765012; (u) a C allele at base pair (bp) position 14764762 and an A allele at base pair (bp) position 14764839; (v) a C allele at base pair (bp) position 14764762 and a G allele at base pair (bp) position 14764763; (w) a G allele at base pair (bp) position 14764763 and a C allele at base pair (bp) position 14765098; (x) a G allele at base pair (bp) position 14764763 and an A allele at base pair (bp) position 14765012; (y) a G allele at base pair (bp) position 14764763 and an A allele at base pair (bp) position 14764839; (z) an A allele at base pair (bp) position 14764839 and a C allele at base pair (bp) position 14765098; (aa) an A allele at base pair (bp) position 14764839 and an A allele at base pair (bp) position 14765012; (bb) a G allele at base pair (bp) position 171748815 and a C allele at base pair (bp) position 171752467; (cc) a G allele at base pair (bp) position 171748815 and a G allele at base pair (bp) position 171752311; (dd) a G allele at base pair (bp) position 171748815 and a C allele at base pair (bp) position 171749536; (ee) a G allele at base pair (bp) position 171748815 and an A allele at base pair (bp) position 171749318; (ff) a G allele at base pair (bp) position 171748815 and an A allele at base pair (bp) position 171749283; (gg) a G allele at base pair (bp) position 171748815 and a C allele at base pair (bp) position 171749273; (hh) a C allele at base pair (bp) position 171749273 and a C allele at base pair (bp) position 171752467; (ii) a C allele at base pair (bp) position 171749273 and a G allele at base pair (bp) position 171752311; (jj) a C allele at base pair (bp) position 171749273 and a C allele at base pair (bp) position 171749536; (kk) a C allele at base pair (bp) position 171749273 and an A allele at base pair (bp) position 171749318; (ll) a C allele at base pair (bp) position 171749273 and an A allele at base pair (bp) position 171749283; (mm) an A allele at base pair (bp) position 171749283 and a C allele at base pair (bp) position 171752467; (nn) an A allele at base pair (bp) position 171749283 a G allele at base pair (bp) position 171752311; (oo) an A allele at base pair (bp) position 171749283 and a C allele at base pair (bp) position 171749536; (pp) an A allele at base pair (bp) position 171749283 and an A allele at base pair (bp) position 171749318; (qq) an A allele at base pair (bp) position 171749318 and a C allele at base pair (bp) position 171752467; (rr) an A allele at base pair (bp) position 171749318 and a G allele at base pair (bp) position 171752311; (ss) an A allele at base pair (bp) position 171749318 and a C allele at base pair (bp) position 171749536; (tt) a C allele at base pair (bp) position 171749536 and a C allele at base pair (bp) position 171752467; (uu) a C allele at base pair (bp) position 171749536 and a G allele at base pair (bp) position 171752311; (vv) an A allele at base pair (bp) position 194932443 and a T allele at base pair (bp) position 194935353; (ww) a C allele at base pair (bp) position 33363546 and an A allele at base pair (bp) position 33368983; (xx) a C allele at base pair (bp) position 33363546 and a T allele at base pair (bp) position 33363625;

(yy) a T allele at base pair (bp) position 33363625 and an A allele at base pair (bp) position 33368983; (zz) a C allele at base pair (bp) position 164854921 and a G allele at base pair (bp) position 164858109; (aaa) a C allele at base pair (bp) position 164854921 and an A allele at base pair (bp) position 164855482; (bbb) an A allele at base pair (bp) position 164855482 and a G allele at base pair (bp) position 164858109; or (ccc) any combination of (a) to (bbb) above; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions defined herein can be independently heterozygous or homozygous.

In some embodiments, a method of selecting a maize plant or germplasm having increased yield under non-drought conditions, increased yield stability under drought conditions, and/or increased drought tolerance is provided, comprising: crossing a first maize plant or germplasm with a second maize plant or germplasm, wherein said first maize plant or germplasm comprises within its genome a genetic marker associated with increased yield under non-drought conditions, increased yield stability under drought conditions, and/or increased drought tolerance in a maize plant, wherein said genetic marker comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311; a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; an A or AA at base pair (bp) position 164855482; and/or any combination thereof; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions as defined herein can be independently heterozygous or homozygous.

In representative embodiments, said genetic marker comprises, consists essentially of, or consists of a G or GG at base pair (bp) position 14762443; a C or CC at base pair (bp) position 14765098; an AA at base pair (bp) position 14765012; an AA at base pair (bp) position 14764839; a GG at base pair (bp) position 14764763; a CC at base pair (bp) position 14764762; a GG at base pair (bp) position 14764658; a GG at base pair (bp) position 14764415; a G or GG at base pair (bp) position 171748815; a C or CC at base pair (bp) position 171752467; a GG at base pair (bp) position 171752311; a CC at base pair (bp) position 171749536; an AA at base pair (bp) position 171749318; an AA at base pair (bp) position 171749283; a CC at base pair (bp) position 171749273; an AA at base pair (bp) position 194932443; a T or TT at base pair (bp) position 194935353; a C or CC at base pair (bp) position 33363546; an A or AA at base pair (bp) position 33368983; a TT at base pair (bp) position 33363625; a C or CC at base pair (bp) position 164854921; a G or CC at base pair (bp) position 164858109; an AA at base pair (bp) position 164855482; or any combination thereof.

In some embodiments, the second maize plant or germplasm of this invention is of an elite variety of maize. In some embodiments, the genome of the second maize plant or germplasm is at least about 60%, 65%, 70%, 75%, 80%, 85%, 90%, 95%, 97%, 99% or 100% identical to that of an elite variety of maize.

In some embodiments of this invention, a method of introgressing a genetic marker associated with increased yield under non-drought conditions, increased yield stability under drought conditions, and/or increased drought tolerance in maize into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with increased yield under non-drought conditions, increased yield stability under drought conditions, and/or increased drought tolerance in a maize plant, wherein said marker is located within (a) a chromosome interval on chromosome 10 defined by and including base pair (bp) position 14762443 to base pair (bp) position 14765098; (b) a chromosome interval on chromosome 10 defined by and including base pair (bp) position 14762443 to base pair (bp) position 14765012; (c) a chromosome interval on chromosome 10 defined by and including base pair (bp) position 14762443 to base pair (bp) position 14764839; (d) a chromosome interval on chromosome 10 defined by and including base pair (bp) position 14762443 to base pair (bp) position 14764763; (e) a chromosome interval on chromosome 10 defined by and including base pair (bp) position 14762443 to base pair (bp) position 14764762; (f) a chromosome interval on chromosome 10 defined by and including base pair (bp) position 14762443 to base pair (bp) position 14764658; (g) a chromosome interval on chromosome 10 defined by and including base pair (bp) position 14762443 to base pair (bp) position 14764415; (h) a chromosome interval on chromosome 10 defined by and including base pair (bp) position 14764415 to base pair (bp) position 14765098; (i) a chromosome interval on chromosome 10 defined by and including base pair (bp) position 14764415 to base pair (bp) position 14765012; (j) a chromosome interval on chromosome 10 defined by and including base pair (bp) position 14764415 to base pair (bp) position 14764839; (k) a chromosome interval on chromosome 10 defined by and including base pair (bp) position 14764415 to base pair (bp) position 14764763; (l) a chromosome interval on chromosome 10 defined by and including base pair (bp) position 14764415 to base pair (bp) position 14764762; (m) a chromosome interval on chromosome 10 defined by and including base pair (bp) position 14764415 to base pair (bp) position 14764658; (n) a chromosome interval on chromosome 10 defined by and including base pair (bp) position 14764658 to base pair (bp) position 14765098; (o) a chromosome interval on chromosome 10 defined by and including base pair (bp) position 14764658 to base pair (bp) position 14765012; (p) a chromosome interval on chromosome 10 defined by and including base pair (bp) position 14764658 to base pair (bp)

position 14764839; (q) a chromosome interval on chromosome 10 defined by and including base pair (bp) position 14764658 to base pair (bp) position 14764763; (r) a chromosome interval on chromosome 10 defined by and including base pair (bp) position 14764658 to base pair (bp) position 14764762; (s) a chromosome interval on chromosome 10 defined by and including base pair (bp) position 14764762 to base pair (bp) position 14765098; (t) a chromosome interval on chromosome 10 defined by and including base pair (bp) position 14764762 to base pair (bp) position 14765012; (u) a chromosome interval on chromosome 10 defined by and including base pair (bp) position 14764762 to base pair (bp) position 14764839; (v) a chromosome interval on chromosome 10 defined by and including base pair (bp) position 14764762 to base pair (bp) position 14764763; (w) a chromosome interval on chromosome 10 defined by and including base pair (bp) position 14764763 to base pair (bp) position 14765098; (x) a chromosome interval on chromosome 10 defined by and including base pair (bp) position 14764763 to base pair (bp) position 14765012; (y) a chromosome interval on chromosome 10 defined by and including base pair (bp) position 14764763 to base pair (bp) position 14764839; (z) a chromosome interval on chromosome 10 defined by and including base pair (bp) position 14764839 to base pair (bp) position 14765098; (aa) a chromosome interval on chromosome 10 defined by and including base pair (bp) position 14764839 to base pair (bp) position 14765012; (bb) a chromosome interval on chromosome 3 defined by and including base pair (bp) position 171748815 to base pair (bp) position 171752467; (cc) a chromosome interval on chromosome 3 defined by and including base pair (bp) position 171748815 to base pair (bp) position 171752311; (dd) a chromosome interval on chromosome 3 defined by and including base pair (bp) position 171748815 to base pair (bp) position 171749536; (ee) a chromosome interval on chromosome 3 defined by and including base pair (bp) position 171748815 to base pair (bp) position 171749318; (ff) a chromosome interval on chromosome 3 defined by and including base pair (bp) position 171748815 to base pair (bp) position 171749283; (gg) a chromosome interval on chromosome 3 defined by and including base pair (bp) position 171748815 to base pair (bp) position 171749273; (hh) a chromosome interval on chromosome 3 defined by and including base pair (bp) position 171749273 to base pair (bp) position 171752467; (ii) a chromosome interval on chromosome 3 defined by and including base pair (bp) position 171749273 to base pair (bp) position 171752311; (jj) a chromosome interval on chromosome 3 defined by and including base pair (bp) position 171749273 to base pair (bp) position 171749536; (kk) a chromosome interval on chromosome 3 defined by and including base pair (bp) position 171749273 to base pair (bp) position 171749318; (ll) a chromosome interval on chromosome 3 defined by and including base pair (bp) position 171749273 to base pair (bp) position 171749283; (mm) a chromosome interval on chromosome 3 defined by and including base pair (bp) position 171749283 to base pair (bp) position 171752467; (nn) a chromosome interval on chromosome 3 defined by and including base pair (bp) position 171749283 to base pair (bp) position 171752311; (oo) a chromosome interval on chromosome 3 defined by and including base pair (bp) position 171749283 to base pair (bp) position 171749536; (pp) a chromosome interval on chromosome 3 defined by and including base pair (bp) position 171749283 to base pair (bp) position 171749318; (qq) a chromosome interval on chromosome 3 defined by and including base pair (bp) position 171749318 to base pair (bp) position 171752467; (rr) a chromosome interval on chromosome 3 defined by and including base pair (bp) position 171749318 to base pair (bp) position 171752311; (ss) a chromosome interval on chromosome 3 defined by and including base pair (bp) position 171749318 to base pair (bp) position 171749536; (tt) a chromosome interval on chromosome 3 defined by and including base pair (bp) position 171749536 to base pair (bp) position 171752467; (uu) a chromosome interval on chromosome 3 defined by and including base pair (bp) position 171749536 to base pair (bp) position 171752311; (vv) a chromosome interval on chromosome 1 defined by and including base pair (bp) position 194932443 to base pair (bp) position 194935353; (ww) a chromosome interval on chromosome 8 defined by and including base pair (bp) position 33363546 to base pair (bp) position 33368983; (xx) a chromosome interval on chromosome 8 defined by and including base pair (bp) position 33363546 to base pair (bp) position 33363625; (yy) a chromosome interval on chromosome 8 defined by and including base pair (bp) position 33363625 to base pair (bp) position 33368983; (zz) a chromosome interval on chromosome 5 defined by and including base pair (bp) position 164854921 to base pair (bp) position 164858109; (aaa) a chromosome interval on chromosome 5 defined by and including base pair (bp) position 164854921 to base pair (bp) position 164855482; (bbb) a chromosome interval on chromosome 5 defined by and including base pair (bp) position 164855482 to base pair (bp) position 164858109; or (ccc) any combination of (a) to (bbb) above; and producing a maize plant or germplasm having increased yield under non-drought conditions, increased yield stability under drought conditions, and/or increased drought tolerance and comprising said genetic marker associated with increased yield under non-drought conditions, increased yield stability under drought conditions, and/or increased drought tolerance in the genetic background of the recurrent parent, thereby introgressing the genetic marker associated with increased yield under non-drought conditions, increased yield stability under drought conditions, and/or increased drought tolerance into a genetic background lacking said marker. In some embodiments, the base pair positions defining the chromosomal intervals can comprise alleles, which can be heterozygous or homozygous, or any combination thereof.

In some embodiments of this invention, a method of introgressing a genetic marker associated with increased yield under non-drought conditions, increased yield stability under drought conditions, and/or increased drought tolerance in maize into a genetic background lacking said marker is provided, the method comprising: crossing a donor comprising said marker with a recurrent parent that lacks said marker; and backcrossing progeny comprising said marker with the recurrent parent, wherein said progeny are identified by detecting in their genome the presence of a marker associated with increased yield under non-drought conditions, increased yield stability under drought conditions, and/or increased drought tolerance in a maize plant, wherein said marker comprises, consists essentially of, or consists of a G or GG at base pair (bp) position 14762443; a C or CC at base pair (bp) position 14765098; an A or AA at base pair (bp) position 14765012; an A or AA at base pair (bp) position 14764839; a G or GG at base pair (bp) position 14764763; a C or CC at base pair (bp) position 14764762; a G or GG at base pair (bp) position 14764658; a G or GG at base pair (bp) position 14764415; a G at base pair (bp) position 171748815; a C at base pair (bp) position 171752467; a G or GG at base pair (bp) position 171752311;

a C or CC at base pair (bp) position 171749536; an A or AA at base pair (bp) position 171749318; an A or AA at base pair (bp) position 171749283; a C or CC at base pair (bp) position 171749273; an A or AA at base pair (bp) position 194932443; a T or TT at base pair (bp) position 194935353; a C or CC at base pair (bp) position 33363546; an A or AA at base pair (bp) position 33368983; a T or TT at base pair (bp) position 33363625; a C or CC at base pair (bp) position 164854921; a G or GG at base pair (bp) position 164858109; an A or AA at base pair (bp) position 164855482; or any combination thereof; and selecting a progeny maize plant or germplasm that comprises said marker within its genome, thereby selecting a maize plant or germplasm having increased yield under non-drought conditions, increased yield stability under drought conditions, and/or increased drought tolerance. In some embodiments, the alleles at the base pair positions as defined herein can be independently heterozygous or homozygous.

The present invention provides maize plants and germplasms having increased yield under non-drought conditions, increased yield stability under drought conditions, and/or increased drought tolerance as compared to a control. As discussed above, the methods of the present invention can be utilized to identify, produce and/or select a maize plant or germplasm having increased yield under non-drought conditions, increased yield stability under drought conditions, and/or increased drought tolerance. In addition to the methods described above, a maize plant or germplasm having increased yield under non-drought conditions, increased yield stability under drought conditions, and/or increased drought tolerance may be produced by any method whereby a marker associated with increased yield under non-drought conditions, increased yield stability under drought conditions, and/or increased drought tolerance in a maize plant is introduced into the maize plant or germplasm. Such methods include, but are not limited to, transformation (including, but not limited to, bacterial-mediated nucleic acid delivery (e.g., via *Agrobacteria*)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof, protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced, these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a maize plant or maize plant part having a genetic marker associated with increased yield under non-drought conditions, increased yield stability under drought conditions, and/or increased drought tolerance, obtainable by the methods of the presently disclosed subject matter, are aspects of the presently disclosed subject matter. The maize plant, or maize plant parts, or maize germplasm of this invention having at least one genetic marker associated with increased yield under non-drought conditions, increased yield stability under drought conditions, and/or increased drought tolerance can be heterozygous or homozygous for the genetic marker.

In some embodiments, the maize plant or germplasm may be the progeny of a cross between an elite maize variety and a variety of maize that comprises an allele associated with increased yield under non-drought conditions, increased yield stability under drought conditions, and/or increased drought tolerance. In some embodiments, the maize plant or germplasm is at least about 60%, 65%, 70%, 75%, 80%, 85%, 90%, 95%, 97%, 99% or 100% identical to that of an elite variety of maize.

The maize plant or germplasm may be the progeny of an introgression wherein the recurrent parent is an elite variety of maize and the donor comprises a genetic marker associated (e.g., SNP, combination of SNPs, SNP located in a chromosome interval) with increased yield under non-drought conditions, increased yield stability under drought conditions, and/or increased drought tolerance in a maize plant as described herein.

The maize plant or germplasm may be the progeny of a cross between a first elite variety of maize (e.g., a tester line) and the progeny of a cross between a second elite variety of maize (e.g., a recurrent parent) and a variety of maize that comprises a genetic marker associated with increased yield under non-drought conditions, increased yield stability under drought conditions, and/or increased drought tolerance in a maize plant as described herein (e.g., a donor).

Another aspect of the presently disclosed subject matter relates to a method of producing seeds that can be grown into maize plants comprising increased yield under non-drought conditions, increased yield stability under drought conditions, and/or increased drought tolerance. In some embodiments, the method comprises providing a maize plant of this invention having increased yield under non-drought conditions, increased yield stability under drought conditions, and/or increased drought tolerance, crossing said maize plant with another maize plant, and collecting seeds resulting from the cross, which when planted, produce maize plants having increased yield under non-drought conditions, increased yield stability under drought conditions, and/or increased drought tolerance as compared to a control (e.g., the "another maize plant").

Accordingly, the present invention provides improved maize plants, seeds, and/or maize tissue culture produced by the methods described herein.

In some embodiments, the presently disclosed subject matter provides methods for analyzing the genomes of maize plants/germplasms to identify those that include desired markers associated with increased yield under non-drought conditions, increased yield stability under drought conditions, and/or increased drought tolerance. In some embodiments, the methods of analysis comprise amplifying subsequences of the genomes of the maize plants/germplasms and determining the nucleotides present in one, some, or all positions of the amplified subsequences.

Additional aspects of the invention include a harvested product produced from the plants and/or parts thereof of the invention, as well as a post-harvest product produced from said harvested product. A harvested product can be a whole plant or any plant part, as described herein, wherein said harvested product comprises a recombinant nucleic acid molecule/nucleotide sequence of the invention. Thus, in some embodiments, non-limiting examples of a harvested product include a seed, a fruit, a flower or part thereof (e.g., an anther, a stigma, and the like), a leaf, a stem, and the like. In other embodiments, a post-harvested product includes, but is not limited to, a flour, meal, oil, starch, cereal, and the like produced from a harvested seed of the invention, wherein said seed comprises in its genome a recombinant nucleic acid molecule/nucleotide sequence of the invention.

In some embodiments, the invention further provides a maizr crop comprising a plurality of maize plants of the invention planted together in, for example, an agricultural field, a golf course, a residential lawn, a road side, an athletic field, and/or a recreational field.

In some embodiments, a method of improving the yield of a maize crop when said maize crop is exposed to drought conditions is provided, the method comprising cultivating a plurality of plants of the invention as the plant crop, wherein the plurality of plants of said maizer crop have increased yield under non-drought conditions, increased yield stability under drought conditions, and/or increased drought tolerance, thereby improving the yield of said maize crop as compared to a control maize crop, wherein the control plant crop is produced from a plurality of maize plants lacking said genetic marker grown under the same environmental conditions.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1. Identification of Markers Associated with Increased Yield Under Non-Drought Conditions, Increased Yield Stability Under Drought Conditions, and/or Increased Drought Tolerance Several genome-wide association studies (GWAS) were performed to identify markers associated with three yield traits (yield under irrigation, yield under drought stress and the difference between them) using diverse inbred and hybrid panels of maize. The inbred panel consisted of 262,224 genic SNPs across 478 inbred lines. The hybrid panel was split between the two heterotic groups (294 non-stiff stalk lines crossed to a single tester and 210 stiff stalk lines crossed to a different single tester) and between two years. The first year (2008) consisted primarily of locations used for flowering-time drought stress and the second year (2009) consisted primarily of locations used for season-long drought stress. The non-stiff stalk panels consisted of approximately 230,000 SNPs and the stiff stalk panels consisted of approximately 150,000 SNPs. At least 4 lines contained the minor allele (less common allele) in the case of all the SNPs.

Best linear unbiased predictors (BLUPs) were calculated for yield under irrigation and yield under drought stress for each line in each panel according to the model: Trait=Line+Trial+Line×Trial+error. The BLUPs for yield under irrigation and yield under drought stress were then standardized and these values were used to calculate the difference between the two traits (standardized yield under irrigation−standardized yield under drought stress). Associations were conducted using the model: y=Pv+Sα+Iu+e. Where y is a vector of phenotypic values (BLUPs), v is a vector of fixed effects regarding population structure, α is the fixed effect for the candidate marker, u is a vector of the random effects pertaining to recent co-ancestry, and e is a vector of residuals. P is a matrix of principal component (PC) vectors defining population structure, S is the vector of genotypes at the candidate marker, and I is an identity matrix. The variances of the random effects are assumed to be Var(u)=2KV$_g$ and Var(e)=IV$_R$, where K is the kinship matrix consisting of the proportion of shared allele values.

All markers were extracted that fell within a set of 23 putative SWEET genes from maize in order to take a candidate gene-based approach for identifying potential associations. This resulted in 113 markers examined for yield under irrigation and yield under drought stress in the five testing panels described above (results attached below in Tables 2.1-2.4). In some cases a particular marker may not have been tested in a specific panel due to too few lines with the minor genotype which varied from panel to panel. A QQ-Plot was generated to look at the observed distribution of −log 10(P-values) (FIG. 1). Based on the QQ-Plot a −log 10(P-value) threshold of 2 was used to select marker-trait associations (MTAs) to be used to help prioritize construct leads. Those markers showing a significant association are provided in Table 1.

TABLE 2.1

Data for the 113 markers examined for yield under irrigation and yield under drought stress in the five testing panels described in Example 1.

| SNP | GeneModelID | Description | Chr | Gene begin | Gene end |
|---|---|---|---|---|---|
| 1 | GRMZM2G173669 | SWEET-13a | chr10 | 14762443 | 14765098 |
| 2 | GRMZM2G039365 | SWEET-1a | chr3 | 171748815 | 171752467 |
| 3 | GRMZM2G039365 | SWEET-1a | chr3 | 171748815 | 171752467 |
| 4 | GRMZM2G368827 | SWEET-11/MtN3 | chr1 | 194932443 | 194935353 |
| 5 | GRMZM2G039365 | SWEET-1a | chr3 | 171748815 | 171752467 |
| 6 | GRMZM2G039365 | SWEET-1a | chr3 | 171748815 | 171752467 |
| 7 | GRMZM2G039365 | SWEET-1a | chr3 | 171748815 | 171752467 |
| 8 | GRMZM2G173669 | SWEET-13a | chr10 | 14762443 | 14765098 |
| 9 | GRMZM2G173669 | SWEET-13a | chr10 | 14762443 | 14765098 |
| 10 | GRMZM2G111926 | SWEET-16b | chr8 | 33363546 | 33368983 |
| 11 | GRMZM2G173669 | SWEET-13a | chr10 | 14762443 | 14765098 |
| 12 | GRMZM5G872392 | SWEET-15b | chr5 | 164854921 | 164858109 |
| 13 | GRMZM2G173669 | SWEET-13a | chr10 | 14762443 | 14765098 |

TABLE 2.1-continued

Data for the 113 markers examined for yield under irrigation and yield under drought stress in the five testing panels described in Example 1.

| SNP | GeneModelID | Description | Chr | Gene begin | Gene end |
|---|---|---|---|---|---|
| 14 | GRMZM2G173669 | SWEET-13a | chr10 | 14762443 | 14765098 |
| 15 | GRMZM2G173669 | SWEET-13a | chr10 | 14762443 | 14765098 |
| 16 | GRMZM2G173669 | SWEET-13a | chr10 | 14762443 | 14765098 |
| 17 | GRMZM2G173669 | SWEET-13a | chr10 | 14762443 | 14765098 |
| 18 | GRMZM2G173669 | SWEET-13a | chr10 | 14762443 | 14765098 |
| 19 | GRMZM2G173669 | SWEET-13a | chr10 | 14762443 | 14765098 |
| 20 | GRMZM2G039365 | SWEET-1a | chr3 | 171748815 | 171752467 |
| 21 | GRMZM2G000812 | Sweet-4a | chr5 | 126816126 | 126819003 |
| 22 | GRMZM2G000812 | Sweet-4a | chr5 | 126816126 | 126819003 |
| 23 | GRMZM2G144581 | Sweet-4b | chr5 | 127602043 | 127605592 |
| 24 | GRMZM2G144581 | Sweet-4b | chr5 | 127602043 | 127605592 |
| 25 | GRMZM2G173669 | SWEET-13a | chr10 | 14762443 | 14765098 |
| 26 | GRMZM2G153358 | SWEET-1b | chr6 | 147913391 | 147916344 |
| 27 | GRMZM2G179349 | SWEET-13c | chr3 | 108706693 | 108708062 |
| 28 | GRMZM5G872392 | SWEET-15b | chr5 | 164854921 | 164858109 |
| 29 | GRMZM2G111926 | SWEET-16b | chr8 | 33363546 | 33368983 |
| 30 | GRMZM2G111926 | SWEET-16b | chr8 | 33363546 | 33368983 |
| 31 | GRMZM2G173669 | SWEET-13a | chr10 | 14762443 | 14765098 |
| 32 | GRMZM2G039365 | SWEET-1a | chr3 | 171748815 | 171752467 |
| 33 | GRMZM5G872392 | SWEET-15b | chr5 | 164854921 | 164858109 |
| 34 | GRMZM2G106462 | SWEET-16a | chr3 | 56812209 | 56820107 |
| 35 | GRMZM2G039365 | SWEET-1a | chr3 | 171748815 | 171752467 |
| 36 | GRMZM2G021706 | SWEET-13b | chr10 | 14642867 | 14645735 |
| 37 | GRMZM2G021706 | SWEET-13b | chr10 | 14642867 | 14645735 |
| 38 | GRMZM2G039365 | SWEET-1a | chr3 | 171748815 | 171752467 |
| 39 | GRMZM2G039365 | SWEET-1a | chr3 | 171748815 | 171752467 |
| 40 | GRMZM2G039365 | SWEET-1a | chr3 | 171748815 | 171752467 |
| 41 | GRMZM2G368827 | SWEET-11/MtN3 | chr1 | 194932443 | 194935353 |
| 42 | GRMZM2G173669 | SWEET-13a | chr10 | 14762443 | 14765098 |
| 43 | GRMZM2G173669 | SWEET-13a | chr10 | 14762443 | 14765098 |
| 44 | GRMZM2G173669 | SWEET-13a | chr10 | 14762443 | 14765098 |
| 45 | GRMZM2G039365 | SWEET-1a | chr3 | 171748815 | 171752467 |
| 46 | GRMZM2G106462 | SWEET-16a | chr3 | 56812209 | 56820107 |
| 47 | GRMZM2G021706 | SWEET-13b | chr10 | 14642867 | 14645735 |
| 48 | GRMZM2G021706 | SWEET-13b | chr10 | 14642867 | 14645735 |
| 49 | GRMZM2G039365 | SWEET-1a | chr3 | 171748815 | 171752467 |
| 50 | GRMZM2G153358 | SWEET-1b | chr6 | 147913391 | 147916344 |
| 51 | GRMZM5G872392 | SWEET-15b | chr5 | 164854921 | 164858109 |
| 52 | GRMZM2G111926 | SWEET-16b | chr8 | 33363546 | 33368983 |
| 53 | GRMZM2G153358 | SWEET-1b | chr6 | 147913391 | 147916344 |
| 54 | GRMZM2G039365 | SWEET-1a | chr3 | 171748815 | 171752467 |
| 55 | GRMZM2G173669 | SWEET-13a | chr10 | 14762443 | 14765098 |
| 56 | GRMZM2G111926 | SWEET-16b | chr8 | 33363546 | 33368983 |
| 57 | GRMZM2G039365 | SWEET-1a | chr3 | 171748815 | 171752467 |
| 58 | GRMZM2G000812 | Sweet-4a | chr5 | 126816126 | 126819003 |
| 59 | GRMZM2G153358 | SWEET-1b | chr6 | 147913391 | 147916344 |
| 60 | GRMZM2G111926 | SWEET-16b | chr8 | 33363546 | 33368983 |
| 61 | GRMZM5G872392 | SWEET-15b | chr5 | 164854921 | 164858109 |
| 62 | GRMZM2G021706 | SWEET-13b | chr10 | 14642867 | 14645735 |
| 63 | GRMZM2G173669 | SWEET-13a | chr10 | 14762443 | 14765098 |
| 64 | GRMZM2G173669 | SWEET-13a | chr10 | 14762443 | 14765098 |
| 65 | GRMZM2G144581 | Sweet-4b | chr5 | 127602043 | 127605592 |
| 66 | GRMZM2G144581 | Sweet-4b | chr5 | 127602043 | 127605592 |
| 67 | GRMZM2G153358 | SWEET-1b | chr6 | 147913391 | 147916344 |
| 68 | GRMZM2G173669 | SWEET-13a | chr10 | 14762443 | 14765098 |
| 69 | GRMZM2G173669 | SWEET-13a | chr10 | 14762443 | 14765098 |
| 70 | GRMZM2G368827 | SWEET-11/MtN3 | chr1 | 194932443 | 194935353 |
| 71 | GRMZM2G000812 | Sweet-4a | chr5 | 126816126 | 126819003 |
| 72 | GRMZM2G000812 | Sweet-4a | chr5 | 126816126 | 126819003 |
| 73 | GRMZM2G144581 | Sweet-4b | chr5 | 127602043 | 127605592 |
| 74 | GRMZM2G144581 | Sweet-4b | chr5 | 127602043 | 127605592 |
| 75 | GRMZM2G153358 | SWEET-1b | chr6 | 147913391 | 147916344 |
| 76 | GRMZM2G153358 | SWEET-1b | chr6 | 147913391 | 147916344 |
| 77 | GRMZM5G872392 | SWEET-15b | chr5 | 164854921 | 164858109 |
| 78 | GRMZM2G039365 | SWEET-1a | chr3 | 171748815 | 171752467 |
| 79 | GRMZM2G039365 | SWEET-1a | chr3 | 171748815 | 171752467 |
| 80 | GRMZM5G872392 | SWEET-15b | chr5 | 164854921 | 164858109 |
| 81 | GRMZM5G872392 | SWEET-15b | chr5 | 164854921 | 164858109 |
| 82 | GRMZM2G039365 | SWEET-1a | chr3 | 171748815 | 171752467 |
| 83 | GRMZM2G039365 | SWEET-1a | chr3 | 171748815 | 171752467 |
| 84 | GRMZM2G021706 | SWEET-13b | chr10 | 14642867 | 14645735 |
| 85 | GRMZM2G021706 | SWEET-13b | chr10 | 14642867 | 14645735 |
| 86 | GRMZM2G179679 | SWEET-3a | chr8 | 112530662 | 112532375 |
| 87 | GRMZM2G000812 | Sweet-4a | chr5 | 126816126 | 126819003 |
| 88 | GRMZM2G153358 | SWEET-1b | chr6 | 147913391 | 147916344 |

TABLE 2.1-continued

Data for the 113 markers examined for yield under irrigation and yield under drought stress in the five testing panels described in Example 1.

| SNP | GeneModelID | Description | Chr | Gene begin | Gene end |
|---|---|---|---|---|---|
| 89 | GRMZM2G153358 | SWEET-1b | chr6 | 147913391 | 147916344 |
| 90 | GRMZM2G368827 | SWEET-11/MtN3 | chr1 | 194932443 | 194935353 |
| 91 | GRMZM2G021706 | SWEET-13b | chr10 | 14642867 | 14645735 |
| 92 | GRMZM2G039365 | SWEET-1a | chr3 | 171748815 | 171752467 |
| 93 | GRMZM2G039365 | SWEET-1a | chr3 | 171748815 | 171752467 |
| 94 | GRMZM2G153358 | SWEET-1b | chr6 | 147913391 | 147916344 |
| 95 | GRMZM2G021706 | SWEET-13b | chr10 | 14642867 | 14645735 |
| 96 | GRMZM2G168365 | SWEET-15a | chr4 | 96310951 | 96312854 |
| 97 | GRMZM5G872392 | SWEET-15b | chr5 | 164854921 | 164858109 |
| 98 | GRMZM2G021706 | SWEET-13b | chr10 | 14642867 | 14645735 |
| 99 | GRMZM2G368827 | SWEET-11/MtN3 | chr1 | 194932443 | 194935353 |
| 100 | GRMZM2G021706 | SWEET-13b | chr10 | 14642867 | 14645735 |
| 101 | GRMZM2G106462 | SWEET-16a | chr3 | 56812209 | 56820107 |
| 102 | GRMZM2G173669 | SWEET-13a | chr10 | 14762443 | 14765098 |
| 103 | GRMZM2G173669 | SWEET-13a | chr10 | 14762443 | 14765098 |
| 104 | GRMZM2G144581 | Sweet-4b | chr5 | 127602043 | 127605592 |
| 105 | GRMZM2G173669 | SWEET-13a | chr10 | 14762443 | 14765098 |
| 106 | GRMZM2G368827 | SWEET-11/MtN3 | chr1 | 194932443 | 194935353 |
| 107 | GRMZM2G039365 | SWEET-1a | chr3 | 171748815 | 171752467 |
| 108 | GRMZM2G021706 | SWEET-13b | chr10 | 14642867 | 14645735 |
| 109 | GRMZM2G153358 | SWEET-1b | chr6 | 147913391 | 147916344 |
| 110 | GRMZM2G173669 | SWEET-13a | chr10 | 14762443 | 14765098 |
| 111 | GRMZM2G021706 | SWEET-13b | chr10 | 14642867 | 14645735 |
| 112 | GRMZM2G368827 | SWEET-11/MtN3 | chr1 | 194932443 | 194935353 |
| 113 | GRMZM2G106462 | SWEET-16a | chr3 | 56812209 | 56820107 |

TABLE 2.2

Data for the 113 markers examined for yield under irrigation and yield under drought stress in the five testing panels described in Example 1, continued.

| SNP | Marker | Site | hyb_irr_nss_2008_NegLogP | hyb_irr_nss_2009_NegLogP |
|---|---|---|---|---|
| 1 | PZE1014822710 | 14764762 | 2.48339402 | 1.93998254 |
| 2 | PZE03170079889 | 171752311 | 0.80951454 | 3.08080659 |
| 3 | PZE03170077114 | 171749536 | 0.01915102 | 0.37952685 |
| 4 | PZE01194799632 | 194932443 | 0.85943617 | 1.17238029 |
| 5 | S_7767530 | 171749273 | 1.29880915 | 2.55131038 |
| 6 | S_7767535 | 171749283 | 1.29880915 | 2.55131038 |
| 7 | S_7767546 | 171749318 | 1.29880915 | 2.55131038 |
| 8 | PZE1014822787 | 14764839 | 0.42135623 | 0.26547596 |
| 9 | PZE1014822363 | 14764415 | 0.17635843 | 0.18174604 |
| 10 | PZE0833363225 | 33363625 | 0.06956905 | 1.13162812 |
| 11 | PZE1014822960 | 14765012 | 0.85169843 | 0.91924154 |
| 12 | S_25177407 | 164855482 | 0.69820466 | 0.67099443 |
| 13 | S_3355011 | 14764763 | 1.1780373 | 1.57865605 |
| 14 | PZE1014822606 | 14764658 | 0.56943117 | 0.08699943 |
| 15 | PZE1014822564 | 14764616 | 0.49697049 | 0.33590677 |
| 16 | S_3354810 | 14764696 | 0.44083186 | 0.38491027 |
| 17 | PZE1014822691.S_3354951 | 14764743 | 0.99690825 | 1.20836387 |
| 18 | PZE1014822841.S_3355363 | 14764893 | 0.79186145 | 0.91622315 |
| 19 | PZE1014822866.S_3355438 | 14764918 | 0.79186145 | 0.91622315 |
| 20 | PZE03170076681.S_7767421 | 171749103 | 0.11900814 | 0.00865314 |
| 21 | PZE05126115268.S_11834715 | 126816519 | 0.2079189 | 0.13401627 |
| 22 | S_11834745 | 126816572 | 0.2079189 | 0.13401627 |
| 23 | PZE05126891291 | 127605008 | 0.83345758 | 1.6839096 |
| 24 | PZE05126891427.S_11835752 | 127605144 | 0.83345758 | 1.6839096 |
| 25 | PZE1014822809.S_3355271 | 14764861 | 0.01245327 | 0.74596913 |
| 26 | S_14101102 | 147913800 | 0.32257144 | 0.13757348 |
| 27 | PZE0386521032.S_7281790 | 108707214 | 1.5683837 | 1.31891826 |
| 28 | S_12049233 | 164855895 | | |
| 29 | PZE0833363158.S_16494064 | 33363558 | 0.08469174 | 0.86221774 |
| 30 | PZE0833363197.S_16494076 | 33363597 | 0.08469174 | 0.86221774 |
| 31 | S_3354602 | 14764622 | 0.65441341 | 0.16214315 |
| 32 | PZE03170079878.S_7768070 | 171752300 | 1.35406698 | 0.1877092 |
| 33 | S_25177376 | 164855387 | 0.2351574 | 0.29429341 |
| 34 | PZE0356470659.S_7124418 | 56812375 | | |
| 35 | PZE03170077201.S_7767630 | 171749623 | 0.38453167 | 0.28107766 |
| 36 | PZE1014702229 | 14644281 | 1.13164967 | 0.51957672 |
| 37 | S_3349719 | 14644977 | 1.14601099 | 1.25251975 |
| 38 | PZE03170076798 | 171749220 | 0.78567606 | 0.82631165 |
| 39 | PZE03170078108.S_7767931 | 171750530 | 0.23477054 | 1.23784226 |

TABLE 2.2-continued

Data for the 113 markers examined for yield under irrigation and yield under drought stress in the five testing panels described in Example 1, continued.

| SNP | Marker | Site | hyb_irr_nss_2008_NegLogP | hyb_irr_nss_2009_NegLogP |
|---|---|---|---|---|
| 40 | S_55135874 | 171749906 | | 0.14198191 |
| 41 | PZE01194801358 | 194934169 | | 0.79314162 |
| 42 | PZE1014822786.S_3355207 | 14764838 | 0.24523972 | 1.1831317 |
| 43 | PZE1014822819.S_3355299 | 14764871 | 0.24523972 | 1.1831317 |
| 44 | PZE1014822928 | 14764980 | 0.24523972 | 1.1831317 |
| 45 | PZE03170076953.S_7767584 | 171749375 | 0.12667685 | 1.18035898 |
| 46 | PZE0356471257 | 56812973 | | |
| 47 | PZE1014702037 | 14644089 | 0.38125336 | 0.28426884 |
| 48 | S_3348847 | 14643477 | 0.16215297 | 0.6734687 |
| 49 | PZE03170077026 | 171749448 | 0.2181933 | 0.07603965 |
| 50 | PZE06148080134 | 147915823 | 0.06038515 | 0.54062193 |
| 51 | S_25177378 | 164855388 | 0.23544921 | 0.2283158 |
| 52 | PZE0833363578 | 33363978 | 0.23143252 | 1.07639439 |
| 53 | PZE06148080313 | 147916002 | 0.61740718 | 0.46596029 |
| 54 | S_23029935 | 171752133 | 1.06640515 | 0.51746593 |
| 55 | PZE1014821787.S_3353035 | 14763839 | 1.05948751 | 0.2107891 |
| 56 | S_16494954 | 33368521 | 0.38046935 | 1.02758367 |
| 57 | PZE03170076625.S_7767384 | 171749047 | 0.38453167 | 0.46470533 |
| 58 | PZE05126115149.S_25071732 | 126816400 | 0.41281548 | 0.28286337 |
| 59 | PZE06148078578 | 147914267 | 0.32958285 | 1.04140018 |
| 60 | S_16494695 | 33367991 | 1.0281558 | 0.64993946 |
| 61 | S_33794968 | 164856230 | 1.01816406 | 0.35236426 |
| 62 | PZE1014701114 | 14643166 | 0.08155626 | 0.43892973 |
| 63 | PZE1014822003.S_3353589 | 14764055 | 0.03416064 | 0.53398819 |
| 64 | S_3353692 | 14764202 | | |
| 65 | PZE05126891289 | 127605006 | 0.36125549 | 0.24063273 |
| 66 | PZE05126891675 | 127605392 | 0.36125549 | 0.20252672 |
| 67 | PZE06148077991.S_14100829 | 147913680 | 0.09065364 | 0.02898161 |
| 68 | S_3355358 | 14764891 | | |
| 69 | S_3355625 | 14765003 | | |
| 70 | PZE01194801561 | 194934372 | 0.94554625 | 0.84000889 |
| 71 | PZE05126116874 | 126818125 | | |
| 72 | PZE05126117144 | 126818395 | | |
| 73 | PZE05126889656.S_11835494 | 127603373 | 0.71174015 | 0.44459382 |
| 74 | PZE05126889836.S_11835524 | 127603553 | 0.71174015 | 0.44459382 |
| 75 | S_14100779 | 147913649 | 0.07955528 | 0.15616572 |
| 76 | S_14101249 | 147913892 | 0.00902683 | 0.34687826 |
| 77 | S_12049219 | 164855078 | 0.91412257 | 0.61446207 |
| 78 | PZE03170076986.S_7767599 | 171749408 | 0.30600068 | 0.03369069 |
| 79 | PZE03170076676.S_7767416 | 171749098 | 0.4951291 | 0.32049511 |
| 80 | S_25177445 | 164855596 | 0.30128326 | 0.133377 |
| 81 | S_33794965 | 164856183 | 0.22150278 | 0.48601471 |
| 82 | PZE03170076989.S_7767600 | 171749411 | 0.82255903 | 0.0083933 |
| 83 | PZE03170077032 | 171749454 | 0.82255903 | 0.0083933 |
| 84 | PZE1014702682.S_3349436 | 14644734 | 0.86440975 | 0.22637006 |
| 85 | PZE1014702775.S_3349611 | 14644827 | 0.86440975 | 0.22637006 |
| 86 | PZE08111162512 | 112532312 | | |
| 87 | PZE05126115152.S_11834667 | 126816403 | 0.0251784 | 0.81197321 |
| 88 | S_14101038 | 147913767 | 0.21532276 | 0.20231402 |
| 89 | S_14101413 | 147914335 | 0.07852808 | 0.16386486 |
| 90 | S_49741167 | 194933875 | | 0.21886861 |
| 91 | PZE1014702114 | 14644166 | | |
| 92 | PZE03170078386 | 171750808 | | |
| 93 | PZE03170078405 | 171750827 | | |
| 94 | PZE06148079640 | 147915329 | 0.10227987 | 0.00545827 |
| 95 | PZE1014703058.S_3349905 | 14645110 | 0.72205718 | 0.05191929 |
| 96 | PZE04103664044 | 96311232 | 0.16240214 | 0.0892337 |
| 97 | S_33794964 | 164856180 | 0.01683392 | 0.07885298 |
| 98 | PZE1014703254.S_3350242 | 14645306 | 0.32558755 | 0.51510299 |
| 99 | PZE01194799750.S_20076659 | 194932561 | 0.29531278 | 0.00565575 |
| 100 | PZE1014701102 | 14643154 | 0.37088935 | 0.62915452 |
| 101 | S_7124415 | 56812284 | | |
| 102 | S_3354083 | 14764448 | | |
| 103 | S_3354105 | 14764455 | | |
| 104 | PZE05126889689 | 127603406 | | |
| 105 | PZE1014821892.S_3353328 | 14763944 | | |
| 106 | PZE01194800515.S_20076953 | 194933326 | 0.48477092 | 0.03444593 |
| 107 | PZE03170079877.S_7768069 | 171752299 | 0.37278741 | 0.45828978 |
| 108 | S_3350152 | 14645275 | | |
| 109 | PZE06148077958.S_14100776 | 147913647 | 0.21745347 | 0.23155189 |
| 110 | S_3353995 | 14764418 | | |
| 111 | PZE1014700929 | 14642981 | | |
| 112 | S_20077149 | 194935223 | | |
| 113 | PZE0356471931 | 56813647 | | |

TABLE 2.3

Data for the 113 markers examined for yield under irrigation and yield under
drought stress in the five testing panels described in Example 1, continued.

| SNP | hyb_irr_ss_2008_NegLogP | hyb_irr_ss_2009_NegLogP | hyb_str_nss_2008_NegLogP | hyb_str_nss_2009_NegLogP |
|---|---|---|---|---|
| 1 | | | 3.39143188 | 1.4803721 |
| 2 | 0.17035041 | 0.15083801 | 0.04265472 | 1.38336068 |
| 3 | 2.60149002 | 0.46241344 | 0.10046913 | 0.45416226 |
| 4 | 0.24142934 | 0.37040433 | 0.42821394 | 0.28761583 |
| 5 | 1.24732304 | 1.34656524 | 0.47643233 | 1.12107774 |
| 6 | 1.24732304 | 1.34656524 | 0.47643233 | 1.12107774 |
| 7 | 1.24732304 | 1.34656524 | 0.47643233 | 1.12107774 |
| 8 | 0.08226949 | 0.69270568 | 0.76344493 | 0.20260388 |
| 9 | 0.0394166 | 0.6487939 | 0.0324467 | 0.17463126 |
| 10 | 0.66515757 | 0.33654449 | 0.69628303 | 2.31572792 |
| 11 | | | 2.31533522 | 1.01516461 |
| 12 | 0.89221201 | 1.41575634 | 0.00794551 | 0.26033852 |
| 13 | | | 2.20181199 | 1.86373415 |
| 14 | 0.01009048 | 0.5880692 | 0.66912419 | 0.6967561 |
| 15 | 0.03978049 | 0.66876859 | 0.68017307 | 0.28246053 |
| 16 | 0.11586244 | 0.56134977 | 0.52037422 | 0.33815468 |
| 17 | | | 1.87979971 | 0.94138623 |
| 18 | | | 1.80179111 | 0.9850086 |
| 19 | | | 1.80179111 | 0.9850086 |
| 20 | 0.90166818 | 0.14862839 | 0.42571055 | 0.16682025 |
| 21 | 0.07171003 | 0.2249717 | 0.11157745 | 1.75450587 |
| 22 | 0.07171003 | 0.2249717 | 0.11157745 | 1.75450587 |
| 23 | | | 0.1680075 | 0.3179246 |
| 24 | | | 0.1680075 | 0.3179246 |
| 25 | 0.21064378 | 0.55333316 | 0.38183604 | 0.7257265 |
| 26 | | | 0.27214435 | 0.01218352 |
| 27 | | | 0.36668521 | 1.0273156 |
| 28 | 0.06916874 | 0.92722315 | | |
| 29 | 0.54143235 | 0.62092881 | 0.24379132 | 1.46841459 |
| 30 | 0.47882086 | 0.72908185 | 0.24379132 | 1.46841459 |
| 31 | 1.40942615 | 0.2525479 | 0.33747166 | 0.17561225 |
| 32 | | | 0.22775511 | 0.20636099 |
| 33 | | | 0.16613632 | 0.07044957 |
| 34 | | | | |
| 35 | | | 0.00674386 | 0.21213239 |
| 36 | | | 1.27178032 | 0.52889891 |
| 37 | | | 0.70339154 | 0.67286045 |
| 38 | 0.00880482 | 0.37389168 | 0.98180881 | 1.23848499 |
| 39 | | | 0.27464134 | 0.1701788 |
| 40 | 0.60955534 | 0.10276846 | | 0.13080242 |
| 41 | | | | 0.14467926 |
| 42 | | | 0.58093681 | 0.49845824 |
| 43 | | | 0.58093681 | 0.49845824 |
| 44 | | | 0.58093681 | 0.49845824 |
| 45 | | | 0.02818854 | 0.11809184 |
| 46 | 0.2603309 | 0.54498871 | | |
| 47 | 0.07871399 | 0.15019633 | 0.84039179 | 1.16318697 |
| 48 | 0.21488713 | 0.00364405 | 0.6531258 | 1.16156555 |
| 49 | 0.32048789 | 0.03471632 | 0.09529312 | 0.01989565 |
| 50 | | | 0.17180631 | 0.01684251 |
| 51 | | | 0.372673 | 0.15935658 |
| 52 | 0.18352772 | 0.60785611 | 0.17161956 | 0.78005224 |
| 53 | 0.09885423 | 0.70315714 | 0.85810591 | 0.09850591 |
| 54 | | | 0.14280239 | 1.0603578 |
| 55 | | | 0.00214107 | 0.26888295 |
| 56 | | | 0.11795649 | 0.304178 |
| 57 | | | 0.00674386 | 0.09139199 |
| 58 | | | 0.20615436 | 1.04273075 |
| 59 | | | 0.07559816 | 0.41486199 |
| 60 | | | 0.50471775 | 0.31009355 |
| 61 | | | 0.32385166 | 0.43967138 |
| 62 | 0.10343422 | 0.19339268 | 0.16128381 | 0.24096409 |
| 63 | | | 0.08954728 | 0.4201517 |
| 64 | | | | |
| 65 | 0.39490445 | 0.86126817 | 0.06464071 | 0.54750432 |
| 66 | 0.39490445 | 0.86126817 | 0.06464071 | 0.64083061 |
| 67 | | | 0.1292642 | 0.08327594 |
| 68 | 0.70286357 | 0.01891023 | | |
| 69 | 0.70286357 | 0.01891023 | | |
| 70 | | | 0.30345124 | 0.89740677 |
| 71 | | | | |
| 72 | | | | |
| 73 | | | 0.70017186 | 0.24389019 |
| 74 | | | 0.70017186 | 0.24389019 |
| 75 | 0.8337981 | 0.32359724 | 0.20778395 | 0.74528403 |

TABLE 2.3-continued

Data for the 113 markers examined for yield under irrigation and yield under
drought stress in the five testing panels described in Example 1, continued.

| SNP | hyb_irr_ss_2008_NegLogP | hyb_irr_ss_2009_NegLogP | hyb_str_nss_2008_NegLogP | hyb_str_nss_2009_NegLogP |
|---|---|---|---|---|
| 76 | 0.8337981 | 0.32359724 | 0.14437167 | 0.6873758 |
| 77 | 0.60321326 | 0.01628966 | 0.23165403 | 0.22630309 |
| 78 | 0.17164071 | 0.64915989 | 0.15059474 | 0.51382078 |
| 79 |  |  | 0.09857463 | 0.05819587 |
| 80 | 0.76351467 | 0.18058756 | 0.11714046 | 0.32463538 |
| 81 | 0.25865768 | 0.25946203 | 0.18284056 | 0.08950717 |
| 82 | 0.29490762 | 0.33754669 | 0.33860049 | 0.34734388 |
| 83 | 0.29490762 | 0.33754669 | 0.33860049 | 0.34734388 |
| 84 |  |  | 0.72135738 | 0.34154198 |
| 85 |  |  | 0.72135738 | 0.34154198 |
| 86 |  |  |  |  |
| 87 |  |  | 0.10947197 | 0.56609322 |
| 88 |  |  | 0.20347512 | 0.80043395 |
| 89 |  |  | 0.19501085 | 0.79763293 |
| 90 |  |  |  | 0.21436624 |
| 91 | 0.36200708 | 0.61187712 |  |  |
| 92 |  |  |  |  |
| 93 |  |  |  |  |
| 94 |  |  | 0.18954134 | 0.74141519 |
| 95 |  |  | 0.66093211 | 0.12520398 |
| 96 | 0.23307677 | 0.67286986 | 0.25142866 | 0.03662018 |
| 97 | 0.43441612 | 0.34207415 | 0.00147716 | 0.57908725 |
| 98 | 0.0146588 | 0.28840556 | 0.12406035 | 0.63250236 |
| 99 |  |  | 0.14284817 | 0.63099133 |
| 100 | 0.56137911 | 0.27352189 | 0.07446952 | 0.19202566 |
| 101 |  |  |  |  |
| 102 |  |  |  |  |
| 103 |  |  |  |  |
| 104 |  |  |  |  |
| 105 |  |  |  |  |
| 106 |  |  | 0.03055306 | 0.2105521 |
| 107 |  |  | 0.07977212 | 0.18803518 |
| 108 | 0.42740335 | 0.03697505 |  |  |
| 109 |  |  | 0.14762923 | 0.30591534 |
| 110 |  |  |  |  |
| 111 | 0.05763862 |  |  |  |
| 112 |  |  |  |  |
| 113 | 0.14662528 |  |  |  |

TABLE 2.4

Data for the 113 markers examined for yield under irrigation and yield under
drought stress in the five testing panels described in Example 1, continued.

| SNP | hyb_str_ss_2008_NegLogP | hyb_str_ss_2009_NegLogP | inb_irr_NegLogP | inb_str_NegLogP |
|---|---|---|---|---|
| 1 |  |  | 0.373054399 | 0.076996764 |
| 2 | 0.20384843 | 0.279931 | 1.500484195 | 0.670790029 |
| 3 | 0.4399636 | 0.59132297 | 0.62228643 | 0.656175758 |
| 4 | 0.31037268 | 2.55740394 | 0.120744517 | 0.986680896 |
| 5 | 0.80420835 | 0.491335 | 0.499833323 | 0.636127781 |
| 6 | 0.80420835 | 0.491335 | 0.499833323 | 0.636127781 |
| 7 | 0.80420835 | 0.491335 | 0.499833323 | 0.636127781 |
| 8 | 2.40231752 | 1.26800461 | 0.295774098 | 0.009709508 |
| 9 | 2.37737739 | 0.56688203 | 0.43065048 | 0.452683321 |
| 10 | 0.59938658 | 0.66878475 | 0.114010795 | 0.005951511 |
| 11 |  |  | 0.221808508 | 1.379449511 |
| 12 | 0.12046294 | 2.25430347 | 0.50578442 | 0.043683773 |
| 13 |  |  | 0.285182163 | 0.355048953 |
| 14 | 2.12591997 | 0.82126335 | 0.220915086 | 0.062437492 |
| 15 | 1.99301641 | 1.0064282 | 0.266411049 | 0.165332726 |
| 16 | 1.9395473 | 0.41006296 | 0.534310238 | 0.03807785 |
| 17 |  |  | 0.079928948 | 0.817674324 |
| 18 |  |  | 0.088895297 | 1.373614984 |
| 19 |  |  | 0.088895297 | 1.373614984 |
| 20 | 0.92387922 | 1.75651396 | 0.324044082 | 0.093021432 |
| 21 | 0.46952224 | 0.18876057 | 0.114311589 | 0.013256512 |
| 22 | 0.46952224 | 0.18876057 | 0.114311589 | 0.013256512 |
| 23 |  |  | 0.836334763 | 0.087089228 |
| 24 |  |  | 0.539590869 | 0.084772044 |
| 25 | 1.61522161 | 1.1499741 | 0.571634535 | 0.507395516 |
| 26 |  |  | 0.329899175 | 1.569756551 |

TABLE 2.4-continued

Data for the 113 markers examined for yield under irrigation and yield under drought stress in the five testing panels described in Example 1, continued.

| SNP | hyb_str_ss_2008_NegLogP | hyb_str_ss_2009_NegLogP | inb_irr_NegLogP | inb_str_NegLogP |
|---|---|---|---|---|
| 27 | | | 0.03812525 | 0.004129948 |
| 28 | 0.39220084 | 0.00338498 | 1.48318061 | 0.732881644 |
| 29 | 0.55694877 | 0.37947032 | 0.567011759 | 0.08501641 |
| 30 | 0.6647357 | 0.37074831 | 0.306606148 | 0.014619638 |
| 31 | 1.21178291 | 0.08659301 | 0.661369831 | 1.128088593 |
| 32 | | | 0.196916201 | 0.318886372 |
| 33 | | | 1.123148402 | 1.339399124 |
| 34 | | | 0.435339592 | 1.304043311 |
| 35 | | | 1.275031713 | 1.000595196 |
| 36 | | | 0.053296334 | 0.366012088 |
| 37 | | | 0.111741885 | 1.035595681 |
| 38 | 0.05943094 | 0.34197826 | 0.244403507 | 0.394698158 |
| 39 | | | 0.614657472 | 0.828193448 |
| 40 | 0.57384751 | 1.22686808 | 0.617441001 | 0.369195761 |
| 41 | | | 0.898600064 | 1.192877118 |
| 42 | | | 0.635189751 | 0.031774589 |
| 43 | | | 0.462109042 | 0.215332784 |
| 44 | | | 0.462109042 | 0.215332784 |
| 45 | | | 0.75070662 | 0.884372283 |
| 46 | 1.17308179 | 0.34275546 | 0.07392808 | 0.084881527 |
| 47 | 0.09087783 | 0.38867158 | 0.500719704 | 0.329135138 |
| 48 | 1.0650841 | 0.40541214 | 0.498098923 | 0.667240935 |
| 49 | 0.31924899 | 1.13040968 | 0.740420949 | 0.049688845 |
| 50 | | | 0.280607024 | 1.119239292 |
| 51 | | | 0.880406377 | 1.08889322 |
| 52 | 0.11788978 | 0.47142233 | 0.991926824 | 0.759895665 |
| 53 | 0.54691989 | 0.64743411 | 1.069873955 | 0.093545818 |
| 54 | | | 0.099635146 | 0.046375319 |
| 55 | | | 0.054219933 | 0.02205439 |
| 56 | | | 1.058658119 | 0.439031785 |
| 57 | | | 0.923674412 | 1.046945321 |
| 58 | | | 0.601254631 | 0.497986267 |
| 59 | | | 0.923313767 | 0.949017422 |
| 60 | | | 0.106412931 | 0.31940991 |
| 61 | | | 0.118543162 | 0.035742647 |
| 62 | 1.01322275 | 0.20034712 | 0.574197909 | 0.317530916 |
| 63 | | | 0.315598219 | 1.007936407 |
| 64 | | | 0.902677655 | 0.978997285 |
| 65 | 0.976811 | 0.81332864 | 0.751278108 | 0.029576463 |
| 66 | 0.976811 | 0.81332864 | 0.813942695 | 0.150877497 |
| 67 | | | 0.530561112 | 0.965785588 |
| 68 | 0.95496493 | 0.24304959 | 0.031225577 | 0.139501054 |
| 69 | 0.95496493 | 0.24304959 | 0.005118358 | 0.126327378 |
| 70 | | | 0.13507934 | 0.300988246 |
| 71 | | | 0.381404942 | 0.941261233 |
| 72 | | | 0.381404942 | 0.941261233 |
| 73 | | | 0.367861331 | 0.928155204 |
| 74 | | | 0.367861331 | 0.928155204 |
| 75 | 0.91902831 | 0.3474665 | 0.321751596 | 0.238776131 |
| 76 | 0.91902831 | 0.3474665 | 0.328244125 | 0.006892388 |
| 77 | 0.26628927 | 0.30360471 | 0.172661772 | 0.094141347 |
| 78 | 0.08720609 | 0.90116286 | 0.363779149 | 0.260174022 |
| 79 | | | 0.754839994 | 0.889639553 |
| 80 | 0.55842804 | 0.88741576 | 0.189868222 | 0.442479239 |
| 81 | 0.43630846 | 0.88582055 | 0.738200969 | 0.103855159 |
| 82 | 0.53951015 | 0.87508174 | 0.419856631 | 0.025420967 |
| 83 | 0.53951015 | 0.87508174 | 0.419856631 | 0.025420967 |
| 84 | | | | |
| 85 | | | | |
| 86 | | | 0.839293909 | 0.196563596 |
| 87 | | | 0.216988836 | 0.022491942 |
| 88 | | | 0.321896287 | 0.323990061 |
| 89 | | | 0.141113753 | 0.344734649 |
| 90 | | | 0.782004637 | 0.403715325 |
| 91 | 0.42557976 | 0.16817132 | 0.694102707 | 0.754336779 |
| 92 | | | 0.313314916 | 0.747050149 |
| 93 | | | 0.313314916 | 0.747050149 |
| 94 | | | 0.106311353 | 0.053774493 |
| 95 | | | 0.595745125 | 0.652391602 |
| 96 | 0.33750562 | 0.35698415 | 0.080388865 | 0.02798058 |
| 97 | 0.26156448 | 0.60952707 | 0.637038663 | 0.157100172 |
| 98 | 0.15963718 | 0.28587802 | 0.361150032 | 0.061883957 |
| 99 | | | 0.334722878 | 0.415136614 |
| 100 | 0.04369916 | 0.07755263 | 0.213980447 | 0.053872558 |
| 101 | | | 0.428339218 | 0.610827375 |

TABLE 2.4-continued

Data for the 113 markers examined for yield under irrigation and yield under drought stress in the five testing panels described in Example 1, continued.

| SNP | hyb_str_ss_2008_NegLogP | hyb_str_ss_2009_NegLogP | inb_irr_NegLogP | inb_str_NegLogP |
|---|---|---|---|---|
| 102 | | | 0.537479086 | 0.609312506 |
| 103 | | | 0.537479086 | 0.609312506 |
| 104 | | | 0.186312847 | 0.579248188 |
| 105 | | | 0.267221962 | 0.509327867 |
| 106 | | | 0.023529605 | 0.046735768 |
| 107 | | | 0.04557972 | 0.078764555 |
| 108 | 0.15789273 | 0.02014709 | 0.073885391 | 0.260104342 |
| 109 | | | 0.074211147 | 0.360438138 |
| 110 | | | 0.202889986 | 0.005580223 |
| 111 | 0.19986353 | | | |
| 112 | | | 0.097822876 | 0.194000286 |
| 113 | 0.16996956 | | 0.07392808 | 0.084881527 |

Example 2. Identification of Markers Associated with Increased Yield Under Non-Drought Conditions, Increased Yield Stability Under Drought Conditions, and/or Increased Drought Tolerance Several family based association studies (FBAM) were performed to identify markers associated with three yield traits (yield under irrigation, yield under drought stress and the difference between them) using diverse inbred and hybrid panels of maize. Populations from 24 parental lines were used to generate the families (progeny lines) used in the NSS analyses. In total these parents had 167,854 variants segregating among them. The 24 parental lines were sequenced using a reduced genomic next generation sequencing approach and used to project the next generation sequencing variants onto the families within each population (or cross). Merging the genotypic and phenotypic data from the NSS-MSE analysis resulted in 24 parental lines crossed to generate 45 populations which had a grand total of 1040 families. These families were then crossed to two testers. Populations with less than 10 families were excluded from the analysis since they would provide little additional value.

Twenty parental lines were used to generate the populations and families for the SS datasets. Across these twenty parents 112,466 variants were segregating. Similar to the NSS datasets, parental lines were sequenced using a reduced genomic next generation sequencing approach and used to project the next generation sequencing variants onto the families within each population (or cross). Upon merging this genotypic data with the phenotypic data there were 23 populations and a grand total of 553 families that had genotypic and phenotypic data available. Replicates from these families were then crossed to two testers to generate the hybrids that were phenotyped.

The two initial models tested were the fixed effect model with interaction term (1) tested using PROC GLM in SAS and a random effect model with interaction term (2) tested using PROC Mixed REML in SAS.

$$y=\text{Population(fixed)}+\text{SNP(fixed)}+\text{Population}\times\text{SNP}\text{(fixed)}+\varepsilon \quad (1)$$

$$y=\text{Population(random)}+\text{SNP(fixed)}+\text{Population}\times\text{SNP}\text{(random)}+\varepsilon \quad (2)$$

Those markers showing a significant association with yield (YGSMN) when grown under irrigated conditions (non-drought) are provided in Table 3.

```
Nucleotide Sequences

Genomic sequences B73 maize
ZmSWEET13a [GRMZM2G173669]
Genomic sequence/Gene region->lcl|GRMZM2G173669
seq = gene; coord = 10:14762443..14765098:1
GCCTATATAAAGCCACCCACAGCCCTGCCTATCATTGCAAGAGTTTGAGC
CAACACACACAGAGAGGACAACTCCTCACAACTCTCCCTTCCCTCCTG
TAGGGGCCAAAAGGGTTAGAGAGTAGGAGAAGTAGTTCCCTAGCCCAACA
CAAGAAAAACAAGCTCGATCTCCTCATCACCCTAATCCAAGCAACTGCTT
TGTGTGTTGGGAAATTCTTGTGACCCCTGTTATATTATTATCCGTGTAGC
TACTAGCTTCATTCCCCCCTTTGTACCCATCAAATGGCTGGCATGTCTCT
GCAACACCCCTGGGCGTTTGCTTTCGGTCTACTAGGTACATACTACACCT
TCACTAATAGCTAAACAAGCGCCCGCCGCAAAGCTATGAATTAAGGGCAG
GCATGTTTGGTTTGCTACCTATTTTACCATACTTTGTCTAACTTTTCTGT
CTAAGGTTATAGTTCTTCAATTCGAACGATTAATCTTAGCCAAAGTGTGA
CATGGTTAGCCACGAACTAAGCAGGCCCTTAATTATTGCGCATGTATATA
TTATATATTTATCTTTCTATTCTGTTTAATTTGTTTTCTCTTTACATATA
TATACTACTATGTAAGTATATATTATATGCACAACAAGCAGGCCTCCTTC
GTGCACATATGCATAGAATCAATCTATACCCTTCATAGAAGCCACTTTGA
GATATACCTTCCAAAACAATCCCAAAAACAAGACGCTCGATCTTGCGCTC
ACAATCACTTAGTTTTGCACCAGATTAAGCATGCACCACTAGATTTTATG
TACTGTATTACCTCTGCCATCCATGGTCGATCCTTTAGTTTATCCTATTC
ATTTCCGTCATGAACTACCTGTCGAGCTAGCAATCGGTCCTTTATTTAGA
GTGTTCAGATAGGCATCTGTCTTTATACAAACAATAAAGCCTCACGAATC
TTTAGTCACAAAACAAGGCAAATTAGACAGGCCACGGAGGTGTAAAGTGT
CAGCTCTGCTTATCACAACTTATCTCTGCTTTATTTGGGCACACTTTTGC
CATACAAATGGCTGATCTTGGCGCCTTTTTTTTCTCCTTGCTTTGCAGGT
AACGTCATCTCCTTCATGACCTTCCTGGCCCCGATGTAAGTGACATATAT
ATATATATATTGCTTAATTAATTATCACTGCTTCTTCAGATATATATT
CATCGGTTATTTTAATTAATTATGTGGATATGTATGCATCGTATAACAGA
CCGACGTTCTACCGCATCTACAAGAGCAAGTCGACGGAAGGCTTCCAGTC
GGTTCCCTACGTGGTTGCCCTGTTCAGCGCCATGCTGTGGATCTTCTACG
CACTGATCAAGTCCAACGAGACCTTCCTCATCACCATCAACGCCGCCGGC
TGCGTCATCGAGACCATCTACGTCGTCATGTACTTCGTCTACGCGCCCAA
GAAAGCCAAGCTGTTCACGGCCAAGATCATGGTCCTCCTCAATGGCGGCG
TCTTTGGGGTCATCCTCCTGCTCACCCTTCTCCTCTTCAAGGGCAGTAAG
CGCGTTGTGCTGCTTGGCTGGATCTGCGTCGGCTTCTCCGTCAGTGTCTT
CGTCGCGCCACTCAGCATCATGGTGAGCCCTGAGCACGCGTATAAAACTG
TGCCAAGATGCATGGACGACAGATCGATCAACCCAATCAGTTTTGATCCA
TGTGTATCGTTTCTAATGCACCGTGTTTATATATGTGTGCAGAGACGAGT
GATCCAGACGAAGAGCGTGGAGTACATGCCCTTCTCCCTCTCCCTCTCGC
TCACCCTCAGCGCCGTCGTCTGGTTCCTCTACGGCCTCCTCATCAAGGAC
AAATACGTCGCGGTAATTGTTTCATCTAATCTGCTGCAACCGCCATGGTA
TTGGTATCTCTCACTGGTCTTTACTGATAAACTACATACGATCTCTGTAC
GTATGCAGCTTCCAAACATCCTGGGGTTCACCTTCGGCGTGGTCCAGATG
GTGCTCTACGTGTTGTACATGAACAAGACGCCGGTGGCGGCGACTGCCGA
GGGCAAGGATGCCGGCAAGCTTTCCTCAGCTGCAGACGAGCACGTCCTCG
TCAACATCGCCAAGCTCAGCCCAGCCCTCCCGGAGAGGAGCTCCGGGGTG
CACCCAGTCACCCAGATGGCGGGCGTTCCTGTCAGGAGCTGCGCTGCTGA
AGCAACCGCGCCGGCGATGCTGCCCAACAGGGACGTGGTCGACGTCTTCG
TCAGCCGACACAGCCCCGCCGTCCACGTGGCATAGATTCTCGATCGATCG
CGTGCATGGCCCATGCATGCGCCCGCCACACGTACGCTAGCTTTTATATA
TTCGAAGGACGACTTGCTGCTGGTCGTGAGCATATATATGATGGAGAAAA
TGATTAAGTAGTATATATATAAGTAATTAACTGCCATGCATGGAAGCTAG
CTAATGGATGGAGGCAGAGGCCAGAACGATGAAGGGGGAAGCTATACATA
TATGTGTGTAATTAATATAGATATATGGGCTTTGTGTTCATCTTTGCAGC
TATGTATTAATTTGCATGGATATCTGTTATTCCTTTTTATGTGTAACGTC
```

| Nucleotide Sequences |
|---|
| TTCTAATAAAATGTAATTGAACCCACACTACTGTTGTTAGCTACCACAAG<br>TTTCCC SEQ ID NO: 1<br><br>ZmSWEET1a [GRMZM2G039365]<br>>lcl\|GRMEM2G039365 seq = gene; coord =<br>3:171748815..171752467:-1<br>GGCTCTCTTCTCCACCGGTCCTACCCCTTACCTCCCAAGATCACAATCCT<br>CTGCTCCTTATATATTAGCCACACCGCTCGTTCCCTGCTGCACCGGGTGA<br>CACACAGGCACAAAGACACCGCCCGTACACAGGCTCGTTGGCTTGGCTGC<br>TGTGTGTTGCGCTCAGCCATTCAGACTTGAGAGCTACTAGCTAACTGCTC<br>GTTGGGTGTGGGTGCGCTCCCGGCCTAGACCGTGGAGGAAAGGAGTCCAG<br>TCCACTCACTACCCCTCTGCTCCGTTCGGGTTCCAGGCCAGCACAGCCG<br>AGGGTTCCGCACAGCGATAAGCGCGAAGCGGAAGAGATGGAGCATATCGC<br>CAGGTTCTTCTTCGGAGTTTCTGGTCAGTATCACCATGCCATTCCTGCCT<br>CTGCTGCATGCCTACCTGATGGTCTTCTTCTTGCCTCGCCTAATCTCTGT<br>TAGATCTGTCTCCCCAGGGAATGTCATTGCGCTCTTCTTCCTGTCGC<br>CTGTGTAAGTTTTTGATTCCACGTACCTGAATCCTTCTGTTCCTCACTGC<br>CCGCGTCCATGCTTTAAAAAAAAAATCGAAAACAGAGAAGCAATGATATA<br>GTACTTACTTCTACTATATGACAAAGACTAGAACATGGGAGAATCAGTG<br>TGGAGAGAAAGGCTATAGCATCTTTTAGGTTCAATCCTTTCCAGCGAAG<br>ACTGAAATTTCATACATATATAATTTTTTCTAAAAAAAGCAAGTAGCTT<br>TTCCCCATCCGAAATGCTTCTTCTTCCCAACCACGCCGCACCTTTTTTCT<br>TGCGTCTTGCCTCAGCAGCCTTCAGGGGCAGCAGCGCAGTGCGTGTGTTC<br>CTCTGACGGGTGAGAAATCTCTTTGCAGTGTCACCTTCTGGAGGGTCATC<br>AGGAAGCGGTCGACGGAGGACTTCTCCGGCGTGCCCTACAACATGACGCT<br>GCTCAACTGCCTCCTATCGGCTTGGTAACGAACCGCTCTCTCTCTCTCTC<br>TCTCCCTGAGAGACACGGCCTTTTGATGAGCACTCCACACCATTTCTGTT<br>TCTGTCTCTTCAGAAAATTAAATCGCATCGCAGATTTATGGAGTGGCCGT<br>AAAGCAGTAAAACCGGCGTGGTGGTGTAGTTTGTTTTACTTAGATTTCGG<br>AAATGCTGCATGGTTTGCTGGCCTGGGTGAAGCAAACGCTTGGCTCCTAG<br>CGTAGCCTCTGCCCAACCCGGCCTGTCCTGTAGATAGAGTACTACCCGTG<br>GACCCACTCGCTAGACGCTAGCACTGTAAGTCTGTGACAACGACTGCAAT<br>GAAGGGGGAAAAGCTTATTGCACTGCACCACTGCCCGTGGGAGCAGAGCC<br>TACCTGTTGGCATTGCCAGGACGGAGATGACGACCTGTGGGCCTCGCGGC<br>CCTTGAGCCCGCACATGCAGCGTCACGTTCAAGTGTTCGTACCTCCAAAC<br>AAAAAAAGTCTTGACGCTTTTTTTTTCTTTGGTTATTATGATGACGG<br>ACGATTCTGGTCAGGGCATCCACATAAATATCTTAAAAGGTATTAACGAC<br>GTAAGTGCAAAAAAAAAGACAGTCTTTAGCACTACCACGGTTTTATCCAT<br>ACAACTCACGTACATGAATCATATCATGAGATCTTCTAGTGGAATAAGAT<br>ATAAAACTTAAATATATTGGGCTATATGAAAGAGTTTTTTAGATGTATTT<br>AGTGCTTAAAGAACTGAAACGTAGTATCTAGATTGTACATGTCTTTATGA<br>CTATATGGATGAGTTGGTGTCCCGTTTGATTTTTCACGCGCCTTTGAATC<br>CATGTGAAGATCGATGCTAGCTAGCTAGCTCGCTCTTCATGCGTTCGT<br>CTGGATTTTGTTTGAAATTCACGCAGCATATATGTGTGGAATATAATCTG<br>TATGCACATACAGGTACGGCCTGCCGTTCGTGTCCCCGAACAACATCCTG<br>GTGTCGACGATCAACGGACGGGGTCGGTGATCGAGGCCATCTACGTGGG<br>ATCTTCCTCATCTTCGCGGTGGACCGGCGGGCCAGGCTCAGCATGCTGGG<br>CCTCCTGGGCATCGTCGCCTCCATCTTCACCACCGTGGTGCTCGTCTCGC<br>TGCTGGCCCTCCACGGCAACGCCCGCAAGGTCTTCTGCGGCCTCGCCGCG<br>ACCATCTTCTCCATCTGCATGTACGCCTCGCCGCTCCATCATGGTACG<br>TGAGCGATGATGATTGGTTGTTGCTGCCTTGCTGGGTAGCTAGCTCCAGC<br>GGGTCCCCTTCTGGGCGTGTACGTGCGTCCTTGCTGTCAACGTACGGCAT<br>CAGTTAACAAGCTAAGCGTGTGCTTGGTGTGTGCAGAGGCTGGTGATCAA<br>GACGAAGAGCGTGGAGTTCATGCCGTTCCTGCTCTCCCTGGCCGTGTTCC<br>TGTGCGGCACCTCCTGGTTCATCTACGGCCTCCTCGGCCGCGACCCCTTC<br>ATTATTGTACGCACACGGTTCTCTCTCTAGTCTAGATCCTGAGCCGCACT<br>CACCGCCCGGCCGTACGCACGTGCTATCCGCGACATGTTGTCCGATTGCA<br>CTCGGAAACCACTGTAGCAGCACTGTATCACTAGCTGTTGGGACTGGACG<br>TAACTGCATCTGATCTGGCCAGCACAGTACCCCCGGGCTGGGCGTCGGTT<br>GCCCTTTCGATGTCCCGCCCAAGCCCAACCAGGCGCACATGCCTGCCGCT<br>GCCGCAGCCGATGCACGGGCATGGGCGCCGGTAGCGTCTAGCAGCGTGGG<br>CGTGGCCACCCACAGGCAGCGCACGCCGGTGCTAGCTGCCGATGGGCCGC<br>CGTGCCCATGTCCATGCAGCTGGATTGGACCCGGCACAGGCAGAAGCAAC<br>AGCGCCCGCGCTCTTTCTTGTCGCAATGCTAGTTAGCAAACTGCACGGTG<br>CACTCCACTTCAGTACACACCAACGCGACAGACTGCGATGAAATATCTAA<br>GGCCGAGTTTTTTTTTTGCAAATCTCATCATGTCGGAATGATTCATGC<br>GGTCCAAACTTCAGCACACCCCCACTGTCGCTAAACCCGCGCTGTCTGTG<br>CATGCGTGCAGATCCCGAACGGGTGCGGGAGCTTCCTGGGCCTGATGCAG<br>CTCATCCTGTACGCCATCTACCGGAAAAACAAGGGCCCCGCCGCGCCGGC<br>CGGCAAGGGAGAGGCCGCCGCCGCCGCGCGGAGGTGGAGGACACCAAGA<br>AGGTGGCCGCTGCCGTGGAGCTGGCCGATGCCACGACCAACAAGGCAGCG<br>GACGCGTCGGCGGCGACGGCAAGGTCGCCAGCCAGGTGTAGGCGGGCAA<br>GGCTTATTTGCTGTCTGGGACTGGGAGGAACATCCTAAACGAGGCTGCCT<br>TAGTTTCTTGGTGGAGCAGATTGGTGTTGGTTTCTGTGGGCTTTTACGGT<br>TGTTGTTACTCTCATCTCCATCTCTCCCAGGAGGCTACCCCAAGCATGTA<br>GTAGCTTCCATTCTGATTCTGGGACGGTGTTGCACGTTACAGTGCTCTCA<br>AGCTGTCTCTGCAAAGTGTGTTTTTTATTCCATTTCCTCCTGCTCTTG | TTCTCCAACTGCGCTTACCTGCCCCCGATTTCTCTAAAAAATGTATTAAA<br>CTATCTGAGAAATTCATCCAACTGCGAGTACTGTGCTGTGCGTGAGCAAT<br>GC SEQ ID NO: 2<br><br>ZmSWEET11/MtN3 [GRMZM2G368827]<br>>lcl\|GRMEM2G368827 seq = gene; coord =<br>1:194932443..194935353:-1<br>ACACACAAACACATCAGCATTCAGCAATAGCTAATCGAGCATCGTCGCCT<br>TAGCTCCTCTCCTCTCCTCTCCGTCGTCGTGGAACTTCTCTCCGCCGGCT<br>GTCATATATATAAAGGAGAAGAAGAGAACAGCAACTCTAGCTAGCCGGCC<br>GGCCTCCGTCGTCGCCGGCGTCGTCGACTAGCTAGCTAACTCTCGATCTC<br>CAGTTCCTGCCCCCGCGCCCCACGCCCGGCCGTCGTCGTCAGCAATGGCA<br>GGAGGCTTCTTCTCCATGGCTCACCCGGCCGTCACCCTCTCCGGCATCGC<br>AGGTACGTACGCGCCAATGAAACAACAACGTCGTCTCGAGCTAGATCGAT<br>CCATGCATGACGCCGGCCGGGACCGGCCGGATAGATAGGCGGAGATCGAC<br>TTGCATAATGCTTCGCGTGTTTGGCCTTTTCCTGGTGCTTCTTTTTTTTT<br>TTAAAAAAAAATCTTATGGGACCTTGATGAATGCTTTTCATGTGGTTTTCA<br>TTCATTCTGTTGCCGTACTACGTTCTTCTAGATTTTGTTTATTCCGACAT<br>GACGACTGTCTTGTCCATCCTTGTATCATCGATCCGTCCTTTGCATGCAT<br>GCATCCACCAGTCGTCAGCCTTCCTTTTTGCCGTTTGTGCCATTGCACTG<br>TAGAGCACGCACGCACTCTCTAGCTGTAGAGAGGCGCAGCAGTAGGCATG<br>CATGCAGCAGCTAGTCACACTGGACAACCAACTGTCTTGTCCATCATCTA<br>TCAACAATACTTGCATATCAGAATACGTAGTATGTAGCTTTAGCATTTTT<br>TTTTCTTCACCTATACTACTGCTAGCTGCATCTTCTTGAACTTTCTCTGA<br>TGCTCCCCGCGGCCCATTGAGACGACGATGCACTCTTTCTCCAATTCGTT<br>AGCTGCGATCATGGCACAGGCCTTTAATTTGTTGCTAGCTAGAACACACA<br>TGCATGCATCGCCGAGGTATAGCAACTTTTCCACTCAAGAATAATGGTAA<br>TAAGCAGTGCAGATCAGATCCACATATTGGGCATTAGATCACGAAATACA<br>GTTGCAAATAGCTGCTCACACGTAACGCACTATCTAAGAATCATTTCTA<br>TATACGTGTATTTTTTGCTGGAATGGTTATGATCGATCGGTTGGGCATGC<br>AGCAGGGAAGGCGTGTGCGTGTGCATGCAGCTACCTAGCTTTTTGCCATA<br>TCAGCGTTTCCTTAACCTAATCACCACGCTTCTCTCTGTTAGTGGACGCA<br>CACGCATTGTACATATATATGTGTATAGTATTGTTACTCCTACCACTTTA<br>CTGAAAATGACGACACTGACGCGTAGTTACCCTCTTCTCTCTTGTTTCTT<br>CGATTTGGATTGTGCAGGAAACATCATCTCCTTCCTGGTGTTCCTTGCAC<br>CAGTGTAAGTAGCTAACTGATCCACCACCTTTCTTCGTTCCTTACTGTCTCA<br>ATTTCAGACCGACTCGGATTCATGCGTGAATCGATGGATGATCCAAGACT<br>GACATGGCATGCCTCTTGTACGCACCGTACCAAAACAGGGCGACGTTCC<br>TGCAGGTGTACCGGAAGAAGTCGACGGGCGGGTTCAGCTCGGTGCCGTAC<br>GTGGTGGCGCTCTTCAGCTCGGTGCTGCTGTGGATCTTCTACGCGCTGGTGAA<br>GACCAACTCGAGGCCGCTGCTGACCATCAACGCCTTCGGCTGCGGCGTGG<br>AGGCGGCCTACATAGTCCTCTACCTGGCGTACGCGCCGCGGCGGGCGCGC<br>CTGCGGACTCTGGCCTACTTCTTCCTGCTGGACGTGGCGGCCTTCGCGCT<br>CGTCGTCGCCGTCACGCTCTTCGCCGTCCGCGAGCCCCACCGCGTCAAGT<br>TCCTCGGCAGCGTCTGCCTCGCCTTCTCCATGGCCGTCTTCGTCGCGCTG<br>CTCAGCATCATCGTCAAGGTGGTCAAGACCAAGAGCGTCGAGTTCCTGCC<br>CATCAGCCTCTCCTTCTGCCTCACGCTCAGCGCCGTCGCCTGGTTCTGCT<br>ACGGCCTCTTCACCAAGGACCCCTTTGTCATGGTAACGACTGATCAATAA<br>TGTAATATATGGTTAACTGATCCATATATATATATAAAATGGTAACTGAA<br>TAATGCTGGGGATGTTTCTGATTATATATATCTATTCAGTACCCCAACG<br>TCGGCGGCTTCTTCTTCAGCTGCGTCCAGATGGGCCTCTACTTCTGGTAC<br>CGCAAGCCCCGCCCGGCGGCCAAGAACAACGCCGTGCTGCCGACGACCAC<br>GGACGGCGCCAACGCGGTGCAGGTGCAGGGGCAGGTCATCGAGCTGGCGC<br>CCAACACGGTGGCCATCCTGTCGGTGAGCCCCATCCCCATCGTGGGCGTG<br>CACAAGATCGAGGTGGTGGAGCAGCAGCACAAGGAGGCCGCCGTGGCCGC<br>CGAGACCCGCCGGATGGCCGCCGCAAACCCGGACGGCGCCATGCCGGAGG<br>TCATCGAGATCGTCCCCGCCGCCGCGCGGTGCACGCCAACGCCAATCAC<br>CATGCACCGTACACACCCTGCTAGCTTCTTATTAGCTAGCTCGGATGACG<br>TACGACAGTTTGGTGGCAAGTGGCTGGCAGCTCAAGCATGCAGATGCAGG<br>CATCGTCGTCTGCTAGTTGATCGTTTAGTTGGTTAATTGTTGGATTATTA<br>TTGCTGTCTCTCTCGTGCTGTAGTCTTTGTCAGTTCAGTTCAGTTTCAGT<br>GTCGAATCAAGTAGTAGTAGCTGTTGTTTGCATTGGATCTGACAATGCAT<br>GCTAATAATTATGGTGGTGTGATGGTCTTGGTCGGTACGTGCGTAGTCGT<br>CTACGTACGCCGTGTCAACGTCGTAGATCTACGGGAAGATGATAAGAC<br>TGTAACATGCAGGGCATGCATCTATTTATACTTAACATATTCTTTGTGTG<br>CTTAATTTT SEQ ID NO: 3<br><br>ZmSWEET16b [GRMZM2G111926]<br>>lcl\|GRMZM2G111926 seq = gene; coord =<br>8:33363546..33368983:-1<br>CTGAGCTGACTGTGGATCTCATCCGTATCGTATATACGTCGTCCTTTTTG<br>GATCCACCGCTGTTTTTGCTAATTCCCTTCGAACCGGCCGGTGGCCTTCGTT<br>CTCCCACCAGGCCTGTCTGTCTGCTGTATCCGCCAGAGCTTCCATGGATT<br>CCACCCTCTTCATCATCGGCGTCATAGGTAAGCTTGTGTATCATTCTGAA<br>CTGCTTTGTTATTATTATTAGTCTTCATTCGTCCAGCTTTCCTTATCTTC<br>TTCTTCTACATTGAAATAGGCAACATCATCTCAGTTCTCGTCTTCATATC<br>GCCTATGTAAGTGTCTTTCTCCATATATATGGTTTCCCTGTCGTCGCTGT |

Nucleotide Sequences

```
TGCTAGCTAGCTTTCTTTCTGAACACCACCACGGGCACCAATCCATGCAT
GGATACAGCAAGACGTTCTGGAGGATCGTGCGGGGCGGGACGACGGAGGA
GTTCGAGCCGGCGCCGTACGTGTTGACGCTGCTCAACGCGCTGCTGTGGC
TCTACTACGGCCTCACCAAGCCTGACGGCTTCCTCGTCGCCACCGTCAAT
GGCTTTGGGGCTGTCATGGAGGCCATCTACGTCGTCCTCTTCATCGTCTA
CGCCGCCAACCATGCCACAAGGGTGAGGGGTCGGAGCAGCTGGGGCCAGT
ATATATAGTTCACTCACACAATCCGTTGCTTAATTCTGCATAATTCTTTC
TTCAAGCACTTGAGTCTTAGGAATTACGGAGTATATAGTTAAAGAAAAGC
ACAACCACCATTCGTTTATTAAAGAAAAGCATGTGTTGCCTTATATTATA
GTTTGTTCCTTTATCGCAATTATGATTATGCAGGTTAAGACCGCGAAGCT
GGCAGCAGCGTTGGACATCGGTGGCTTCGGAGTCGTGTTTGCGGCCACCA
CATTCGCCATCAGTGAATTTGAATTGAGAATTATGGTGATAGGAATGATA
TGTGCCTGCCTCAATGTGCTCATGTACGGGTCACCCCTTGCTTCTATGGT
AAGTTTTTTTTCCTCACATGCATATTTATACACTATTCCTCTTTTCTTTC
CTTTTTTGGTTATTTTAGAAACTTAAATCCCCTCTGGTATTAATTCCCGA
GAATTTCACTTAATTCCCAAGAATCCCAAAAAAAAATTAAGTTTCTAAACT
AGCCCTTAGTGAGACTTAATTTATTTGTTCGCCGTAAGTCGATTTTGAGA
TGCACATTTCTCCTTAATTTTCCITTTATAGCTGACCGTGCACGGCCTTG
AAACATCACGATCTTTTCAGTTAAATTTAATTAGCACGGGCTAAATTTTT
ACATTGCAAAAGAAAATAAACTAATTTCACACACATATAGTAGTATA
GCTAGCAAACTGCTAATGGGCCAGCAAAACTTATGGATGATAACATTGAG
CAATGAAATTATTGTCATGTAACGGTAACTATATTATAATAGTGAGTTTC
GATCCATGATCTAATATATACCATATAATAATATTGATGCCACTTGGCCC
CACAGACAAAGTAGAGTATAGTTCAAGTTTGGAGATATAAATAATGATAAT
AATAATAATAAAGCTGCTCAAGATATTTTCATTCTGGCGATCCATGTCTG
TCCACGATGGATCGACGATAAAATACTCGGTGTTTATTATAATGGACAGG
GCGCTTTGTGGGGCGATTATTTTATGTGTGTGTCCCTTTCATGATTAT
TTATTAAATATAAGGACAGAAGTCCAAGCAAAACACATGTGCCCAAGGA
ATAGGGATATATAGTACATATTGTGGAAATAGTTATATATTTTGGGGGA
GAATCATGTGTCAGGGATATTGTACAATAGAAAACATTTCTTAGTATGT
AGGTCCTCAACTGCCCCTGTTTTTTCTCTTATTTTAGCAGATGTTCGAT
CCACTTCCACAATTCCACTTGCAGGAATAATATAATAAATATAGATATAT
ATGGTACATAAGCTGTATGTAAAATCATATAATAATAATTAATATTCAT
TATATACCTCAACGAATCATTTCTAAAGCTTTTATTAGGTATAATAAAA
GTAAATTTATATTTTGGTGCTTGTAGCTAGGTGTGGCCGTGTGGGCACG
TGCAAGCAACCTTACTCGTTCCACCTCCTATCTTTTGCTCCACTTTGTAA
ATAATACATATTACAGCGTAAAACTGTGTAGAAAGTATGATTTTACGGCT
ATATACACGGTGTGCTACGACTAAAAGTTAGGGACGACCTCACGCCGATA
ATTGGATGACAGATTTTTTTCCTTTGATATCTTTCTTCTCTGGCATGCCA
AATCGAATTCCTCCCTCTGCCTTTAATTTCTATTTGTTAGGATTATATGA
AACTATTTCCACAAGTATAGTTAGAGACTCAAATTCAGATACTAGAAATT
AATGATGGTTTACAAGCCATAAATAAATAAATTAAAAATAAACATATTTA
GATTTTAATTTGAATGAAAAGAGAACATTGCTTCGGTTTGATGCAGATTA
ACTTATACAGAAATCATATATTTATGTCATGAGAGACAAGCAAAGATTGGT
CAACTTATTACCATTTCTTGCAAAATCAAGTTTGCCGTATTATTATTTTG
TCCTTTTCTTTTTTAAAAGATTATTAGCTGGTTATTGGTTCTCTGGGCAG
TTAACGGGGTAGAGTATTCCACAGAATTAAATAATCACCATGCAAGGAAC
ACGCGTTGTCCTCTACATACGATTCTTTATTTACTTAATTCTACATCACA
CATTTTGTGCAAGAACGATAGCTATTAGAAAAAAATGTGAGCATCGGTT
CACAACCGGCTATAGTACTGGATTATCAACTGATATTAGACAATCGAAAT
TAAAGACCTTATATTTGAAGGACCGGTGAAATGACCAGAAGGGGTGAATT
AGAGCCAATCAAATTTTATTGTTAAAAACTTAAATTTAGACCTTATTTGT
GAAGGACCAGAAGAGGTGAATGAGAGCCAATCAAATTTTATTACAAAAAA
CTAAAATTTAGCACTTAACTTCAATTGAGATGAAGAAATCGTTCAAACCA
GAAGCACATCGGCCAAATAGTAATCTTACGATTTCAAATGGTACCCCTA
GATACATTTGGTTTTTGTTTAGAATACCGGTATTCTTTGGCTAAGTTCA
TTTGGTTTATTGGTTTTTGTTTAGAATATGGGTATTCTAAACAAAAACCA
AATGAATTTTGCCAAAAGAGATGGATGTCAATAAAAGCCCACATATCTAT
TTATAGAGGTGATGGATACATCATATCCACTTAGCGGGGCAAAATGGAT
CAACTCCTAGGATTTTGATCAGACGACCACGCGCTCTACACAAAGTTGCT
TCGCCTCGACACACCCTTTGTGATGATGTGATGTCATGTGCCACCTCTGATTCCT
GCCGAAACCGCCACCGTCAAGTTTTGAGGCCCAAACTCAGCAAAACCAGC
AGATGGGTGGTTTTGAGGCTCAACACAAAACCACCGCGAGTAGTGCATC
GCATGCGCGTCCCCACGTCCTGGACACATGTCCCATTAGTCCTTGACCGG
ATCGGCGACAGTGCGACACAAGCCACTCTGTCATGTCCTCGCGCTAGTGC
GTGTCCTAGGTGTGAGCCACCACAACTTGTCAACCGGCTCCTCCGACCCC
TTGGTCAAGTCCTAGTGCTCGTCTTTCATCACTCTCCGTCTATCGGCATA
AACCCTCGTGTGACCTTCACATTCGCCATTGAACACATACATGTACTTC
ACACCTGCACACCATAAGCCGAGAGACATGGTTGCACAATACATAACTCA
TACTCTGGTCAGTCCACCGACTACATCAAAATACTATCCGTTGACAATCA
CTTATCATCAACTCGAACACAAGGGACAAATCAACTTCAACTTGTGTTCCAATT
GTTTGCCATAGAGAGAAAGAAAGCGTACTCCGTGTGTTGCTTGGGTTTAC
CGAGAAGCACGTGTGTAAAATGGGTAGCATACTCTAGTAGTACTACGAGT
GCACGACGTGACTCCTACAGATTCAAACTCTTGGCAAAATTAATATCGC
GACATGTCATCATGTCCATGCCATTACCTTAGCTGTATTGACAGGCCGGA
CCTGCTATTTGTGTCGGCCGTACGTGTTCTTGCGGTCCTCGTCGGGTGGG
GTTTCGCTCTCTGAATTTTCTGATTGGTTCCATCGATATTTTCTGATTGG
```

```
TTCCATCGAAAGCGAAACCAGGACCGTACGTGGCGCCAAATTCAACCAGA
CCACCCATCCCTTCCCGGGGTCATGTCACATCCCTGTTGCTTCACGTTTT
CTTACAAAATTACCCGCTCCGTCCGTGAAGCAAATATAACTATGATATCC
CTATCTGTCAGAGTAGTTTAAATTTAACTAAATTTATAATAAACAATACT
CGCTTTGGTCCTAAATCTAGACACATATATATATATATATATATATATAA
CACATACATCAAGTATTGTATAAATTCACAAAATACCACTATATGAACGC
CCTTAAATTTTAAATTAAAAAATTATCTAAGAAAACATAAGCAATAATTA
ACCCATGCCAATGCAAGTTGAATACTTGAATTGAAAAAAGTTGATTCCAG
CTCAGGGAACCTATAACCATGGCTTCGCATGAGTTGGCGATTGCCTGAAC
AGGCCCATGCAGAGCAACTAACCATAGAATAGAACAATACGCGATGAAAT
TCACCGTACCCTGCAACGTAATGGATGTGTGATTAGTATCACCGGCACCT
CATTTTTACCCGTCATCTCGTTGTACCTACATTTTCAGAAAACGGTGATC
ACGACAAAGAGCGTGGAGTTCATGCCATTCTTCCTGTCCTTCTTCCTCTT
CCTCAACGGAGGCGTCTGGGCAACGTACGCGGTGCTTGACCGCGACATCT
TCCTCGGGGTAATGTTTAAAGCCTCTCTGTTCTTCTCGATCTTCTTCCCC
AACCTCTGTCTTTTCCGCTACCCATACTAAACAGAACCTCTCGATCGCTC
TCTGCATGCAGATCCCCAATGGGATAGGCTTCGTGCTTGGCACCATCCAG
CTGATCGTCTACGCGATCTACATGAACAGCAAGGCCTCCCAATGCAGCAA
AGAAACAGCGTCCTCGCCTCTTCTGGCCTCCGACCGGGGAGAAGCATCTA
GCCATGTCTGATGATGAGCTTCGATCAGTGCGCGCGCTGGAGATAGCAT
AGAAGTCTCTTGCTGTCAAAAACTTCCAAGACCAACGGTACCTACCAGCA
TGCATGCATGCAAGAGGTTACCAATTTTTATTGTTTGAAAATTCATGTAA
ACTTGTGACCTCCATGGATTGTTTCTTTCTTTGGTATAAGCTTCGAAGAT
GTTAGATTGTTAGCACGGTAGTTTTGCCAGAGAAGGGTGTTGTCAATATA
ATGAAGAAATGGTGAAAATCCATACATTTGATTATCGA SEQ ID
NO: 4

ZmSWEET15b [GRMZM5G872392]
>lcl|GRMZM5G872392se = gene; coord =
5:164854921..164858109:-1
CTCAGGAGCTAATGACTCACCTCTCCGTGCTCACCTCCTCTTCTTGAGGC
TTGAGCTCTCTTCCTCTCTCCCCTCAGCTCATCTCCACCGTCTCCCTA
TATATAGGATGCTCTGCCGGCTCCAAGGTTCCCAAGCGCCCAAGGCAGCG
GAGAGAGCTAGCTCCCTCCTCCTCCTCAGGTAGCGAGCGAGCGAGCTCCT
CTGCCCCTCTGCACACCTGGCCTCCCCTTCTCCGCTGCAGGACCGCCGTT
GACGACTGCTCCACCAGTACTGCGCGGCCCCGCGCTGCCTACCCTTACCT
AGCCAGAGCGCGGCGCGCGAGAGGGAGAACGACCAGGAGGGGAGGAGATC
GATCGATCGATCGATCGAGATAGATGGCTTTCCTCAACATGGAGCAGCAG
ACCTGGGCCTTCACCTTCGGTATCCTAGGTACATATATACTGTCAGTCTG
TCACTCGTAGCTACTAATTAACCGCATCAACGGAGCCGCCCTGCCGTCTT
CGTCCTCGTCAGTGTTTCTGCATTGTTTTCTTCCTTGTCCAAGTCCTT
TGAGACGCACGCATACATGATACATGCATGGCATCATCGTCTCCCAAGTC
CTAGGTACAGTTTCATCACCGCGCGCCTCTCTCAGATATGTGTCGTCGTA
CAGGACAACACAACACGTCCTCGTCAATCTACTAGCTATATGCGCTAATA
ACCACCTCTTCCTTTCCGAGCCACGGCACAGTATAGCCTGCCATCCGAAC
GAACGGAACCGCCCAAAACCCAACTTTTTTGGGCGCTAACTAATGCGGTG
GTTAGCCCAAACAAAGAAACCAGGGCAGTCATACATTTTACATGTAGTAC
CTGCTTGACGACGGGAACCAACACAACGGCGCGCCGCGAGGAGAGTTTGT
TCCATTTCCTCCGCCTGCAGCTAGCTGCAGCTAATAACCCCGGCCGCCG
GATGTTCTCCTTCTCGCATGCTTTTTTTTGGGGGGTTCTTTCTCCGCCT
CCTGCTCTTCGTCTGTTCTACCATCGTCGATCACACAGCAATTTGACTGA
CCGCGTCTGTCCTTCCGACCTTGCCGTTTTGCTTTGCAGGTAACATAATC
TCGCTGATGGTGTTCCTTTCGCCGCTGTAAGTAACTCTCTGCTTTAATTT
ATTTAACCTAGCCGTGAACTTTTCATATTTACGTTTACAGTATCCAGTAC
CATGCATAATATACTACCAATATGTTTCTATGTATATTCAGTAAAGGGAA
GCGTCCAAAATATATACTGCCATCAGGTATGATGAGAACATATATATAAA
GAACATGGCACGCACGCATGCGTATCTCACTGTTGAATGAATGACGTGCC
ATCATCGTCCATGCTCTTCTAGATCCTTTTCCTTTAATTTATGCGTGGTT
CTAGATCCCCTATATATATATATATATATATATATATATATATATATATAT
ACGTACACCTGAAGACAACATAGCTAGCTAGGAAATAAACTCGTTGGGAA
TTGAATTGCTGCATTAATAACGTACTTTAATCAGTTGCGAGCCAGTACG
TGTCACTGTTCGGTGGTTGCGTTGCACATGCTTTTAGTATGGAACAGCGC
ACGCAATCTAGTAATAATTAATCTAAAAAATCACACGGTAAAAAATATTC
GTTCCCGCTGATCCCGCGCAGGCCGACGTTCTACCGCGTGTACCCAAGA
AGTCGACGGAGGGGTTCCAGTCGACCCCGTACGTGGTGACGCTGTTCAGC
TGCATGCTGTGGATCTTCTACGCGCTGCTCAAGTCCGGCGCCGAGCTGCT
GGTGACCATCAACGGCGTCGGGTGCGTGATCGAGGCGGCGTACCTGGCCG
CGTACCTGGTGTACGCGCCCAAGGCCGCCAGGGCGCTGACGGCCAAGATG
CTGCTGGGGCTCAACGTCGGCGTCTTTGGACTCGCCGCGCTCGCCACCAT
GGTGGTCTCCAGCGCCGGCCTCCGCGTGCGCGTGCTCGGCTGGATCTGCG
TCAGCGTCGCGCTCAGCGTATTCGCCGCGCGCTCAGCATCATGCAGCAT
ATCTAATTTAATCTCTCTCTCTCTCTCTCTCTCTCTCTCTCTCTCTCTCT
CTCTGAAGAGGGATGTGAATTGTTGGAACCGCCATTAATTCGCTGACTGC
CCTATCTACATCTACTTTCCTGCAGCGGCAGGTGGTCCGGACCAAGAGCG
TGGAGTTCATGCCCATCTCGCTCTCCTTCTTCCTGGTGCTGAGCGCCGTG
ATCTGGTTCGCGTACGGCGCGCTGAAGAGGGACGTGTTCGTGGCGTTCCC
CAACGTGCTGGGCTTCGTCTTCGGCGTCGCGCAGATAGCGCTGTACATGG
```

Nucleotide Sequences

```
CGTACAGGAACAAGGAGCCCGCGGCGGTGACGGTGGAGGAGGCGAAGCTG
CCGGAGCACGCCAAGGAGGTGGTGGTGGCCGCGGCGGCGGCCGAGGCCAG
GGCGAGCTGCGGTGCTGAGGTGCACCCCATCGACATCGACATCGAAGCTA
CGCCGACGCCGGTGGAGGAGGTGCACGAGCCGCAGGTGGTCGTGGTCGTC
GACGTGGACGTGGAGCCTGTCACCTGCGCCGGCGCCGCCGAGGCAGCTGC
GGGAGCAGGGGCAGATGCGTCCGGCGTGGCCGACGGCGGCGTCCCTGGAC
CCATGGCGCCGCCGGAGCAGCTGGCGATCAAGCCCGACATGGCCATTTCC
GTGGAGGCGTAGGTTGGTTAAAGTGTAATAGCAGAGTGAGTCGATATCGA
TCAGTAGTAGATTTGTCGAGTCAAGGAAGGGGCCTGCTGCTGCTGCTACG
CGACAGCAGCGGCCAGATGTACTGCCTGCATGCATGCAGTCCCTCCCGTT
```

Nucleotide Sequences

```
GACTCGACCCGTAGAGAAGGGATGGGATGGAAGTAGCCGGGTCCTTGGGC
GAGTAGCGGCGCCTTGGCACCCACGGGCCAGCCGTACTGGCCTGTGTGAT
GAACCGGCGAGAGAGATGAGATAATGTGCGAGCGAGAGAGGGTTGGTTGG
GTTGTGGTAGTTGAAGAAGACGGCTAGCTAGCTGCTGCTGCTGGGCTCTC
TATCTGTCTCTAGATCTGTGTATGTCTGTGTAATCGAGGATTCCCTCACC
TTGCATGCCGCCTCCCTTTTGTGTCCTTCTAGTCTGATGATTGTTTTCAT
TCCATCCATGCCGGCGTCGCAGTAATAAAATTTTTTTGG SEQ ID
NO: 5
```

That which is claimed:

1. A method of producing a maize plant having increased yield under non-drought conditions, increased yield stability under drought conditions, and/or increased drought tolerance, the method comprising:

crossing a first maize plant with a second maize plant, wherein said first maize plant comprises within its genome a marker associated with increased yield under non-drought conditions, increased yield stability under drought conditions, and/or increased drought tolerance in a maize plant, wherein said marker is located within a chromosomal interval on chromosome 10 defined by and including base pair (bp) position 14762443 to base pair (bp) position 14765098 (Gene Model ID No: GRMZM2G173669), wherein chromosome 10 bp position 14762443 comprises a G allele; chromosome 10 bp position 14765098 comprises a C allele; chromosome 10 bp position 14765012 comprises an A allele; chromosome 10 bp position 14764839 comprises an A allele; chromosome 10 bp position 14764763 comprises a G allele; chromosome 10 bp position 14764762 comprises a C allele; chromosome 10 bp position 14764658 comprises a G allele; chromosome 10 bp position 14764415 comprises a G allele; or any combination thereof, thereby producing a plant comprising one or more of said alleles, and having increased yield under non-drought conditions, increased yield stability under drought conditions, and/or increased drought tolerance.

2. The method of claim 1 wherein a combination of two or more markers associated with increased yield under non-drought conditions, increased yield stability under drought conditions, and/or increased drought tolerance in a maize plant are detected.

3. A method for producing a hybrid maize plant having increased yield under non-drought conditions, increased yield stability under drought conditions, and/or increased drought tolerance, the method comprising:

(a) identifying a first maize plant comprising a first genotype by identifying a marker, wherein said marker is located within a chromosomal interval on chromosome 10 defined by and including base pair (bp) position 14762443 to base pair (bp) position 14765098 (Gene Model ID No: GRMZM2G173669), wherein chromosome 10 bp position 14762443 comprises a G allele; chromosome 10 bp position 14765098 comprises a C allele; chromosome 10 bp position 14765012 comprises an A allele; chromosome 10 bp position 14764839 comprises an A allele; chromosome 10 bp position 14764763 comprises a G allele; chromosome 10 bp position 14764762 comprises a C allele; chromosome 10 bp position 14764658 comprises a G allele; chromosome 10 bp position 14764415 comprises a G allele; or any combination thereof;

(b) crossing the first maize plant and a second maize plant not comprising the marker of of (a) to produce an F1 generation; and c) selecting one or more members of the F1 generation that comprises a desired genotype comprising any combination of the markers of (a), whereby a hybrid maize plant having increased yield under non-drought conditions, increased yield stability under drought conditions, and/or increased drought tolerance is produced.

* * * * *

SEQUENCE LISTING

<160> NUMBER OF SEQ ID NOS: 19

<210> SEQ ID NO 1
<211> LENGTH: 2656
<212> TYPE: DNA
<213> ORGANISM: Zea mays

<400> SEQUENCE: 1

```
gcctatataa agccacccac agccctgcct atcattgcaa gagtttgagc caacacacac        60
agagagagga caactcctca caactctccc ttccctcctg taggggccaa aagggttaga       120
gagtaggaga agtagttccc tagcccaaca caagaaaaac aagctcgatc tcctcatcac       180
cctaatccaa gcaactgctt tgtgtgttgg gaaattcttg tgacccctgt tatattatta       240
tccgtgtagc tactagcttc attccccct ttgtacccat caaatggctg gcatgtctct        300
gcaacacccc tgggcgtttg ctttcggtct actaggtaca tactacacct tcactaatag       360
ctaaacaagc gcccgccgca aagctatgaa ttaagggcag gcatgtttgg tttgctacct       420
attttaccat acttttgtcta actttctgt ctaaggttat agttcttcaa ttcgaacgat       480
taatcttagc caaagtgtga catggttagc cacgaactaa gcaggcccct aattattgcg       540
catgtatata ttatatattt atctttctat tctgtttaat ttgttttctc tttacatata       600
tatactacta tgtaagtata tattatatgc acaacaagca ggcctccttc gtgcacatat       660
gcatagaatc aatctatacc cttcatagaa gccactttga gatatacctt ccaaaacaat       720
cccaaaaaca agacgctcga tcttgcgctc acaatcactt agttttgcac cagattaagc       780
atgcaccact agattttatg tactgtatta cctctgccat ccatggtcga tcctttagtt       840
tatcctattc atttccgtca tgaactacct gtcgagctag caatcggtcc tttatttaga       900
gtgttcagat aggcatctgt ctttatacaa acaataaagc ctcacgaatc tttagtcaca       960
aaacaaggca aattagacag gccacggagg tgtaaagtgt cagctctgct tatcacaact      1020
tatctctgct ttatttgggc acacttttgc catacaaatg gctgatcttg gcgccttttt      1080
tttctccttg ctttgcaggt aacgtcatct ccttcatgac cttcctggcc ccgatgtaag      1140
tgacatatat atatatatat attgcttaat taattatcac tgcttcttca gatatatatt      1200
catcggttat tttaattaat tatgtggata tgtatgcatc gtataacaga ccgacgttct      1260
accgcatcta caagagcaag tcgacggaag gcttccagtc ggttccctac gtggttgccc      1320
tgttcagcgc catgctgtgg atcttctacg cactgatcaa gtccaacgag accttcctca      1380
tcaccatcaa cgccgccggc tgcgtcatcg agaccatcta cgtcgtcatg tacttcgtct      1440
acgcgcccaa gaaagccaag ctgttcacgg ccaagatcat ggtcctcctc aatggcggcg      1500 tctttgggggt catcctcctg ctcacccttc tcctcttcaa gggcagtaag cgcgttgtgc      1560
```

```
tgcttggctg atctgcgtc ggcttctccg tcagtgtctt cgtcgcgcca ctcagcatca    1620
tggtgagccc tgagcacgcg tataaaactg tgccaagatg catggacgac agatcgatca    1680
acccaatcag ttttgatcca tgtgtatcgt ttctaatgca ccgtgtttat atatgtgtgc    1740
agagacgagt gatccagacg aagagcgtgg agtacatgcc cttctccctc tccctctcgc    1800
tcaccctcag cgccgtcgtc tggttcctct acggcctcct catcaaggac aaatacgtcg    1860
cggtaattgt ttcatctaat ctgctgcaac cgccatggta ttggtatctc tcactggtct    1920
ttactgataa actacatacg atctctgtac gtatgcagct ccaaacatc ctgggggttca   1980 ccttcggcgt ggtccagatg gtgctctacg tgttgtacat gaacaagacg ccggtggcgg    2040
cgactgccga gggcaaggat gccggcaagc tttcctcagc tgcagacgag cacgtcctcg    2100
tcaacatcgc caagctcagc ccagccctcc cggagaggag ctccggggtg cacccagtca    2160
cccagatggc gggcgttcct gtcaggagct gcgctgctga agcaaccgcg ccggcgatgc    2220
tgcccaacag ggacgtggtc gacgtcttcg tcagccgaca cagccccgcc gtccacgtgg    2280
catagattct cgatcgatcg cgtgcatggc ccatgcatgc gcccgccaca cgtacgctag    2340 ctttttatata ttcgaaggac gacttgctgc tggtcgtgag catatatatg atggagaaaa   2400
tgattaagta gtatatatat aagtaattaa ctgccatgca tggaagctag ctaatggatg    2460
gaggcagagg ccagaacgat gaagggggaa gctatacata tatgtgtgta attaatatag    2520
atatatgggc tttgtgttca tctttgcagc tatgtattaa tttgcatgga tatctgttat    2580 tccttttttat gtgtaacgtc ttctaataaa atgtaattga acccacacta ctgttgttag    2640
ctaccacaag tttccc                                                    2656

<210> SEQ ID NO 2
<211> LENGTH: 3653
<212> TYPE: DNA
<213> ORGANISM: Zea mays

<400> SEQUENCE: 2
ggctctcttc tccaccggtc ctaccccctta cctcccaaga tcacaatcct ctgctcctta     60
tatattagcc acaccgctcg ttccctgctg caccgggtga cacacaggca caaagacacc    120
gcccgtacac aggctcgttg gcttggctgc tgtgtgttgc gctcagccat tcagacttga    180
gagctactag ctaactgctc gttgggtgtg ggtgcgctcc cggcctagac cgtggaggaa    240
aggagtccag tccactcact accccctctg ctccgttcgg gttccaggcc agcacagccg    300
agggttccgc acagcgataa gcgcgaagcg gaagagatgg agcatatcgc caggttcttc    360
ttcggagttt ctggtcagta tcaccatgcc attcctgcct ctgctgcatg cctacctgat    420
ggtcttcttc ttgcctcgcc taatctctgt tagatctgtc tccccaggga atgtcattgc    480
gctcttcctc ttcctgtcgc ctgtgtaagt ttttgattcc acgtacctga atccttctgt    540
tcctcactgc ccgcgtccat gctttaaaaa aaaaatcgaa aacagagaag caatgatata    600
gtacttactt ctactatatg acaaagacta gaacatgggg agaatcagtg tggagagaaa    660
ggctatagca tctttttaggt tcaatccttt ccagcgaaac actgaaattt catacatata    720
taattttttt ctaaaaaaag caagtagctt ttccccatcc gaaatgcttc ttcttcccaa    780
ccacgccgca cctttttttct tgcgtcttgc ctcagcagcc ttcaggggca gcagcgcagt    840
gcgtgtgttc cctgacgggg tgagaaatct ctttgcagtg tcaccttctg gagggtcatc    900
aggaagcggt cgacggagga cttctccggc gtgcccctaca acatgacgct gctcaactgc    960
ctcctatcgg cttggtaacg aaccgctctc tctctctctc tctccctgag agacacggcc    1020
```

```
ttttgatgag cactccacac catttctgtt tctgtctctt cagaaaatta aatcgcatcg    1080
cagatttatg gagtggccgt aaagcagtaa aaccggcgtg gtggtgtagt ttgttttact    1140
tagatttcgg aaatgctgca tggtttgctg gcctgggtga agcaaacgct tggctcctag    1200
cgtagcctct gcccaacccg gcctgtcctg tagatagagt actacccgtg gacccactcg    1260
ctagacgcta gcactgtaag tctgtgacaa cgactgcaat gaaggggaa aagcttattg     1320 cactgcacca ctgcccgtgg gagcagagcc tacctgttgg cattgccagg acggagatga    1380
cgacctgtgg gcctcgcggc ccttgagccc gcacatgcag cgtcacgttc aagtgttcgt    1440
acctccaaac aaaaaaagtc ttgacgcttt ttttttttctt tttggttatt atgatgacgg    1500
acgattctgg tcagggcatc cacataaata tcttaaaagg tattaacgac gtaagtgcaa    1560
aaaaaaagac agtctctagc actaccacgg ttttatccat acaactcacg tacatgaatc    1620
atatcatgag atcttctagt ggaataagat ataaaactta aatatattgg gctatatgaa    1680 agagttttttt agatgtattt agtgcttaaa gaactgaaac gtagtatcta gattgtacat    1740
gtctttatga ctatatggat gagttggtgt cccgtttgat ttttcacgcg cctttgaatc    1800
catgtgaaga tcgatgtgct agctagctag ctcgctcttc atgcgttcgt ctggattttg    1860
tttgaaattc acgcagcata tatgtgtgga atataatctg tatgcacata caggtacggc    1920
ctgccgttcg tgtccccgaa caacatcctg gtgtcgacga tcaacgggac ggggtcggtg    1980
atcgaggcca tctacgtggt gatcttcctc atcttcgcgg tggaccggcg ggccaggctc    2040
agcatgctgg gcctcctggg catcgtcgcc tccatcttca ccaccgtggt gctcgtctcg    2100
ctgctggccc tccacggcaa cgcccgcaag gtcttctgcg gcctcgccgc caccatcttc    2160
tccatctgca tgtacgcctc gccgctctcc atcatggtac gtgagcgatg atgattggtt    2220
gttgctgcct tgctgggtag ctagctccag cgggtcccct tctgggcgtg tacgtgcgtc    2280
cttgctgtca acgtacggca tcagttaaca agctaagcgt gtgcttggtg tgtgcagagg    2340
ctggtgatca agacgaagag cgtggagttc atgccgttcc tgctctccct ggccgtgttc    2400
ctgtgcggca cctcctggtt catctacggc ctcctcggcc gcgacccctt cattattgta    2460
cgcacacggt tctctctcta gtctagatcc tgagccgcac tcaccgcccg gccgtacgca    2520
cgtgctatcc gcgcatgttg tccgattggc actcggaaac cactgtagca gcactgtatc    2580
actagctgtt gggactggac gtaactgcat ctgatctggc cagcacagta cccccgggct    2640
gggcgtcggt tgcccttcg atgtcccgcc caagcccaac caggcgcaca tgcctgccgc     2700
tgccgcagcc gatgcacggg catgggcgcc ggtagcgtct agcagcgtgg gcgtggccac    2760
ccacaggcag cgcacgccgg tgctagctgc cgatgggccg ccgtgcccat gtccatgcag    2820
ctggattgga cccggcacag gcagaagcaa cagcgcccgc gctctttctt gtcgcaatgc    2880
tagttagcaa actgcacggt gcactccact tcagtacaca ccaacgcgac agactgcgat    2940
gaaatatcta aggccgagtt ttttttttttt gcaaatctca tcatgtcgga atgattcatg    3000
cggtccaaac ttcagcacac ccccactgtc gctaaacccg cgctgtctgt gcatgcgtgc    3060
agatcccgaa cgggtgcggg agcttcctgg gcctgatgca gctcatcctg tacgccatct    3120
accggaaaaa caagggcccc gccgcgccgg ccggcaaggg agaggccgcc gccgcgccgg    3180
cggaggtgga ggacaccaag aaggtggccg ctgccgtgga gctggccgat gccacgacca    3240
acaaggcagc ggacgccgtc ggcggcgacg gcaaggtcgc cagccaggtg taggcgggca    3300
aggcttattt gctgtctggg actgggagga acatcctaaa cgaggctgcc ttagtttgtc    3360
```

```
ggtggagcag attggtgttg gtttctgtgg gcttttacgg ttgttgttac tctcatctcc   3420
atctctccca ggaggctacc ccaagcatgt agtagcttcc attctgattc tgggacggtg   3480
ttgcacgtta cagtgctctc aagctgtctc tgcaaagtgt gttttttttat tccatttccc   3540 tcctgctctt gttctccaac tgcgcttacc tgcccccgat ttctctaaaa aatgtattaa   3600
actatctgag aaattcatcc aactgcgagt actgtgctgt gcgtgagcaa tgc          3653
```

<210> SEQ ID NO 3
<211> LENGTH: 2911
<212> TYPE: DNA
<213> ORGANISM: Zea mays

<400> SEQUENCE: 3

```
acacacaaac acatcagcat tcagcaatag ctaatcgagc atcgtcgcct tagctcctct     60
cctctcctct ccgtcgtcgt ggaacttctc tccgccggct gtcatatata taaggagaa    120 gaagagaaca gcaactctag ctagccggcc ggcctccgtc gtcgccggcg tcgtcgacta   180
gctagctaac tctcgatctc cagttcctgc ccccgcgccc cacgcccggc cgtcgtcgtc   240
agcaatggca ggaggcttct tctccatggc tcacccggcc gtcaccctct ccggcatcgc   300
aggtacgtac gcgccaatga acaacaacg tcgtctcgag ctagatcgat ccatgcatga   360
cgccggccgg gaccggccgg atagatagge ggagatcgac ttgcataatg cttcgcgtgt   420
ttggcctttt cctggtgctt cttttttttt ttaaaaaaaa tcttatggga ccttgatgac   480
atgcttttca tgtggttttc attcattctg ttgccgtact acgttcttct agattttgtt   540
tattccgaca tgacgactgt cttgtccatc cttgtatcat cgatccgtcc tttgcatgca   600
tgcatccacc agtcgtcagc cttccttttt gccgtttgtg ccattgcact gtagagcacg   660
cacgcactct ctagctgtag agaggcgcgg cagtaggcat gcatgcagca gctagtcaca   720
ctggacaacc aactgtcttg tccatcatct atcaacaata cttgcatatc agaatacgta   780
gtatgtagct ttagcatttt ttttttcttca cctatactac tgctagctgc atcttcttga   840
actttctctg atgctccccg cggcccattg agacgacgat gcactctttc tccaattcgt   900
tagctgcgat catggcacag gccttttaatt tgttgctagc tagaacacac atgcatgcat   960
cgccgaggta tagcaacttt tccactcaag aataatggta ataagcagtg cagatcagat  1020
ccacatattg ggcattagat cacgaaatac agttgcaaat agctgctcac aacgtaacgc  1080
actatctaag aatcatttct atatacgtgt attttttgct ggaatggtta tgatcgatcg  1140
gttgggcatg cagcagggaa ggcgtgtgcg tgtgcatgca gctacctagc tttttgccat  1200
atcagcgttt ccttaaccta atcaccacgc ttctctctgt tagtggacgc acacgcattg  1260
tacatatata tgtgtatagt attgtactcc taccactttt actgaaaatg acgacactga  1320
cgcgtagtta ccctcttctc tcttgtttct tcgatttgga ttgtgcagga acatcatct   1380 ccttcctggt gttccttgca ccagtgtaag tagctagcta tagccacctt tcttcgttcc   1440
cttactgtct caatttcaga ccgactcgga ttcatgcgtg aatcgatgga tgatccaaga  1500
ctgacatggc atgcctcttg tacgcaccgt accaaaaaca gggcgacgtt cctgcaggtg   1560
taccggaaga agtcgacggg cgggttcagc tcggtgccgt acgtggtggc gctcttcagc   1620
tcggtgctgt ggatcttcta cgcgctggtg aagaccaact cgaggccgct gctgaccatc   1680
aacgccttcg gctgcggcgt ggaggcggcc tacatagtcc tctacctggc gtacgcgccg   1740
cggcgggcgc gcctgcggac tctggcctac ttcttcctgc tggacgtggc ggccttcgcg   1800
ctcgtcgtcg ccgtcacgct cttcgccgtc cgcgagcccc accgcgtcaa gttcctcggc   1860
```

```
agcgtctgcc tcgccttctc catggccgtc ttcgtcgcgc cgctcagcat catcgtcaag   1920
gtggtcaaga ccaagagcgt cgagttcctg cccatcagcc tctccttctg cctcacgctc   1980
agcgccgtcg cctggttctg ctacggcctc ttcaccaagg accccttgt catggtaacg   2040
actgatcaat aatgtaatat atggttaact gatccatata tatatataaa atggtaactg   2100
aataatgctg gggatgtttc tcgattatat atatctattc agtaccccaa cgtcggcggc   2160
ttcttcttca gctgcgtcca gatgggcctc tacttctggt accgcaagcc ccgcccggcg   2220
gccaagaaca acgccgtgct gccgacgacc acggacggcg ccaacgcggt gcaggtgcag   2280
gggcaggtca tcgagctggc gcccaacacg gtggccatcc tgtcggtgag ccccatcccc   2340
atcgtgggcg tgcacaagat cgaggtggtg agcagcagc acaaggaggc cgccgtggcc   2400
gccgagaccc gccggatggc cgccgcaaac ccggacggcg ccatgccgga ggtcatcgag   2460
atcgtccccg ccgccgccgc ggtgtgaccc aacgccaatc accatgcacc gtacacaccc   2520
tgctagcttc ttattagcta gctcggatga cgtacgacag tttggtggca agtggctggc   2580
agctcaagca tgcagatgca ggcatcgtcg tctgctagtt gatcgtttag ttggttaatt   2640
gttggattat tattgcgtgt ctctctcgtg tgcgtagtct tgtcagttca gttcagttca   2700
gtgtcgaatc aagtagtagt agctgttgtt tgcattggat ctgacaatgc atgctaataa   2760
ttatggtggt gtgatggtct tggtcggtac gtgcgtagtc gtctacgtac gccgtgtcaa   2820
cgtcgtagat ctctacggga agatgataag actgtaacat gcagggcatg catctattta   2880
tacttaacat attctttgtg tgcttaatt t                                   2911
```

<210> SEQ ID NO 4
<211> LENGTH: 5438
<212> TYPE: DNA
<213> ORGANISM: Zea mays

<400> SEQUENCE: 4

```
ctgagctgac tgtggatctc atccgtatcg tatatacgtc gtcctgtttg gatccaccgc     60
gttttgctaa ttcccttcga accggccggt ggccttcgtt ctcccaccag gcctgtctgt   120
ctgctgtatc cgccagagct tccatggatt ccaccctctt catcatcggc gtcataggta   180
agcttgtgta tcattctgaa ctgctttgtt attattatta gtcttcattc gtccagcttt   240
ccttatcttc ttcttctaca ttgaaatagg caacatcatc tcagttctcg tcttcatatc   300
gcctatgtaa gtgtctttct ccatatatat ggtttccctg tcgtcgctgt tgctagctag   360
cttctttct gaacaccacc acgggcacca atccatgcat ggatacagca agacgttctg   420
gaggatcgtg cggggcggga cgacggagga gttcgagccg gcgccgtacg tgttgacgct   480
gctcaacgcg ctgctgtggc tctactacgg cctcaccaag cctgacggct tcctcgtcgc   540
caccgtcaat ggctttgggg ctgtcatgga ggccatctac gtcgtcctct tcatcgtcta   600
cgccgccaac catgccacaa gggtgagggg tcggagcagc tggggccagt atatatagtt   660
cactcacaca atccgttgct taattctgca taattctttc ttcaagcact tgagtcttag   720
gaattacgga gtatatagtt aaagaaaagc acaaccacca ttcgtttatt aaagaaaagc   780
atgtgttgcc ttatattata gtttgttcct ttatcgcaat tatgattatg caggttaaga   840
ccgcgaagct ggcagcagcg ttggacatcg gtggcttcgg agtcgtgttt gcggccacca   900
cattcgccat cagtgaattt gaattgagaa ttatggtgat aggaatgata tgtgcctgcc   960
tcaatgtgct catgtacggg tcacccttg cttctatggt aagttttttt tcctcacatg   1020
```

```
catatttata cactattcct cttttctttc cttttttggt tattttagaa acttaaatcc    1080
cctctggtat taattcccga gaatttcact taattcccaa gaatcccaaa aaaaattaag    1140
tttctaaact agcccttagt gagacttaat ttatttgttc gccgtaagtc gattttgaga    1200
tgcacatttc tccttaattt tccttttata gctgaccgtg cacggccttg aaacatcacg    1260 atctttcag ttaaatttaa ttagcacggg ctaaatttt acattgcaaa agaaaataaa    1320
ctaatttcac acacacatat atagtatata gctagcaaac tgctaatggg ccagcaaaac    1380
ttatggatga taacattgag caatgaaatt attgtcatgt aacggtaact atattataat    1440
agtgagtttc gatccatgat ctaatatata ccatataata atattgatgc cacttggccc    1500
cacagacaaa gtagagtata gttcaagttt ggagatatat aaatgataat aataataata    1560
aagctgctca agatattttc attctggcga tccatgtctg tccacgatgg atcgacgata    1620
aaatactcgg tgtttattat aatggacagg gcgctttgtg gggcgattat tttatgttgt    1680
gttgtccctt tcatgattat ttattaaata taaggacaga agtccaagca aaacacatgt    1740
gccccaagca atagggatat atagtgacat attgtgaaaa tagttatata ttttggggga    1800
gaatcatgtg tcagggatat tgtacaatag aaaaacattt cttagtatgt aggtcctcaa    1860
ctgcccctgt tttttctctt attttagca gatgttcgat ccacttccac aattccactt    1920
gcaggaataa tataataaat atagatatat atggtacata agctgtatgt aaaatccata    1980
taataatatt aatattacat tatataccct aacgaatcat ttctaaagct tttattaggt    2040 ataataaaa gtaaatttat attttggtgc ttgtagctag gtgtggccgt gtggggcacg    2100
tgcaagcaac cttactcgtt ccacctccta tcttttgctc cactttgtaa ataatacata    2160
ttacagcgta aaactgtgta gaaagtatga ttttacggct atatacacgg tgtgctacga    2220
ctaaaagtta gggacgacct cacgccgata attggatgac agatttttt cctttgatat    2280 ctttcttctc tggcatgcca aatcgaattc ctccctctgc ctttaatttc tatttgttag    2340
gattatatga aactatttcc acaagtatag ttagagactc aaattcagat actagaaatt    2400
aatgatggtt tacaagccat aaataaataa attaaaaata aacatattta gattttaatt    2460
tgaatgaaaa gagaacattg cttcggtttg atgcagatta acttatacag aaatcatata    2520
ttatgtcatg agagacaagc aaagattggt caacttatta ccatttcttg caaaatcaag    2580
tttgccgtat tattattttg tcctttcttt ttttaaaaga ttattagctg gttattggtt    2640
ctctgggcag ttaacggggt agagtattcc acagaattaa ataatcacca tgcaaggaac    2700
acgcgttgtc ctctacatac gattctttat ttacttaatt ctacatcaca cattttgtgc    2760
aagaacagta gctattagaa aaaaaatgtg agcatcggtt cacaaccggc tatagtactg    2820
gattatcaac tgatattaga caatcgaaat taaagacctt attttgaag gaccggtgaa    2880 atgaccagaa ggggtgaatt agagccaatc aaatttatt gttaaaaact taaatttaga    2940
ccttatttgt gaaggaccag aagaggtgaa tgagagccaa tcaaatttta ttacaaaaaa    3000
ctaaaattta gcacttaact tcaattgaga tgaagaaatc gttcaaacca gaagcacatc    3060
ggccaaatag taatcttacg atttcaaaat ggtaccccta gatacatttg gttttttgtt    3120
tagaataccg gtattctttg gctaagttca tttggttat tggttttgt ttagaatatg    3180 ggtattctaa acaaaaacca aatgaatttt gccaaaagag atggatgtca ataaaagccc    3240
acatatctat ttatagaggt gatggataca tcatatccac ttagccgggg caaaatggat    3300
caactcctag gattttgatc agacgaccac gcgctctaca caaagttgct tcgcctcgac    3360 acacccttg tgatgatgtc atgtgccacc tctgattcct gccgaaaccg ccaccgtcaa    3420
```

| | |
|---|---|
| gttttgaggc ccaaactcag caaaaccagc agatgggtgg ttttgaggct caaccacaaa | 3480 |
| accaccgcga gtagtgcatc gcatgcgcgt ccccacgtcc tggacacatg tcccattagt | 3540 |
| ccttgaccgc atcggcgaca gtgcgacaca agccactctg tcatgtcctc gcgctagtgc | 3600 |
| gtgtcctagg tgtgagccac cacaacttgt caaccggctc ctccgacccc ttggtcaagt | 3660 |
| cctagtgctc gtctttcatc actctccgtc tatcggcata aaccctcgtg tgaccttcac | 3720 |
| attcgccatt gaacaacata catgtacttc acacctgcac accataagcc gagagacatg | 3780 |
| gttgcacaat acataactca tactctggtc agtccaccga ctacatcaaa atactatccg | 3840 |
| ttgacaatca cttatcatca actcgaacca caagggacaa atcaacttgt gttcacaatt | 3900 |
| gtttgccata gagagaaaga aagcgtactc cgtgtgttgc ttgggtttac cgagaagcac | 3960 |
| gtgtgtaaaa tgggtagcat actctagtag tactacgagt gcacgacgtg actcctacag | 4020 |
| attccaaact cttggcaaaa ttaatatcgc gacatgtcat catgtccatg ccattacctt | 4080 |
| agctgtattg acaggccgga cctgctattt gtgtcggccg tacgtgttct tgcggtcctc | 4140 |
| gtcgggtggg gtttcgctct ctgaattttc tgattggttc catcgatatt ttctgattgg | 4200 |
| ttccatcgaa agcgaaacca ggaccgtacg tggcgccaaa ttcaaccaga ccacccatcc | 4260 |
| cttcccgggg tcatgtcaca tccctgttgc ttcacgtttt cttacaaaat tacccgctcc | 4320 |
| gtccgtgaag caaatataac tatgatatcc ctatctgtca gagtagttta aatttaacta | 4380 |
| aatttataat aaacaatact cgctttggtc ctaaatctag acacatatat atatatatat | 4440 |
| atatatataa cacatacatc aagtattgta taaattcaca aaataccact atatgaacgc | 4500 |
| ccttaaattt taaattaaaa aattatctaa gaaaacataa gcaataatta acccatgcca | 4560 |
| atgcaagttg aatacttgaa ttgaaaaaag ttgattccag ctcagggaac ctataaccat | 4620 |
| ggcttcgcat gagttggcga ttgcctgaac aggcccatgc agagcaacta accatagaat | 4680 |
| agaacaatac gcgatgaaat tcaccgtacc ctgcaacgta atggatgtgt gattagtatc | 4740 |
| accggcacct catttttacc cgtcatctcg ttgtacctac attttcagaa aacggtgatc | 4800 |
| acgacaaaga gcgtggagtt catgccattc ttcctgtcct tcttcctctt cctcaacgga | 4860 |
| ggcgtctggg caacgtacgc ggtgcttgac cgcgacatct tcctcggggt aatgtttaaa | 4920 |
| gcctctctgt tcttctcgat cttcttcccc aacctctgtc ttttccgcta cccatactaa | 4980 |
| acagaacctc tcgatcgctc tctgcatgca gatccccaat gggataggct tcgtgcttgg | 5040 |
| caccatccag ctgatcgtct acgcgatcta catgaacagc aaggcctccc aatgcagcaa | 5100 |
| agaaacagcg tcctcgcctc ttctggcctc cgaccgggga gaagcatcta gccatgtctg | 5160 |
| atgatgagct tcgatcagtg cgcgcgctgg agtatagcat agaagtctct tgctgtcaaa | 5220 |
| aacttccaag accaacggta cctaccagca tgcatgcatg caagaggtta ccaattttta | 5280 |
| ttgtttgaaa attcatgtaa acttgtgacc tccatggatt gtttctttct ttggtataag | 5340 |
| cttcgaagat gttagattgt tagcacggta gttttgccag agaagggtgt tgtcaatata | 5400 |
| atgaagaaat ggtgaaaatc catacatttg attatcga | 5438 |

<210> SEQ ID NO 5
<211> LENGTH: 3189
<212> TYPE: DNA
<213> ORGANISM: Zea mays

<400> SEQUENCE: 5

| | |
|---|---|
| ctcaggagct aatgactcac ctctccgtgc tcacctcctc ttcttgaggc ttgagctctc | 60 |

```
tcttcctctc tcccctcagc tcatctccac cgtctccta tatataggat gctctgccgg    120
ctccaaggtt cccaagcgcc caaggcagcg gagagagcta gctccctcct cctcctcagg    180
tagcgagcga gcgagctcct ctgcccctct gcacacctgg cctcccctcc tccgctgcag    240
gaccgccgtt gacgactgct ccaccagtac tgcgcgcgcc cgcgctgcct acccttacct    300
agccagagcg cggcgcgcga gagggagaac gaccaggagg ggaggagatc gatcgatcga    360
tcgatcgaga tagatggctt tcctcaacat ggagcagcag acctgggcct tcaccttcgg    420
tatcctaggt acatatatac tgtcagtctg tcactcgtag ctactaatta accgcatcaa    480
cggagccgcc ctgccgtctt cgtcctcgtc agtgtttctg cattgttttc cttccttgtc    540
ccaagtcctt tgagacgcac gcatacatga tacatgcatg gcatcatcgt ctcccaagtc    600
ctaggtacag tttcatcacc gcgcgcctct ctcagatatg tgtcgtcgta caggacaaca    660
caacacgtcc tcgtcaatct actagctata tgcgctaata accacctctt cctttccgag    720
ccacggcaca gtatagcctg ccatccgaac gaacggaacc gcccaaaacc caactttttt    780
tgggcctaac taatgcggtg gttagcccaa acaaagaaac cagggcagtc atacatttta    840
catgtagtac ctgcttgacg acgggaacca acacaacggc gcgccgcgag gagagtttgt    900
tccatttcct ccgcctgcag gctagctgca gctaataacc ccggccgccg gatgttctcc    960
ttctcgcatg cttttttttt gggggttct ttctccgcct cctgctcttc gtctgttcta   1020
ccatcgtcga tcacacagca atttgactga ccgcgtctgt ccttccgacc ttgccgtttt   1080
gctttgcagg taacataatc tcgctgatgg tgttcctttc gccgctgtaa gtaactctct   1140
gctttaattt atttaaccta gccgtgaact tttcatattt acgttacag tatccagtac    1200
catgcataat atactaccaa tatgtttcta tgtatattca gtaaagggaa gcgtccaaaa   1260
tatatactgc catcaggtat gatgagaaca tatatataaa gaacatggca cgcacgcatg   1320
cgtatctcac tgttgaatga atgacgtgcc atcatcgtcc atgctcttct agatcctttt   1380
cctttaattt atgcgtggtt ctagatcccc ctatatatat atatatatat atatatatat   1440
atatatatat acgtacacct gaagacaaca tagctagcta ggaaataaac tcgttgggaa   1500
ttgaattgtc gcattaataa cgtcacttta atcagttgcg agccagtacg tgtcactgtt   1560
cggtggttgc gttgcacatg cttttagtat ggaacagcgc acgcaatcta gtaataatta   1620
atctaaaaaa tcacacggta aaaatattc gttcccgctg atcccgcgca ggccgacgtt   1680
ctaccgcgtg taccgcaaga agtcgacgga ggggttccag tcgaccccgt acgtggtgac   1740
gctgttcagc tgcatgctgt ggatcttcta cgcgctgctc aagtccggcg ccagagctgct  1800
ggtgaccatc aacggcgtcg ggtgcgtgat cgaggcggcg tacctggccg cgtacctggt   1860
gtacgcgccc aaggccgcca gggcgctgac ggccaagatg ctgctggggc tcaacgtcgg   1920
cgtctttgga ctcgccgcgc tcgccaccat ggtggtctcc agcgccggcc tccgcgtgcg   1980
cgtgctcggc tggatctgcg tcagcgtcgc gctcagcgta ttcgccgcgc cgctcagcat   2040
catggcacgt atctaatta atctctctct ctctctctct ctctctctct               2100
ctctgaagag ggatgtgaat tgttggaacc gccattaatt cgctgactgc cctatctaca   2160
tctactttcc tgcagcggca ggtggtccgg accaagagcg tggagttcat gcccatctcg   2220
ctctccttct tcctggtgct gagcgccgtg atctggttcg cgtacggcgc gctgaagagg   2280
gacgtgttcg tggcgttccc caacgtgctg ggcttcgtct tcggcgtcgc gcagatagcg   2340
ctgtacatgc gtacaggaa caaggagccc cggcggtga cggtgaggag ggcgaagctg   2400
ccggagcacg ccaaggaggt ggtggtggcc gcggcggcg ccgaggccag ggcgagctgc   2460
```

| | |
|---|---|
| ggtgctgagg tgcaccccat cgacatcgac atcgaagcta cgccgacgcc ggtggaggag | 2520 |
| gtgcacgagc cgcaggtggt cgtggtcgtc gacgtggacg tggagcctgt cacctgcgcc | 2580 |
| ggcgccgccg aggcagctgc gggagcaggg gcagatgcgt ccggcgtggc cgacggcggc | 2640 |
| gtccctggac ccatggcgcc gccggagcag ctggcgatca agcccgacat ggccatttcc | 2700 |
| gtggaggcgt aggttggtta aagtgtaata gcagagtgag tcgatatcga tcagtagtag | 2760 |
| atttgtcgag tcaaggaagg ggcctgctgc tgctgctacg cgacagcagc ggccagatgt | 2820 |
| actgcctgca tgcatgcagt ccctcccgtt gactcgaccc gtagagaagg gatgggatgg | 2880 |
| aagtagccgg gtccttgggc gagtagcggc gccttggcac ccacgggcca gccgtactgg | 2940 |
| cctgtgtgat gaaccggcga gagagatgag ataatgtgcg agcgagagag ggttggttgg | 3000 |
| gttgtggtag ttgaagaaga cggctagcta gctgctgctg ctgggctctc tatctgtctc | 3060 |
| tagatctgtg tatgtctgtg taatcgagga ttccctcacc ttgcatgccg cctccctttt | 3120 |
| gtgtccttct agtctgatga ttgttttcat tccatccatg ccggcgtcgc agtaataaaa | 3180 |
| tttttttgg | 3189 |

<210> SEQ ID NO 6
<211> LENGTH: 801
<212> TYPE: DNA
<213> ORGANISM: Zea mays

<400> SEQUENCE: 6

| | |
|---|---|
| wttaytkrtm arcyamrtac kwtctmtgta cgyaygcagc ttccaaacat cctkgggttc | 60 |
| accttcggcg tggtccagat ggtgctctac gtgttgtaca tgaacaagac gccggtggcg | 120 |
| gcgactgccr agggyaagga tgccggcaag cttcctcag ctgcagacga gcacgtcctc | 180 |
| gtcaacatcr ccaagctcag cccagccctc ccggagagga gctccggggt gyacccagtc | 240 |
| acccagatgg cgggmgttcc ygtyaggagc tgcgctgctg aagcaaccgc gccggckatg | 300 |
| ctgcccaaca gggacgtggt cgacgtcttc gtcascgac acagccccgc cgtccacgtg | 360 |
| gcatagattc tcgatcgatc gsgtgcatgg cccatgcatg ygcccgcyac acgtacgcta | 420 |
| gmttttatat attcgaagga ckacttgctg ctggtcgtga gcatatatat gatggasraa | 480 |
| atrattaagt agtatatatr taagtaattr actrccatgs atggaagcta gstaatggat | 540 |
| ggaggcagag gycagarcga tgaagggga agctatacat atatrtgygt aattaatata | 600 |
| gatatatggg mtttgtgtwc wtmtttgcwg ctatgtatta atttgcatgg rtatctgtta | 660 |
| ttccttttta tgtgtaacgt cttctaataa aatgtaattg aaccsacact acyrttgtta | 720 |
| gctaccacaa gtttcscraa aatggcttct rtgtgttcgg gcsggaaagc cctgrcccaa | 780 |
| agttgtcatc cggttcaryc a | 801 |

<210> SEQ ID NO 7
<211> LENGTH: 801
<212> TYPE: DNA
<213> ORGANISM: Zea mays

<400> SEQUENCE: 7

| | |
|---|---|
| gatggtgctc tacgtgttgt acatgaacaa gacgccggtg gcggcgactg ccragggyaa | 60 |
| ggatgccggc aagctttcct cagctgcaga cgagcacgtc tcgtcaaca tcrccaagct | 120 |
| cagcccagcc ctcccggaga ggagctccgg ggtgyaccca gtcacccaga tggcgggmgt | 180 |
| tccygtyagg agctgcgctg ctgaagcaac cgcgccggck atgctgccca acagggacgt | 240 |

| | |
|---|---:|
| ggtcgacgtc ttcgtcascc gacacagccc cgccgtccac gtggcataga ttctcgatcg | 300 |
| atcgsgtgca tggcccatgc atgygcccgc yacacgtacg ctagmtttta tatattcgaa | 360 |
| ggackacttg ctgctggtcg tgagcatata tatgatggas raaatratta agtagtatat | 420 |
| atrtaagtaa ttractrcca tgsatggaag ctagstaatg gatggaggca gaggycagar | 480 |
| cgatgaaggg ggaagctata catatatrtg ygtaattaat atagatatat gggmtttgtg | 540 |
| twcwtmtttg cwgctatgta ttaatttgca tggrtatctg ttattccttt ttatgtgtaa | 600 |
| cgtcttctaa taaaatgtaa ttgaaccsac actacyrttg ttagctacca caagtttcsc | 660 |
| raaaatggct tctrtgtgtt cgggcsggaa agccctgrcc caaagttgtc atccggttca | 720 |
| rycacactag rtcccrgacr tytataaaag gagcctcaaa ttgctaagyt tcagttttg | 780 |
| actcccacc cctataaatg a | 801 |

<210> SEQ ID NO 8
<211> LENGTH: 801
<212> TYPE: DNA
<213> ORGANISM: Zea mays

<400> SEQUENCE: 8

| | |
|---|---:|
| tctgcgtcgg mttctcygtc agtgtcttcg tsgcgccact magcatcatg gtgagcyctg | 60 |
| agcacgcgta taaaactgtg ccaagatgca tggacgacag atygatcarc ccwrtcagtt | 120 |
| ttgatccatg tgtatcrttt ctaatgmrcc gtrtwtatat atgtgtgcag agacgmgtga | 180 |
| tccagacgaa gagcgtggag tacatgccct tctccctctc cctctcgctc accctcagcg | 240 |
| ccgtcgtctg gttcctctac ggcctcctca tcaaggacaa atacgtcgcg gtaattgttt | 300 |
| catctaatct gctgcarccg ycatggtatt ggtatctctc actkkycwtt aytkrtmarc | 360 |
| yamrtackwt ctmtgtacgy aygcagcttc caaacatcct kgggttcacc ttcggcgtgg | 420 |
| tccagatggt gctctacgtg ttgtacatga acaagacgcc ggtggcggcg actgccragg | 480 |
| gyaaggatgc cggcaagctt tcctcagctg cagacgagca cgtcctcgtc aacatcrcca | 540 |
| agctcagccc agccctcccg gagaggagct ccggggtgya cccagtcacc cagatggcgg | 600 |
| gmgttccygt yaggagctgc gctgctgaag caaccgcgcc ggcktatgctg cccaacaggg | 660 |
| acgtggtcga cgtcttcgtc asccgacaca gccccgccgt ccacgtggca tagattctcg | 720 |
| atcgatcgsg tgcatggccc atgcatgygc ccgcyacacg tacgctagmt tttatatatt | 780 |
| cgaaggacka cttgctgctg g | 801 |

<210> SEQ ID NO 9
<211> LENGTH: 801
<212> TYPE: DNA
<213> ORGANISM: Zea mays

<400> SEQUENCE: 9

| | |
|---|---:|
| cgggmgttcc ygtyaggagc tgcgctgctg aagcaaccgc gccggckatg ctgcccaaca | 60 |
| gggacgtggt cgacgtcttc gtcasccgac acagccccgc cgtccacgtg gcatagattc | 120 |
| tcgatcgatc gsgtgcatgg cccatgcatg ygcccgcyac acgtacgcta gmttttatat | 180 |
| attcgaagga ckacttgctg ctggtcgtga gcatatatat gatggasraa atrattaagt | 240 |
| agtatatatr taagtaattr actrccatgs atggaagcta gstaatggat ggaggcagag | 300 |
| gycagarcga tgaagggga agctatacat atatrtgygt aattaatata gatatatggg | 360 |
| mtttgtgtwc wtmtttgcwg ctatgtatta atttgcatgg rtatctgtta ttccttttta | 420 |
| tgtgtaacgt cttctaataa aatgtaattg aaccsacact acyrttgtta gctaccacaa | 480 |

```
gtttcscraa aatggcttct rtgtgttcgg gcsggaaagc cctgrcccaa agttgtcatc        540
cggttcaryc acactagrtc ccrgacrtyt ataaaaggag cctcaaattg ctaagyttca        600
gtttttgact ccccacccct ataaatgagy gacarcgycc acccaracgc gagtgtggca        660
gcggttaccm gagagcgcga ggcgacgrca gttccccgag agcgaaaggc gacgrcgscc        720
agagactcgc gcgacygcga wgccaagcgc ggyggcggcc tcyagaggca ccayggcgg         780 ctactcccag atyyggcggc g                                                  801

<210> SEQ ID NO 10
<211> LENGTH: 501
<212> TYPE: DNA
<213> ORGANISM: Zea mays

<400> SEQUENCE: 10
tttcctcagc tgcagacgag cacgtcctcg tcaacatcgc caagctcagc ccagccctcc         60
cggagaggag ctccggggtg cacccagtca cccagatggg gggcgttcct gtcaggagct        120
gcgctgctga agcaaccgcg ccggcgatgc tgcccaacag ggacgtggtc gacgtcttcg        180
tcagccgaca cagccccgcc gtccacgtgg catagattct cgatcgatcg cgtgcatggc        240
ccatgcatgc gcccgccaca cgtacgctag cttttatata ttcgaaggac gacttgctgc        300
tggtcgtgag catatatatg atggagaaaa tgattaagta gtatatatat aagtaattaa        360
ctgccatgca tggaagctag ctaatggatg gaggcagagg ccagaacgat gaaggggggaa       420 gctatacata tatgtgtgta attaatatag atatatgggc tttgtgttca tctttgcagc        480
tatgtattaa tttgcatgga t                                                  501

<210> SEQ ID NO 11
<211> LENGTH: 801
<212> TYPE: DNA
<213> ORGANISM: Zea mays

<400> SEQUENCE: 11
tcgtctggtt cctctacggc ctcctcatca aggacaaata cgtcgcggta attgtttcat         60
ctaatctgct gcarccgyca tggtattggt atctctcact kkycwttayt krtmarccyam      120 rtackwtctm tgtacgyayg cagcttccaa acatcctkgg gttcaccttc ggcgtggtcc        180
agatggtgct ctacgtgttg tacatgaaca agacgccggt ggcggcgact gccragggya        240
aggatgccgg caagcttccc tcagctgcag acgagcacgt cctcgtcaac atcrccaagc        300
tcagcccagc cctcccggag aggagctccg ggtgyaccc agtcacccag atggcgggmg         360
ttccygtyag gagctgcgct gctgaagcaa ccgcgccggc katgctgccc aacagggacg        420
tggtcgacgt cttcgtcasc cgacacagcc ccgccgtcca cgtggcatag attctcgatc        480
gatcgsgtgc atggcccatg catgygcccg cyacacgtac gctagmtttt atatattcga        540
aggackactt gctgctggtc gtgagcatat atatgatgga sraaatratt aagtagtata        600
tatrtaagta attractrcc atgsatggaa gctagstaat ggatggaggc agaggycaga        660
rcgatgaagg gggaagctat acatatatrt gygtaattaa tatagatata tgggmtttgt        720
gtwcwtmttt gcwgctatgt attaatttgc atggrtatct gttattcctt tttatgtgta        780
acgtcttcta ataaaatgta a                                                  801

<210> SEQ ID NO 12
<211> LENGTH: 801
<212> TYPE: DNA
```

<213> ORGANISM: Zea mays

<400> SEQUENCE: 12

| | | | | | |
|---|---|---|---|---|---|
| gacgckggca | gtgaggaaya | gaaggattca | ggtrsgtgga | atcaaaaact | tacacaggcg | 60 |
| acaggaagag | gaaagagcgca | atgacattcc | ctggggagac | agatcyaaca | gagattaggc | 120 |
| gaggcaagaa | gaagaccatc | aggtaggcat | gmarcagagg | caggaatggc | atggtgayac | 180 |
| tgaccagaaa | ctccgaagaa | gaacctggcg | ataygctcca | tctcttccgc | ttcgygctta | 240 |
| tcgctgtgcg | gaaccctcgg | ctgtgctgsc | ctggaacccg | aacggagcag | rgggggtagt | 300 |
| gastggactg | gastccttc | ctccacggtc | taggccsgga | gcgcacccac | acccaacgag | 360 |
| cagttagcta | gtagctctca | agtctgaayr | gctgagcsca | rcacacagca | gccaagccaa | 420 |
| cgagcctgtg | tacgggcggt | gtctttgtgc | ctgtgtgtca | cccggtgcag | cagggaacga | 480 |
| gcggtgtggc | taatatataa | ggagcagagg | attgtgatct | tgggaggtaa | ggggtaggac | 540 |
| cggtggagaa | gagrrcctgt | tcgracggaa | gcccatacgt | tcttatcttc | ttcttagctt | 600 |
| gtyagtcaaa | gtrtagatgg | ccatttggca | ctaacacgat | gggccggccc | aggcayggca | 660 |
| cgaaaaagca | cggtccaggc | acgacccggt | ccggttagta | tagtgccagt | gcctggcacg | 720 |
| gcacggctat | agtgccgtgc | ctgggccact | atctcgaccc | gtagtgctgg | cacgggcacg | 780 |
| acacagttac | atttttatt | t | | | | 801 |

<210> SEQ ID NO 13
<211> LENGTH: 801
<212> TYPE: DNA
<213> ORGANISM: Zea mays

<400> SEQUENCE: 13

| | | | | | |
|---|---|---|---|---|---|
| gttcctccca | gtcccagaca | gcaaataagc | cttgcccgcc | tacacctggc | tggcgacctt | 60 |
| gccgtcgccg | ccgacggcgt | ccgcygcstt | gttggtcgtg | gcrtcggcca | gctccacggc | 120 |
| agcggccacc | ttcttggtgt | cctccacctc | cgcggcggcg | gcggcggcct | ctcccttgcc | 180 |
| ggccggcgcg | gcggggccct | tgttttccg | gtagatggcg | tacaggatga | gctgcatcar | 240 |
| rcccaggaag | ctcccgcacc | cgttcggkat | ctrcamgcat | gcacagacag | cgcgggttta | 300 |
| gmgacastgg | ggstgtrcyg | aagtttgsac | sgcatgaatc | attccgacat | gatgagattt | 360 |
| gsaraaaaaa | aaarctcggc | ctwagatatt | tcatcgcagt | ytgtcgcgtt | ggtgtgtact | 420 |
| gaagtggagt | gcaccgtgca | gtttgctary | tagcattgcg | acaagaaaga | gcgcgggcgc | 480 |
| tgttgctyct | gcctgtgccg | ggtccaatcc | agctgcatgg | acatgggcac | ggcggcccat | 540 |
| cggcagctag | caccggcgtg | cgctgcctgt | gggtggccac | gcccacgctg | ctagacgcta | 600 |
| ccggcgccca | tgcccgtgca | tcggcwgcgg | cagcggcagg | catgtgcgcc | tggttgggyt | 660 |
| tgggcgggac | atcgaaaggg | caaccgacgc | ccagmccggg | ggtactgtgc | tggccagaty | 720 |
| agatgcagtt | acgtccagtc | ccaacagcta | gtgayacagt | rctgctrcag | tggtttccga | 780 |
| gtgccaawcg | gacaacmtgc | g | | | | 801 |

<210> SEQ ID NO 14
<211> LENGTH: 501
<212> TYPE: DNA
<213> ORGANISM: Zea mays

<400> SEQUENCE: 14

| | | | | | |
|---|---|---|---|---|---|
| cttggggtag | cctcctggga | gagatggaga | tgagagtaac | aacaaccgta | aaagcccaca | 60 |
| gaaaccaaca | ccaatctgct | ccaccgacaa | actaaggcag | cctcgtttag | gatgttcctc | 120 |

```
ccagtcccag acagcaaata agccttgccc gcctacacct ggctggcgac cttgccgtcg    180
ccgccgacgg cgtccgctgc cttgttggtc gtggcatcgg ccagctccac ggcagcggcc    240
accttcttgg tgtcctccac ctccgcggcg gcggcggcgg cctctccctt gccggccggc    300
gcggcggggc ccttgttttt ccggtagatg gcgtacagga tgagctgcat caggcccagg    360
aagctcccgc acccgttcgg gatctgcacg catgcacaga cagcgcgggt ttagcgacag    420
tgggggtgtg ctgaagtttg gaccgcatga atcattccga catgatgaga tttgcaaaaa    480
aaaaaaactc ggccttagat a                                              501

<210> SEQ ID NO 15
<211> LENGTH: 501
<212> TYPE: DNA
<213> ORGANISM: Zea mays

<400> SEQUENCE: 15
cctcctggga gagatggaga tgagagtaac aacaaccgta aaagcccaca gaaaccaaca     60
ccaatctgct ccaccgacaa actaaggcag cctcgtttag gatgttcctc ccagtcccag    120
acagcaaata agccttgccc gcctacacct ggctggcgac cttgccgtcg ccgccgacgg    180
cgtccgctgc cttgttggtc gtggcatcgg ccagctccac ggcagcggcc accttcttgg    240
tgtcctccac ctccgcggcg gcggcggcgg cctctccctt gccggccggc gcggcggggc    300
ccttgttttt ccggtagatg gcgtacagga tgagctgcat caggcccagg aagctcccgc    360
acccgttcgg gatctgcacg catgcacaga cagcgcgggt ttagcgacag tgggggtgtg    420
ctgaagtttg gaccgcatga atcattccga catgatgaga tttgcaaaaa aaaaaaactc    480
ggccttagat atttcatcgc a                                              501

<210> SEQ ID NO 16
<211> LENGTH: 501
<212> TYPE: DNA
<213> ORGANISM: Zea mays

<400> SEQUENCE: 16
ccgtaaaagc ccacagaaac caacaccaat ctgctccacc gacaaactaa ggcagcctcg     60
tttaggatgt tcctcccagt cccagacagc aaataagcct tgcccgccta cacctggctg    120
gcgaccttgc cgtcgccgcc gacggcgtcc gctgccttgt tggtcgtggc atcggccagc    180
tccacggcag cggccacctt cttggtgtcc tccacctccg cggcggcggc ggcggcctct    240
cccttgccgg ccggcgcggc ggggcccttg ttttccggt agatggcgta caggatgagc    300
tgcatcaggc ccaggaagct cccgcacccg ttcgggatct gcacgcatgc acagacagcg    360
cgggtttagc gacagtgggg gtgtgctgaa gtttggaccg catgaatcat tccgacatga    420
tgagatttgc aaaaaaaaaa aactcggcct tagatatttc atcgcagtct gtcgcgttgg    480
tgtgtactga agtggagtgc a                                              501

<210> SEQ ID NO 17
<211> LENGTH: 801
<212> TYPE: DNA
<213> ORGANISM: Zea mays

<400> SEQUENCE: 17
atgcaacatt agtttcttga gcagcaatga gagcataatg agctatacta tcaatgtcac     60
gayatcsatg tggcaaaaac aatattactt ctargtctrt cttgagcaat agagtgatta    120
```

| | |
|---|---|
| ttgctwacag gaggtayaka agcttaawst gygtgaagat gaaaatcytr tagttgtyaa | 180 |
| agtcattatc tamtwtcaag ttsaagyatt rtcttgactt rgtargtgtt ygtggagctt | 240 |
| agcaccctag trgtgtttgg sgaggaaaca atttttataga ttaaatcaac attagtttct | 300 |
| tgattagtgt aaatatgctt attattatyt tttycttata kttatttgga cygactawak | 360 |
| ctagaactgc actcttttga tttgggyatt caagacrggc waaattaagc acacaaagaa | 420 |
| tatgttaagt ataaatagat gcatgccctg catgttacag tcttatcatc ttcccgtaga | 480 |
| gatctacgac gttgacacgg cgtacgtaga cgactacgya cgtaccgacc aagaccatca | 540 |
| caccacyata attattagca tgcattgtca gatccaatgc aaacaamagc tactactact | 600 |
| tgattcgaca ctgaastgaa ctgaactgac aagactacgc acacgagaga gacacgcaat | 660 |
| aataatccaa caattaacca actaaacgay caactagcag acgacgatgc ctgcatctgc | 720 |
| atgcttgagc tgccagccac ttgccaccaa actgtcgtac gtcrtccgag ctrgctaatr | 780 |
| agaagctagc agggtgtgta c | 801 |

<210> SEQ ID NO 18
<211> LENGTH: 801
<212> TYPE: DNA
<213> ORGANISM: Zea mays

<400> SEQUENCE: 18

| | |
|---|---|
| tawygttaac tygtrataay tgtraacttg ttataytrga atattttat attwrtatgr | 60 |
| ttayygatcg tatttaaaat tmtgmtcrtt aymtgtgyat tttcygtmcc gaacytccaa | 120 |
| tattratact gtttccgttt ctaaagttac catwttttat ktmatttccg atataarata | 180 |
| traaaacrga cacaracaca gttggagcyg tgsaaccrak csgaccwcaa atctacrata | 240 |
| ctgcaaagca tgcgaggggc ctggtttgtg ttycctagaa gargattgsc tgmacttttta | 300 |
| cactactaaa acaagcttcy ctygataatc aaakgtatgg attttcacca tttcttcatt | 360 |
| rtattgacaa cayccttctc tggcmaaact aycgtgctaa yaatctaaca tcttsgaagc | 420 |
| ttataccaaa graagaaaca atccatgrag gtcacaagtt tamatrartt ttcaaacaat | 480 |
| aaaaattggt aacctsttsc atgcatgcat gcwggtaggc accgttggtc tkggaagttt | 540 |
| tygacagcaa gagacttcta tgctatactc cagcgcgcgc actgawygaa gctcatcatc | 600 |
| agacatggct agaygcttct cccyggtcgg aggccakaag aggcgaggac gctgtttcyt | 660 |
| tgctgcattg ggaggccttg ctgttcatgt agatcgcgta gacgatcagc tggatggtgc | 720 |
| caagcacgaa gcctatccca ttggggatct gcaygcagag agcgatcgag aggttctgtt | 780 |
| tagtatgggt agcggaaaag a | 801 |

<210> SEQ ID NO 19
<211> LENGTH: 501
<212> TYPE: DNA
<213> ORGANISM: Zea mays

<400> SEQUENCE: 19

| | |
|---|---|
| atcccatccc ttctctacgg gtcgagtcaa cgggagggac tgcatgcatg caggcagtac | 60 |
| atctggccgc tgctgtcgcg tagcagcagc agcaggcccc ttccttgact cgacaaatct | 120 |
| actactgatc gatatcgact cactctgcta ttacacttta accaacctac gcctccacgg | 180 |
| aaatggccat gtcgggcttg atcgccagct gctccggcgg cgccatgggt ccagggacgc | 240 |
| cgccgtcggc cacgccggac gcatctgccc ctgctcccgc agctgcctcg gcggcgccgg | 300 |
| cgcaggtgac aggctccacg tccacgtcga cgaccacgac cacctgcggc tcgtgcacct | 360 |

```
cctccaccgg cgtcggcgta gcttcgatgt cgatgtcgat ggggtgcacc tcagcaccgc      420
agctcgccct ggcctcggcc gccgccgcgg ccaccaccac ctccttggcg tgctccggca      480
gcttcgcctc ctccaccgtc a                                                501
```